(12) United States Patent
Millman et al.

(10) Patent No.: US 10,441,370 B2
(45) Date of Patent: *Oct. 15, 2019

(54) SURGICAL INSTRUMENT WITH ROBOTIC AND MANUAL ACTUATION FEATURES

(71) Applicant: INTUITIVE SURGICAL OPERATIONS, INC., Sunnyvale, CA (US)

(72) Inventors: Paul Millman, San Jose, CA (US); David Bailey, Redwood City, CA (US); Dean Hoornaert, San Jose, CA (US); David Stephen Mintz, Sunnyvale, CA (US); David Q. Larkin, Menlo Park, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 161 days.

This patent is subject to a terminal disclaimer.

(21) Appl. No.: 15/269,155

(22) Filed: Sep. 19, 2016

(65) Prior Publication Data

US 2017/0000573 A1 Jan. 5, 2017

Related U.S. Application Data

(63) Continuation of application No. 13/549,347, filed on Jul. 13, 2012, now Pat. No. 9,446,177, which is a
(Continued)

(51) Int. Cl.
*A61B 34/35* (2016.01)
*A61B 34/30* (2016.01)
(Continued)

(52) U.S. Cl.
CPC .............. *A61B 34/30* (2016.02); *A61B 34/37* (2016.02); *A61B 34/71* (2016.02); *A61B 34/74* (2016.02);
(Continued)

(58) Field of Classification Search
CPC .............. A61B 34/30; A61B 2034/301; A61B 2034/305; A61B 34/35; A61B 34/37;
(Continued)

(56) References Cited

U.S. PATENT DOCUMENTS 2,812,765 A 11/1957 Tofflemire
3,814,249 A 6/1974 Eaton
(Continued)

OTHER PUBLICATIONS

Advisory Action dated Apr. 20, 2012 for U.S. Appl. No. 11/454,476, filed Jun. 15, 2006.
(Continued)

*Primary Examiner* — Ahmed M Farah
(74) *Attorney, Agent, or Firm* — Haynes and Boone, LLP

(57) ABSTRACT

A teleoperated surgical instrument comprises a housing configured to couple to a teleoperated manipulator and an elongated tube having a first end and a second end opposite the first end. The first end is mounted to the housing and the second end has one or more openings configured to deliver or receive a fluid at a surgical site. The instrument further comprises a flow control system in the housing. The flow control system includes a first tubular member coupled to the elongated tube and a first control element rotatable relative to the housing and the first tubular member. The first control element includes a receiving portion coupled to a shaft portion. The receiving portion is configured to couple with the teleoperated manipulator and rotate to control flow of the fluid through the first tubular member.

17 Claims, 30 Drawing Sheets

Related U.S. Application Data continuation of application No. 11/341,155, filed on Jan. 27, 2006, now Pat. No. 8,241,271.

(60) Provisional application No. 60/696,482, filed on Jun. 30, 2005.

(51) Int. Cl.

| | | |
|---|---|---|
| *A61M 1/00* | (2006.01) | |
| *A61M 13/00* | (2006.01) | |
| *A61B 34/00* | (2016.01) | |
| *A61B 34/37* | (2016.01) | |
| *A61M 39/24* | (2006.01) | |
| *A61B 17/00* | (2006.01) | |
| *A61B 90/50* | (2016.01) | |

(52) U.S. Cl.
CPC ........ *A61M 1/0035* (2014.02); *A61M 1/0039* (2013.01); *A61M 1/0058* (2013.01); *A61M 13/003* (2013.01); *A61B 2017/00203* (2013.01); *A61B 2017/00477* (2013.01); *A61B 2034/305* (2016.02); *A61B 2090/506* (2016.02); *A61B 2217/005* (2013.01); *A61B 2217/007* (2013.01); *A61M 2039/2473* (2013.01)

(58) Field of Classification Search
CPC ......... A61B 34/70; A61B 34/71; A61B 34/74; A61M 1/0023; A61M 1/31; A61M 1/0035; A61M 1/0039; A61M 1/0058; A61M 1/008; A61M 1/0082; A61M 1/0084; A61M 1/0086; A61M 39/22; A61M 39/223; A61M 39/227; A61M 39/228; A61M 2039/222473
USPC ........ 606/1, 130; 901/19, 22, 30, 34, 36–38, 901/40
See application file for complete search history.

(56) References Cited

U.S. PATENT DOCUMENTS

| | | |
|---|---|---|
| 4,299,221 A | 11/1981 | Phillips et al. |
| 4,369,785 A | 1/1983 | Rehkopf et al. |
| 4,370,983 A | 2/1983 | Lichtenstein |
| 4,397,640 A | 8/1983 | Haug et al. |
| 4,596,374 A | 6/1986 | Thompson et al. |
| 4,668,215 A | 5/1987 | Allgood |
| 4,755,168 A | 7/1988 | Romanelli et al. |
| 4,852,551 A | 8/1989 | Opie et al. |
| 4,873,943 A | 10/1989 | Pulvermacher |
| 5,041,110 A | 8/1991 | Fleenor |
| 5,071,412 A | 12/1991 | Noda |
| 5,078,140 A | 1/1992 | Kwoh |
| 5,100,377 A | 3/1992 | Freitas et al. |
| 5,103,825 A | 4/1992 | Hokanson et al. |
| 5,303,735 A | 4/1994 | Cerola et al. |
| 5,380,280 A | 1/1995 | Peterson |
| 5,395,312 A | 3/1995 | Desai |
| 5,429,596 A | 7/1995 | Arias |
| 5,460,604 A | 10/1995 | Arnett et al. |
| 5,472,432 A | 12/1995 | Martin |
| 5,484,402 A | 1/1996 | Saravia et al. |
| 5,514,089 A | 5/1996 | Walbrink et al. |
| 5,605,537 A | 2/1997 | Ivey |
| 5,685,821 A | 11/1997 | Pike |
| 5,688,239 A | 11/1997 | Walker |
| 5,697,898 A | 12/1997 | Devine |
| 5,810,770 A | 9/1998 | Chin et al. |
| 5,836,909 A | 11/1998 | Cosmescu |
| 5,902,264 A | 5/1999 | Toso et al. |
| 5,906,591 A | 5/1999 | Dario et al. |
| 5,931,808 A | 8/1999 | Pike |
| 5,941,867 A | 8/1999 | Kao |
| 6,004,509 A | 12/1999 | Dey et al. |
| 6,148,857 A | 11/2000 | West et al. |
| 6,149,622 A | 11/2000 | Marie |
| 6,234,205 B1 | 5/2001 | DAmelio et al. |
| 6,279,595 B1 | 8/2001 | Walrath et al. |
| 6,587,750 B2 | 7/2003 | Gerbi et al. |
| 6,594,552 B1 | 7/2003 | Nowlin et al. |
| 6,610,059 B1 | 8/2003 | West, Jr. |
| 6,689,146 B1 | 2/2004 | Himes |
| 6,695,278 B2 | 2/2004 | Ellis |
| 6,770,050 B2 | 8/2004 | Epstein |
| 6,860,878 B2 | 3/2005 | Brock |
| 8,241,271 B2* | 8/2012 | Millman ............ A61M 1/0058 604/29 |
| 9,216,243 B2 | 12/2015 | Millman et al. |
| 9,446,177 B2* | 9/2016 | Millman ............ A61M 1/0058 |
| 2002/0072736 A1 | 6/2002 | Tierney et al. |
| 2002/0173744 A1 | 11/2002 | Epstein et al. |
| 2002/0188279 A1 | 12/2002 | Waddell et al. |
| 2003/0090909 A1 | 5/2003 | Kalkbrenner |
| 2003/0109826 A1* | 6/2003 | Fowler ................ A61M 3/0258 604/131 |
| 2003/0167056 A1 | 9/2003 | Jahns et al. |
| 2003/0176766 A1 | 9/2003 | Long et al. |
| 2003/0176767 A1 | 9/2003 | Long et al. |
| 2003/0216617 A1 | 11/2003 | Hirakui et al. |
| 2003/0220609 A1* | 11/2003 | Childers ................ A61M 1/28 604/29 |
| 2004/0082915 A1 | 4/2004 | Kadan |
| 2004/0158203 A1 | 8/2004 | Cover et al. |
| 2004/0243147 A1 | 12/2004 | Lipow |
| 2005/0192532 A1 | 9/2005 | Kucklick et al. |
| 2005/0240206 A1 | 10/2005 | Sjostrom |
| 2005/0245789 A1 | 11/2005 | Smith et al. |
| 2006/0030840 A1 | 2/2006 | Nowlin et al. |
| 2006/0058617 A1 | 3/2006 | Sano et al. |
| 2006/0173403 A1 | 8/2006 | Injev |
| 2007/0005002 A1 | 1/2007 | Millman et al. |
| 2007/0156121 A1 | 7/2007 | Millman et al. |
| 2008/0086087 A1 | 4/2008 | Spohn et al. |
| 2009/0036740 A1 | 2/2009 | Finlay |
| 2009/0099520 A1 | 4/2009 | Millman et al. |

OTHER PUBLICATIONS

Advisory Action dated Mar. 20, 2009 for U.S. Appl. No. 11/341,004, filed Jan. 27, 2006.
Examiner's Answer to Appeal Brief mailed Feb. 29, 2012 for U.S. Appl. No. 11/341,004, filed Jan. 27, 2006.
Examiner Interview Summary Record dated Jul. 2, 2010 for U.S. Appl. No. 11/341,004, filed Jan. 27, 2006.
Examiner Interview Summary Record dated Apr. 26, 2011 for U.S. Appl. No. 11/341,004, filed Jan. 27, 2006.
Examiner Interview Summary Record dated Apr. 27, 2011 for U.S. Appl. No. 11/454,476, filed Jun. 15, 2006.
Final Office Action dated Sep. 1, 2011 for U.S. Appl. No. 11/454,476, filed Jun. 15, 2006.
Final Office Action dated Apr. 6, 2011 for U.S. Appl. No. 11/454,359, filed Jun. 15, 2006.
Final Office Action dated Jan. 7, 2010 for U.S. Appl. No. 11/341,004, filed Jan. 27, 2006.
Final Office Action dated Jul. 8, 2011 for U.S. Appl. No. 11/341,155, filed Jan. 27, 2006.
Final Office Action dated Jan. 10, 2012 for U.S. Appl. No. 11/454,359, filed Jun. 15, 2006.
Final Office Action dated May 12, 2010 for U.S. Appl. No. 11/454,476, filed Jun. 15, 2006.
Final Office Action dated Jan. 16, 2009 for U.S. Appl. No. 11/341,004, filed Jan. 27, 2006.
Final Office Action dated Feb. 18, 2014 for U.S. Appl. No. 11/454,476, filed Jun. 15, 2006.
Final Office Action dated Mar. 25, 2010 for U.S. Appl. No. 11/341,155, filed Jan. 27, 2006.
Final Office Action dated Jul. 29, 2011 for U.S. Appl. No. 11/341,004, filed Jan. 27, 2006.

(56) References Cited

OTHER PUBLICATIONS

Final Office Action dated Mar. 23, 2016 for U.S. Appl. No. 11/454,476, filed Jun. 15, 2006, 23 pages.
Non-Final Office Action dated Oct. 5, 2009 for U.S. Appl. No. 11/341,155, filed Jan. 27, 2006.
Non-Final Office Action dated Aug. 6, 2008 for U.S. Appl. No. 11/341,004, filed Jan. 27, 2006.
Non-Final Office Action dated Dec. 8, 2010 for U.S. Appl. No. 11/454,476, filed Jun. 15, 2006.
Non-Final Office Action dated Nov. 19, 2010 for U.S. Appl. No. 11/341,004, filed Jan. 27, 2006.
Non-Final Office Action dated Aug. 21, 2015 for U.S. Appl. No. 11/454,476, filed Jun. 15, 2006, 23 pages.
Non-Final Office Action dated Nov. 22, 2010 for U.S. Appl. No. 11/341,155, filed Jan. 27, 2006.
Non-Final Office Action dated Sep. 22, 2011 for U.S. Appl. No. 11/454,359, filed Jun. 15, 2006.
Non-Final Office Action dated May 23, 2013 for U.S. Appl. No. 11/454,476, filed Jun. 15, 2006.
Non-Final Office Action dated Oct. 27, 2009 for U.S. Appl. No. 11/454,476, filed Jun. 15, 2006.
Non-Final Office Action dated Aug. 30, 2010 for U.S. Appl. No. 11/454,359, filed Jun. 15, 2006.
Non-Final Office Action dated Jul. 30, 2009 for U.S. Appl. No. 11/341,004, filed Jan. 27, 2006.
Notice—Defective Appeal Brief mailed May 7, 2012 for U.S. Appl. No. 11/454,476, filed Jun. 15, 2006.
Notice of Allowance dated Apr. 13, 2012 for U.S. Appl. No. 11/341,155, filed Jan. 27, 2006.
Notice of Defective Appeal Brief mailed May 7, 2012 for U.S. Appl. No. 11/454,476, filed Jun. 15, 2006.
Pease, Dudely A., "Basic Fluid Power," 1967, pp. 136-190, Prentice-Hall inc.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

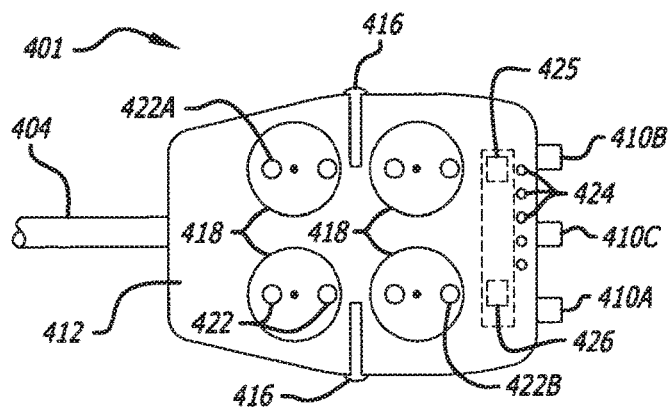
FIG. 4B
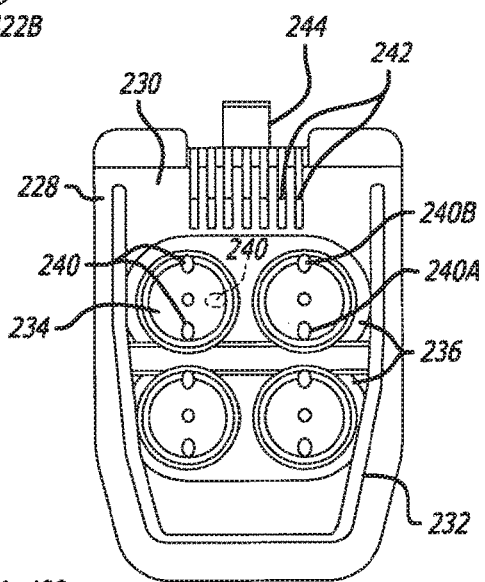
FIG. 2D
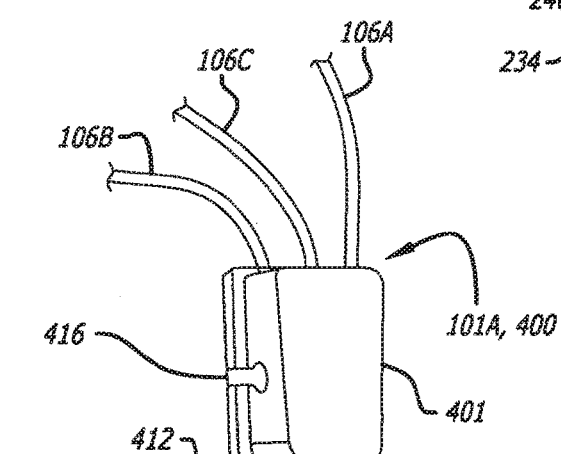
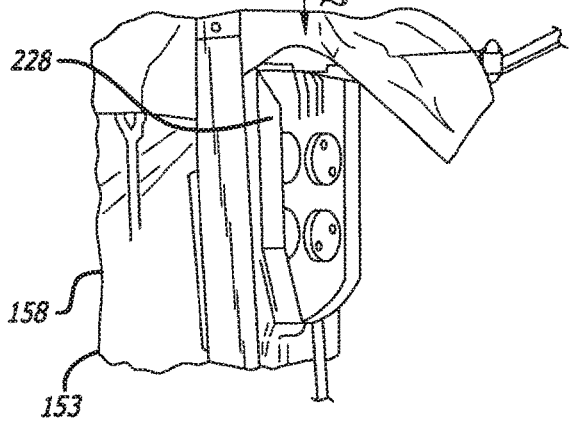
FIG. 2C

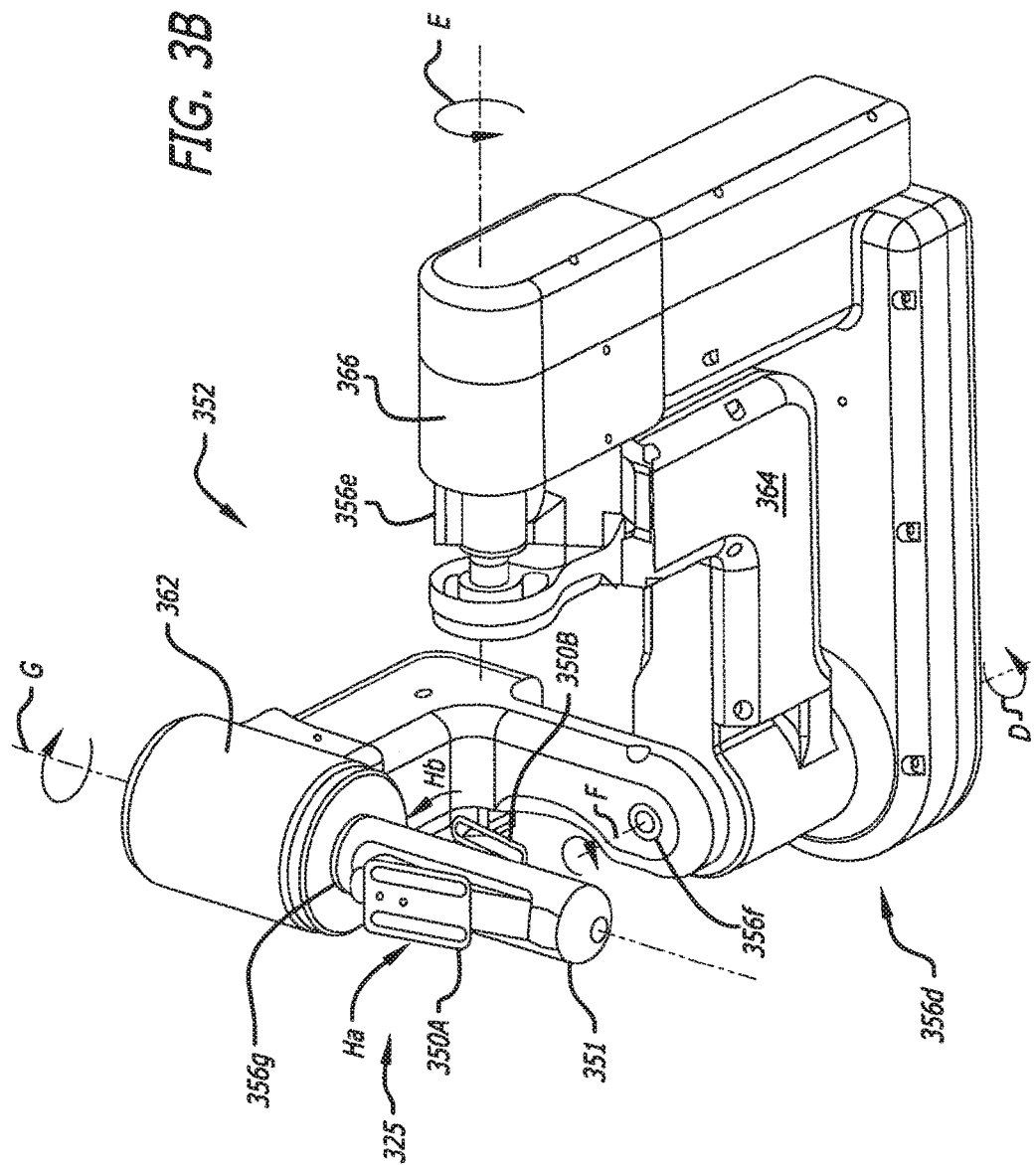

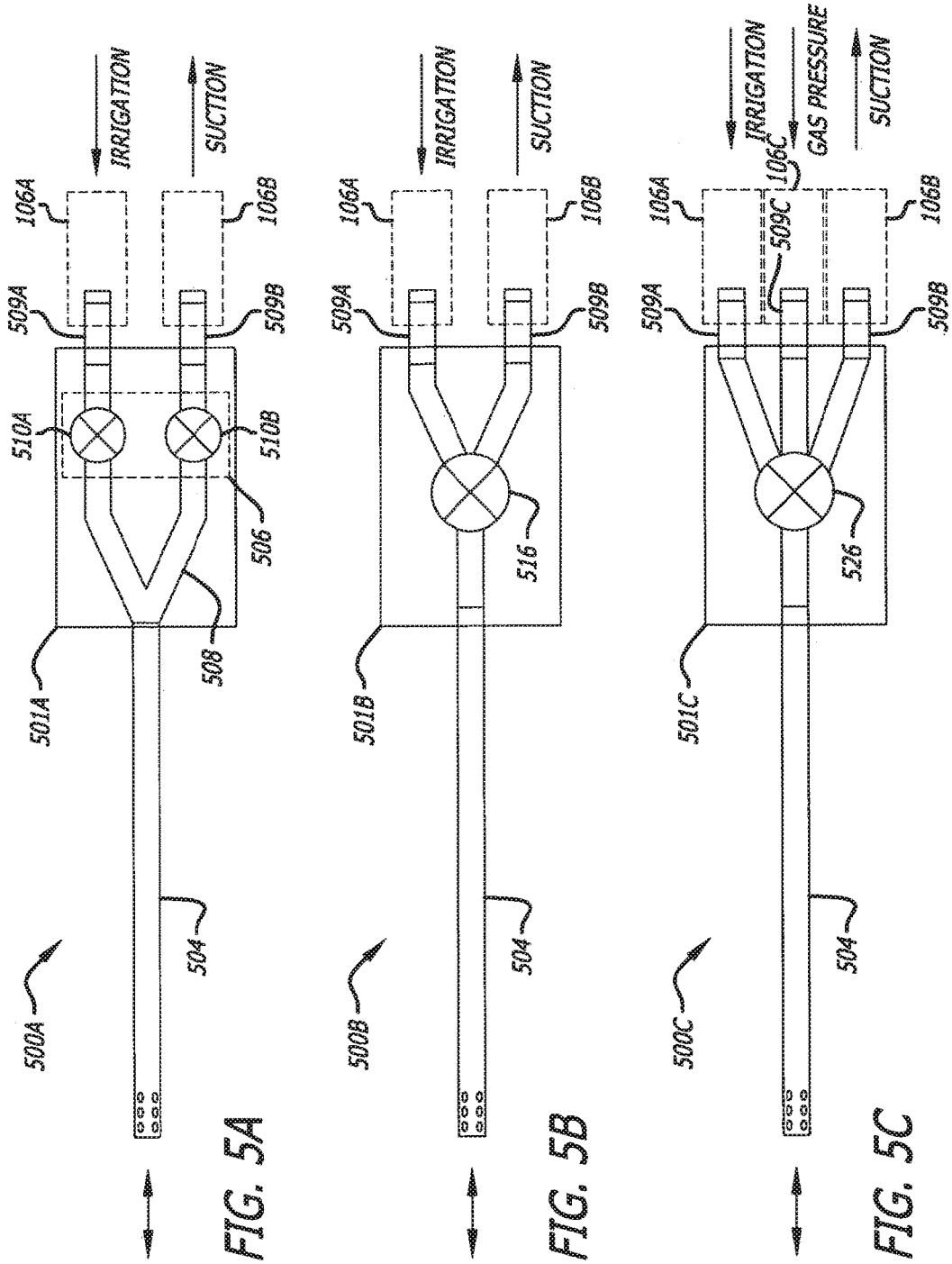

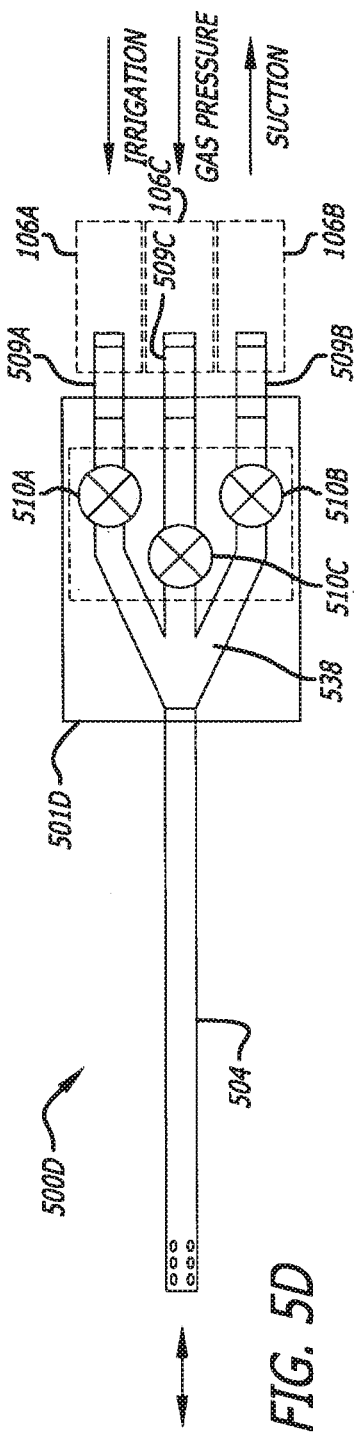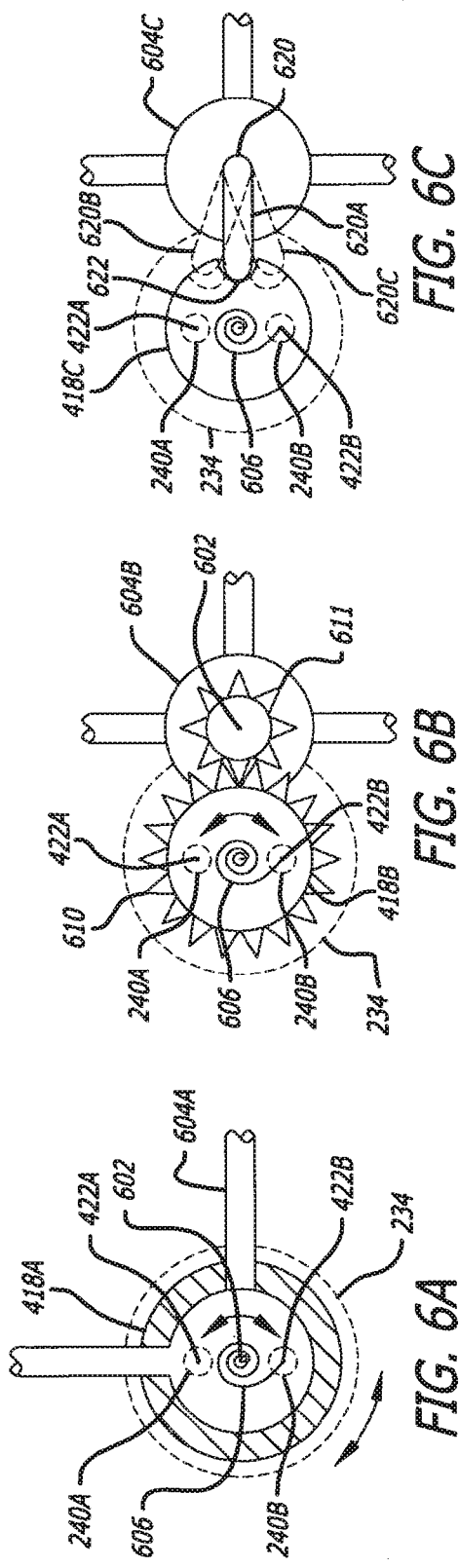

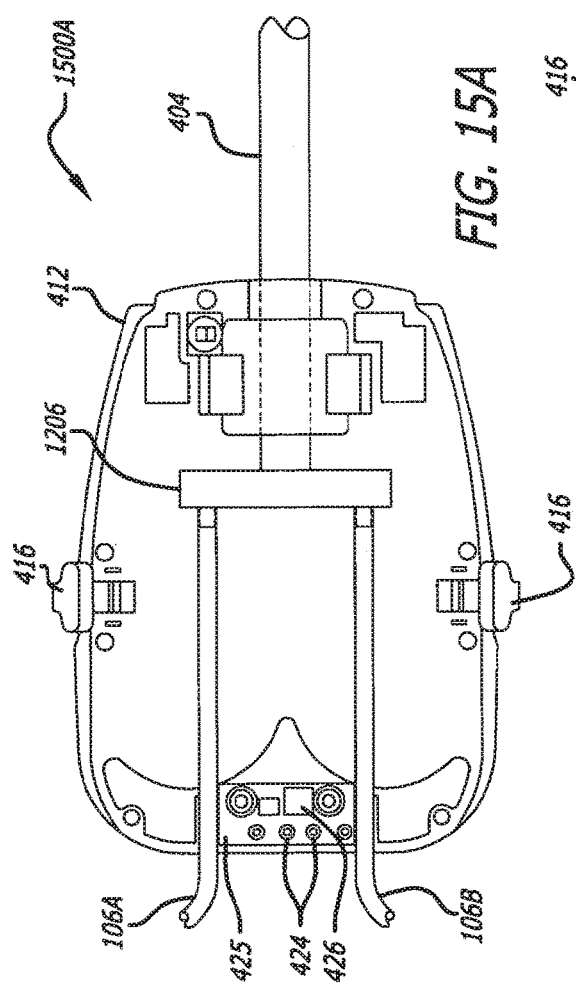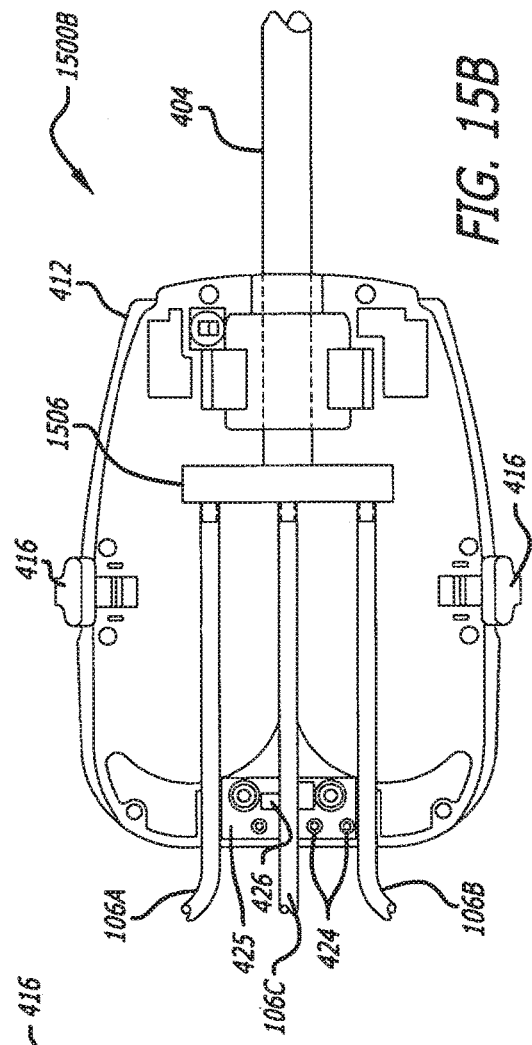

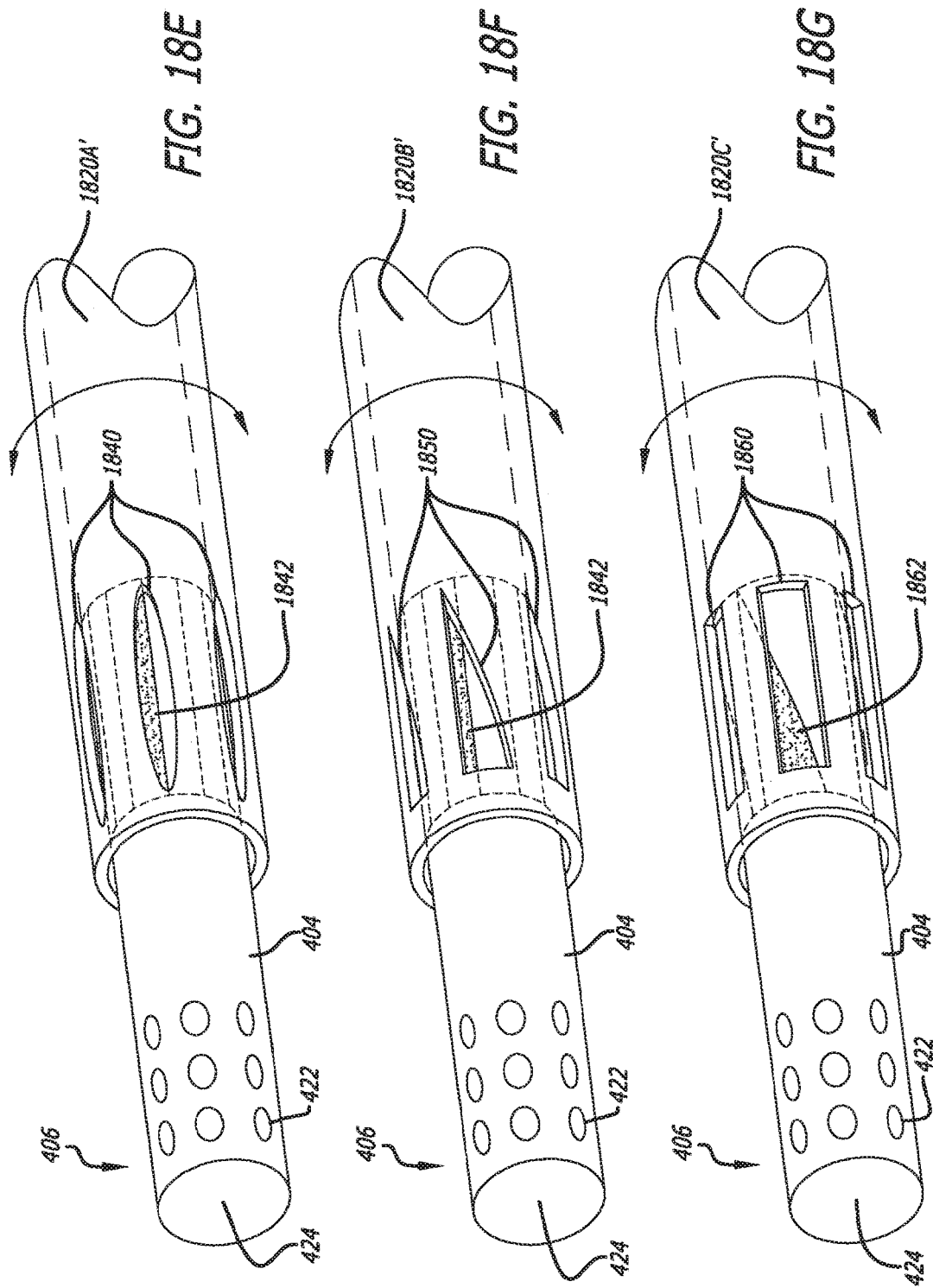

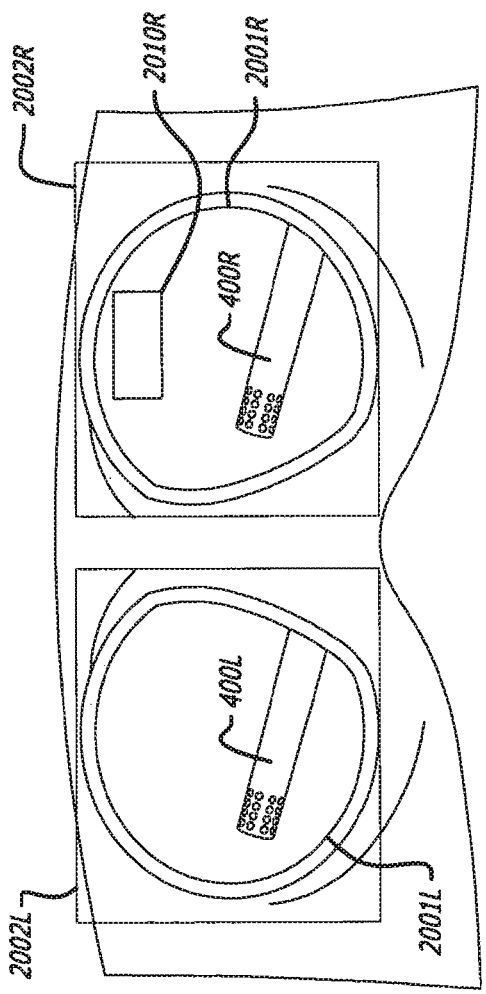
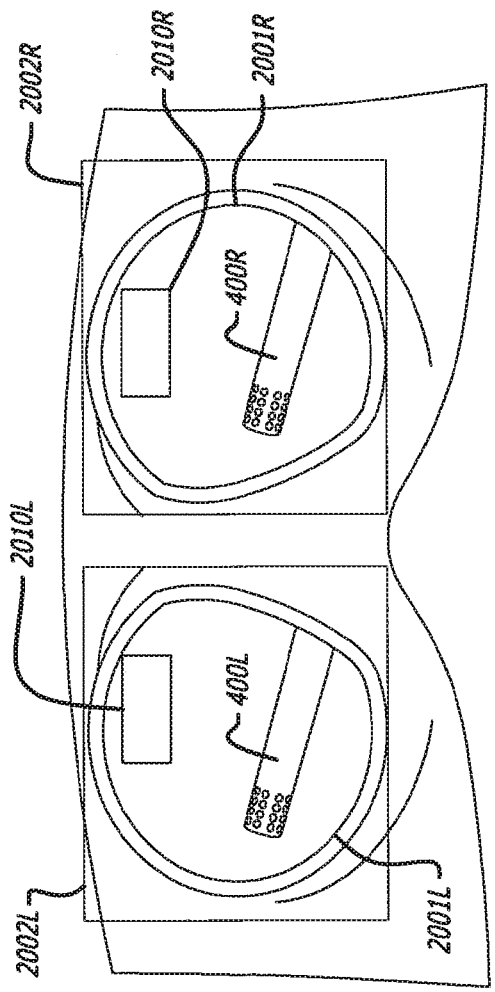
FIG. 20A
FIG. 20B

SURGICAL INSTRUMENT WITH ROBOTIC AND MANUAL ACTUATION FEATURES

CROSS-REFERENCES TO RELATED APPLICATIONS

This patent application is a continuation U.S. Application No. 13/549,347, filed Jul. 13, 2012, which is a continuation of and claims priority from co-pending and commonly owned U.S. patent application No. 11/341,155, entitled "ROBOTIC SURGICAL INSTRUMENTS WITH A FLUID FLOW CONTROL SYSTEM FOR IRRIGATION, ASPIRATION, AND BLOWING," filed on Jan. 27, 2006, which in turn claims priority from U.S. Provisional Patent Application No. 60/696,482 entitled "IRRIGATION, ASPIRATION, AND BLOWING FOR ROBOTIC SURGERY," filed on Jun. 30, 2005, all of which are by inventors Paul Millman et al., and all of which are incorporated by reference herein in their entireties and for all purposes.

This patent application is also related to commonly owned U.S. patent application Nos. 11/341,004 filed Jan. 27, 2006; 13/443,852 filed Apr. 10, 2012, which is a continuation of and claims priority from 11/454,359 filed Jun. 15, 2006; and 11/454,476 filed Jun. 15, 2006, all of which also claim priority from U.S. Provisional Patent Application No. 60/696,482, and all of which are also incorporated by reference herein in their entireties and for all purposes.

FIELD

The embodiments of the invention relate generally to surgical instruments for robotic surgery. More particularly, the embodiments of the invention relate to irrigation/aspiration/blowing devices for surgery.

BACKGROUND

During surgery on a patient, it is often desirable to irrigate a surgical site with a fluid, such as water, to clean or clear away blood, tissue, or other items obscuring the vision of a surgeon in the surgical site. Suction or aspiration in the surgical site may also be used to vacuum away blood, tissue, or other items obscuring the vision of the surgeon in the surgical site.

Hand held surgical instruments have typically been used to provide irrigation and/or aspiration. The surgeon typically does not operate the hand held surgical instrument that provides irrigation and/or aspiration. An assistant surgeon or nurse handling such instruments may provide irrigation and/or aspiration of the surgical site. The surgeon gives verbal instructions to the assistant surgeon or nurse to provide irrigation and/or aspiration of the surgical site. If the surgeon could both control the surgical instruments and the irrigation and aspiration of the surgical site, verbal instructions could be reduced and surgical procedures may be more efficient.

BRIEF SUMMARY

The embodiments of the invention are summarized by the claims that follow below.

BRIEF DESCRIPTIONS OF THE DRAWINGS

FIG. 2C illustrates mounting of the irrigation/aspiration/blowing robotic surgical tool to an adapter of the robotic surgical arm of FIG. 2B.

FIG. 2D illustrates a top view of the adapter of the robotic surgical arm of FIG. 2C to which the irrigation/aspiration/blowing robotic surgical tool may be mounted.

FIG. 3B is a perspective view of an exemplary gimbaled device pivotally supporting a touch sensitive handle for the robotic surgical master control console of FIG. 3A to control robotic surgical tools including an irrigation/aspiration/blowing robotic surgical tool.

FIG. 4B is a back side view of a portion of the irrigation/aspiration/blowing robotic surgical tool of FIG. 4A.

FIG. 5A is a schematic flow diagram of an irrigation/aspiration robotic surgical tool using two-way two-position valves.

FIG. 5B is a schematic flow diagram of an irrigation/aspiration robotic surgical tool using a three-way three-position valve.

FIG. 5C is a schematic flow diagram of an irrigation/aspiration/blowing robotic surgical tool using a four-way four-position valve.

FIG. 5D is a schematic flow diagram of an irrigation/aspiration/blowing robotic surgical tool using two-way two-position valves.

FIGS. 6A-6C are top views of rotationally actuated rotatable valves for use with the irrigation/aspiration/blowing robotic surgical tool and the robotic surgical arm.

FIGS. 15A-15B are top views of irrigation/aspiration/blowing robotic surgical tools with covers removed to respectively show three-way and four-way couplers and replaceable tubing coupled thereto.

FIG. 18E is a perspective view of a first tip for the irrigation/aspiration/blowing robotic surgical tool of FIG. 18D with a rotational sleeve around the flow tube that rotates to reveal a scale and provide user feedback.

FIG. 18F is a perspective view of a second tip for the irrigation/aspiration/blowing robotic surgical tool of FIG. 18D with a rotational sleeve around the flow tube that rotates to reveal a scale and provide user feedback.

FIG. 18G is a perspective view of a third tip for the irrigation/aspiration/blowing robotic surgical tool of FIG. 18D with a rotational sleeve around the flow tube that rotates to reveal a scale and provide user feedback.

FIG. 20A illustrates a viewer of the master control console of FIG. 3A with an icon overlay in a single side to provide user feedback as to the control of the irrigation/aspiration/blowing robotic surgical tool.

FIG. 20B illustrates a viewer of the master control console of FIG. 3A with an icon overlay in both left and right sides to provide three-dimensional user feedback as to the control of the irrigation/aspiration/blowing robotic surgical tool.

DETAILED DESCRIPTION

Figure 1:
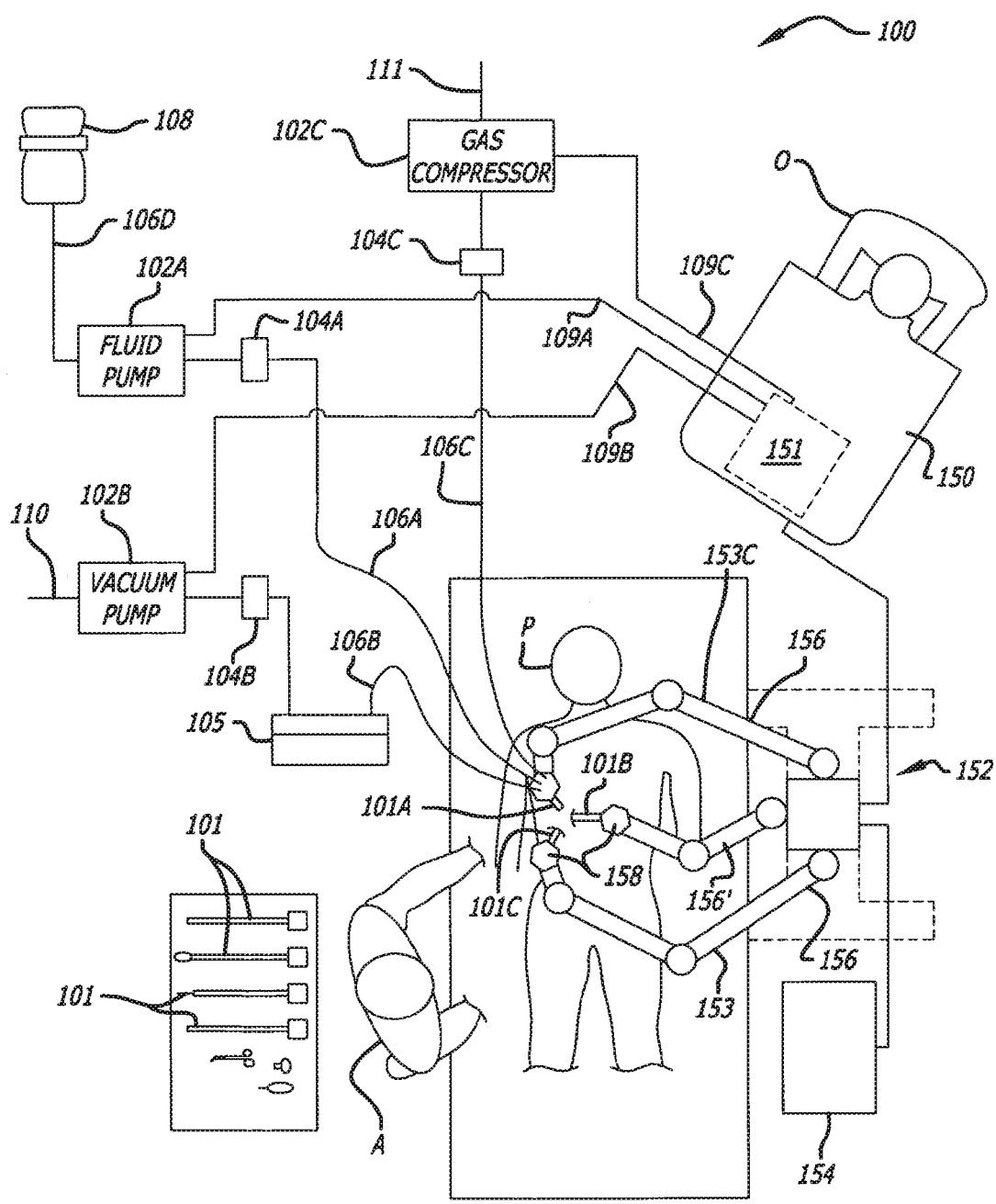
FIG. 1 is a block diagram of a robotic surgery system to perform minimally invasive robotic surgical procedures using an irrigation/aspiration/blowing robotic surgical tool.

In the following detailed description of the embodiments of the invention, numerous specific details are set forth in order to provide a thorough understanding of the embodiments of the invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

The embodiments of the invention include a method, apparatus, and system for robotically controlled irrigation/aspiration/blowing of an internal or external surgical area or site where robotic surgery is being performed. Aspiration may also be referred to as suction.

In one embodiment of the invention a robotic surgical system is provided including a master control console, a surgical manipulator, a first hose, and a first pump. The master control console is used to generate control signals to cause one or more fluids to flow into or out of a surgical site. The surgical manipulator is coupled to the master control console to receive the control signals. The surgical manipulator includes at least one robotic arm to manipulate at least one robotic surgical instrument, and a surgical instrument coupled to the robotic arm. The surgical manipulator controls the surgical instrument in response to the control signals to control the flow of the one or more fluids into or out of the surgical site. The surgical instrument has a first robotically controlled valve responsive to the surgical manipulator and a hollow tube having an opening at one end to direct the flow of one or more fluids in the surgical site. The first robotically controlled valve has a first port and a second port and the hollow tube has a first end coupled to the second port of the first robotically controlled valve. The first hose has a first end coupled to the first port of the first robotically controlled valve. The first hose transports a first fluid to the first robotically controlled valve. The first pump has a port coupled to a second end of the first hose. The first pump pumps a first fluid through the first hose to the first robotically controlled valve of the surgical instrument.

In another embodiment of the invention, a robotic surgical system is provided including a master control console, a surgical manipulator, and a first pump. The master control console generates control signals to cause a fluid to flow into or out of a surgical site. The surgical manipulator is coupled to the master control console to receive the control signals. The surgical manipulator includes at least one robotic arm to manipulate at least one surgical instrument. A surgical instrument is coupled to the robotic arm to control the flow of a fluid into or out of the surgical site. The surgical instrument has a first hose, a first robotically controlled pinch valve, and a hollow tube. The first hose is flexible and has a first end and a second end. The first robotically controlled pinch valve receives the first hose. The first robotically controlled pinch valve squeezes and pinches closed the first hose and releases and opens the first hose. The hollow tube has a first end to couple to the first end of the first hose. The first pump has a port coupled to the second end of the first hose.

In another embodiment of the invention, a method is provided. The method includes generating a first control signal to control a robotic surgical instrument; coupling the first control signal into the robotic surgical instrument; and opening a first valve in the robotic surgical instrument to flow a first fluid over a surgical site in response to the first control signal.

In another embodiment of the invention, another method is provided. The method includes mounting an irrigation-aspiration robotic surgical instrument to a robotic arm of a robotic surgical manipulator; coupling at least one hose from the irrigation-aspiration robotic surgical instrument to at least one pump; inserting a tip of a hollow tube of the irrigation-aspiration robotic surgical instrument into a patient near a surgical site; controlling a flow of a fluid between the surgical site and the irrigation-aspiration robotic surgical instrument; and monitoring a level of the flow of the fluid between the surgical site and the irrigation-aspiration robotic surgical instrument.

In yet another embodiment of the invention, a robotic surgical instrument is provided for the control of flows of one or more fluids into and out of a surgical site. The robotic surgical instrument includes a housing, a flow control system mounted in the housing, a hollow tube having a first end mounted in the housing, and one or more hose fittings having a first end coupled to the flow control system. The housing can couple the robotic surgical instrument to a robotic arm. The flow control system includes one or more controlled valves to control the flow of one or more fluids through the robotic surgical instrument. The first end of the hollow tube couples to the flow control system. The one or more hose fittings have a second end to respectively couple to one or more hoses.

In still another embodiment of the invention, another robotic surgical instrument is provided for the control of flows of one or more fluids into and out of a surgical site.

The robotic surgical instrument includes an interface base, a hollow tube having a proximal end mounted to the interface base, a three-way coupler having a first port coupled to the proximal end of the hollow tube, a first robotically controlled valve coupled to the interface base, and a second robotically controlled valve coupled to the interface base. The interface base can mechanically and electrically couple to an end of a robotic arm. The hollow tube further has a distal end for placement in a surgical site to allow the flow of fluids into and out of a surgical site. The three-way coupler further has a second port and a third port to couple the first port, the second port, and the third port together to flow fluids there-between. The first robotically controlled valve having a first port to couple to a first hose and a second port coupled to the second port of the three-way coupler. The first robotically controlled valve controls the flows of a first fluid. The second robotically controlled valve having a first port to couple to a second hose and a second port coupled to the third port of the three-way coupler. The second robotically controlled valve controls the flows of a second fluid.

Robotic surgery generally involves the use of a robot manipulator that has multiple robotic manipulator arms. One or more of the robotic manipulator arms often support a surgical tool which may be articulated (such as jaws, scissors, graspers, needle holders, micro dissectors, staple appliers, tackers, suction/irrigation tools, clip appliers, or the like) or non-articulated (such as cutting blades, cautery probes, irrigators, catheters, suction orifices, or the like). One or more of the robotic manipulator arms are often used to support a surgical image capture device such as an endoscope (which may be any of a variety of structures such as a laparoscope, an arthroscope, a hysteroscope, or the like), or, optionally, some other imaging modality (such as ultrasound, fluoroscopy, magnetic resonance imaging, or the like). Typically, the arms will support at least two surgical tools corresponding to the two hands of a surgeon and one image capture device.

Robotic surgery may be used to perform a wide variety of surgical procedures, including but not limited to open surgery, neurosurgical procedures (such as stereotaxy), endoscopic procedures (such as laparoscopy, arthroscopy, thoracoscopy), and the like.

Robotic Surgical System

Referring now to FIG. 1, a block diagram of a robotic surgery system 100 is illustrated to perform minimally invasive robotic surgical procedures using an irrigation/aspiration/blowing (IAB) robotic surgical tool 101A. The irrigation/aspiration/blowing robotic surgical tool 101A is a robotic endoscopic surgical instrument that is manipulated by a slaved robotic manipulator and remotely controlled by control signals received from a master control console. In contrast, manual endoscopic surgical instruments are directly controlled by hand.

A user or operator O (generally a surgeon) performs a minimally invasive surgical procedure on patient P by manipulating input devices at a master control console 150. A computer 151 of the console 150 directs movement of robotically controlled endoscopic surgical instruments (generally numbered 101), effecting movement of the instruments using a robotic surgical manipulator 152. The robotic surgical manipulator 152 may also be referred to as robotic patient-side cart system or simply as a cart. The robotic surgical manipulator 152 has one or more robotic arms 153. Typically, the robotic surgical manipulator 152 includes at least three robotic manipulator arms 153 supported by linkages, with a central arm supporting an endoscopic camera and the robotic arms 153 to left and right of center supporting tissue manipulation tools and the irrigation/aspiration/blowing robotic surgical tool 101A such as the robotic manipulator arm 153C.

An assistant A may assist in pre-positioning of the robotic surgical manipulator 152 relative to patient P as well as swapping tools or instruments 101 for alternative tool structures, and the like, while viewing the internal surgical site via an assistant's display 154. The image of the internal surgical site shown to A by the assistant's display 154 and operator O by surgeon's console 150 is provided by one of the surgical instruments 101 supported by the robotic surgical manipulator 152.

Generally, the robotic arms 153 of robotic surgical manipulator 152 include a positioning portion and a driven portion. The positioning portion of the robotic surgical manipulator 152 remains in a fixed configuration during surgery while manipulating tissue. The driven portion of the robotic surgical manipulator 152 is actively articulated under the direction of the operator O generating control signals at the surgeon's console 150 during surgery. The actively driven portion of the arms 153 is herein referred to as an end effector 158. The positioning portion of the robotic arms 153 that are in a fixed configuration during surgery may be referred to as positioning linkage and/or "set-up joint" 156, 156'.

To support the irrigation/aspiration/blowing robotic surgical tool 101A, the robotic surgical system may further include one or more pumps 102A-102C, one or more inline filters 104A-104C, and one or more hoses 106A-106C. For irrigation, the pump 102A is a sterile fluid pump and may be an intravenous (IV) pump with an input port or inlet coupled to an IV bag 108 through a hose 106D. The output port or outlet of the pump 102A may couple to the robotic surgical instrument 101A directly or through the inline filter 104A. The IV bag 108 may have a pressure cuff. For aspiration, the pump 102B is a vacuum pump 102B with an output port 110 exhausting to atmosphere and an input port coupling to a suction canister 105 through the inline filter 104B. In an alternate embodiment of the invention, suction may be provided to rooms at a wall inlet to isolate the noise of the vacuum pump 102B. For blowing, the pump 102C is a gas compressor with an input port coupled to a source of gas 111, such as oxygen or air, and an output port coupled to the instrument 101A through the inline filter 104C.

The one or more hoses 106A-106C may be joined together along a portion of their length and into one end to couple to the instrument 101A for ease of coupling and to readily manage a plurality of hoses as one unit at the robotic manipulator 152. Towards the opposite end, the one or more hoses 106A-106C may separate to couple to the inline filters, the pumps, the canister 105, or other pipe fittings as the case may be.

In one embodiment of the invention, the master control console 150 may control the one or more pumps 102A-102C and any valves thereat in order to control fluid flow between the pumps and the instrument 101A into and out of the surgical site. One or more control signal lines 109A-109C may couple between the computer 151 and the one or more pumps 102A-102C and any valves thereat in order that they may be controlled by control signals from the master control console 150. In which case, the hoses 106A-106C may simply couple to a coupler within the instrument 101A as is discussed further below with reference to FIGS. 15A-15B.

Figure 2A:
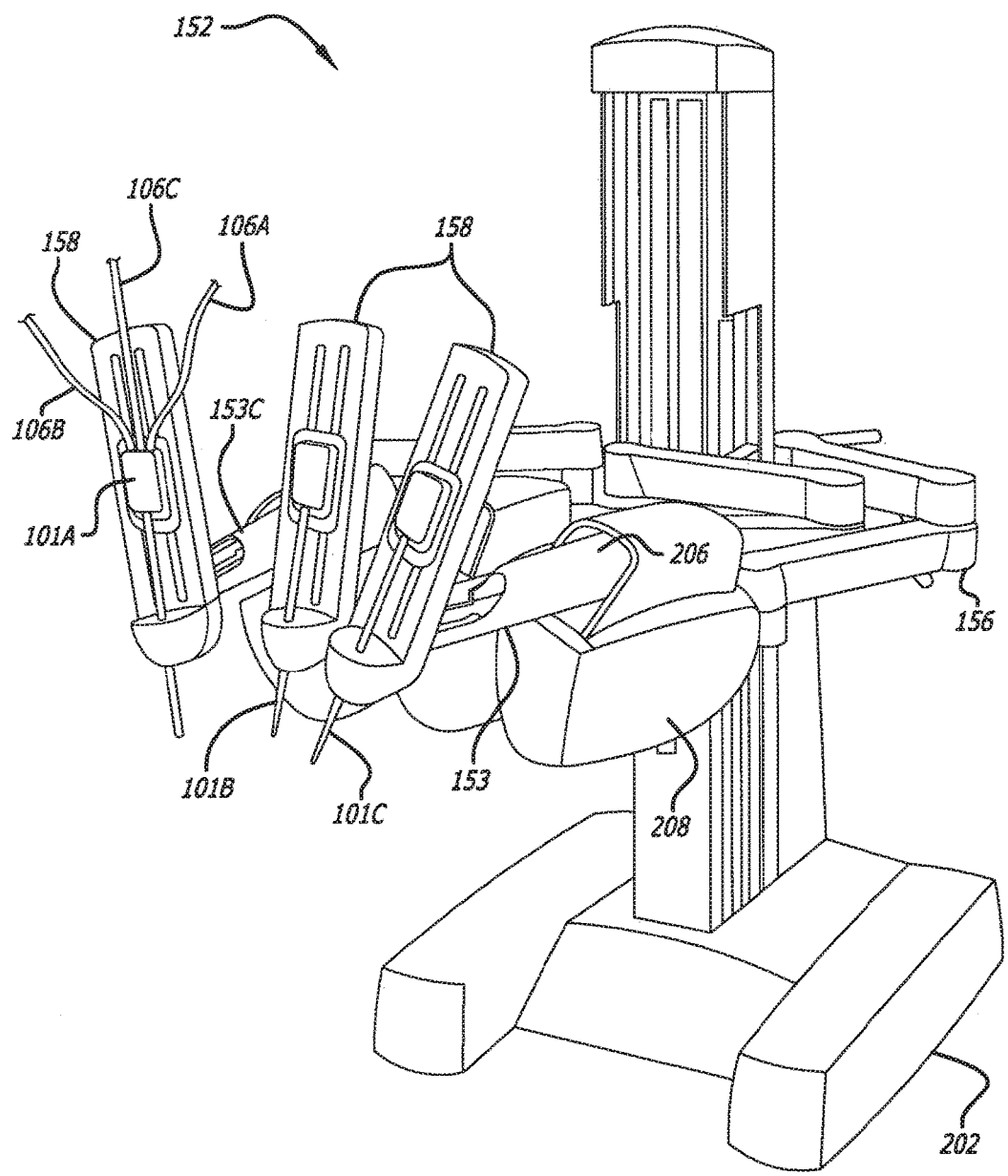
FIG. 2A is a perspective view of a robotic surgical manipulator with a plurality of robotic surgical arms at least one of which includes an irrigation/aspiration/blowing robotic surgical tool.

Referring now to FIG. 2A, a perspective view of the robotic surgical manipulator 152 is illustrated. The robotic surgical manipulator 152 has one or more robotic surgical arms 153. The robotic arm 153C includes an irrigation/aspiration/blowing robotic surgical tool 101A coupled thereto at the end effector 158. The robotic surgical manipulator 152 further includes a base 202 from which the robotic surgical instruments 101 may be supported. More specifically, the robotic surgical instruments 101 are each supported by the positioning linkage 156 and the end effector 158 of the arms 153. It should be noted that these linkage structures are here illustrated with protective covers 206,208 extending over much of the robotic arms. It should be understood that these protective covers 206,208 are optional, and may be limited in size or entirely eliminated in some embodiments to minimize the inertia that is manipulated by the servomechanism, and to limit the overall weight of robotic surgical manipulator 152.

The robotic surgical manipulator 152 generally has dimensions suitable for transporting between operating rooms. It typically can fit through standard operating room doors and onto standard hospital elevators. The robotic surgical manipulator 152 may have a weight and a wheel (or other transportation) system that allows the cart to be positioned adjacent an operating table by a single attendant. The robotic surgical manipulator 152 may be sufficiently stable during transport to avoid tipping, and to easily withstand overturning moments that may be imposed at the ends of the robotic arms during use.

Figure 2B:
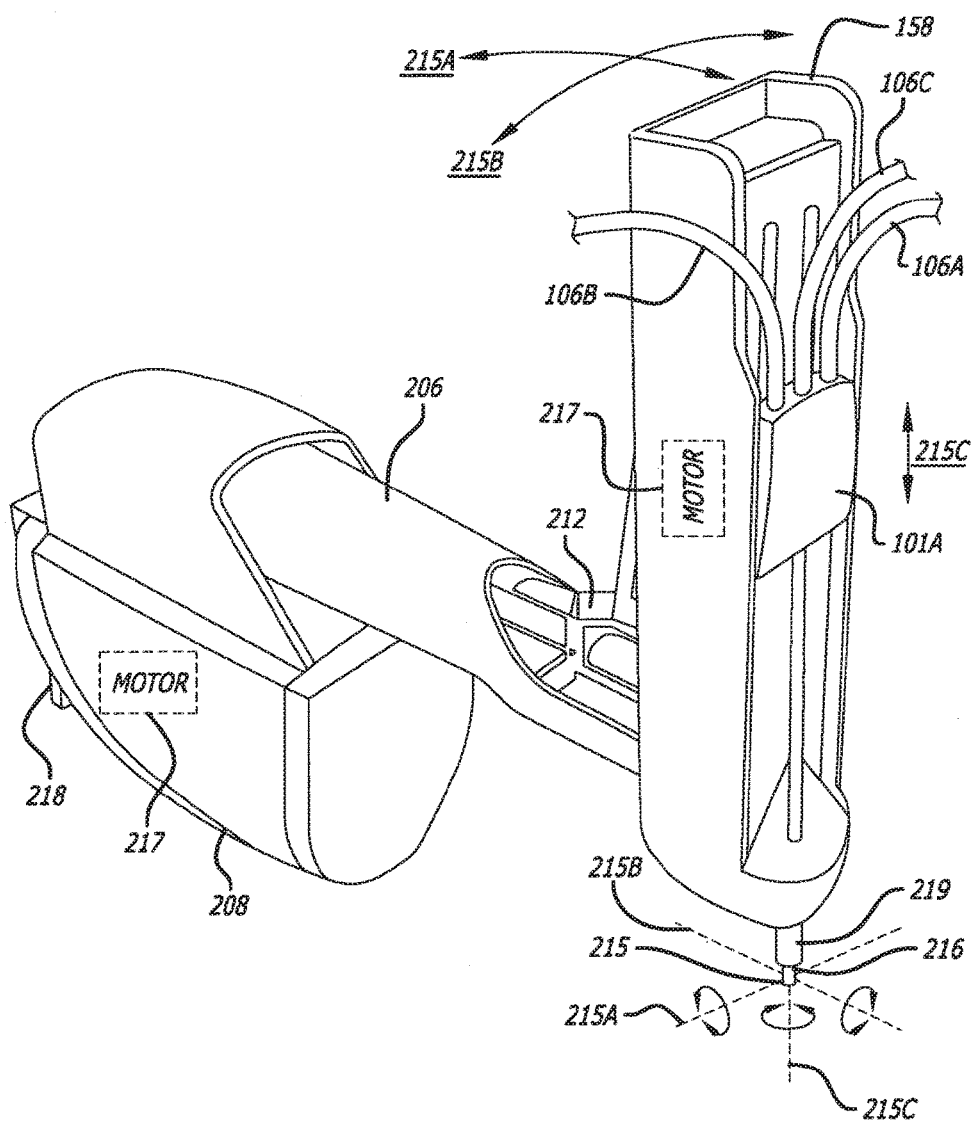
FIG. 2B is a perspective view of the robotic surgical arm including the irrigation/aspiration/blowing robotic surgical tool mounted thereto.

Referring now to FIG. 2B, a perspective view of the robotic surgical arm 153C is illustrated including the irrigation/aspiration/blowing robotic surgical tool 101A mounted thereto. Each of the robotic manipulating arms 153 preferably includes a linkage 212 that constrains the movement of the surgical tool 101 mounted thereto. More specifically, linkage 212 includes rigid links coupled together by rotational joints in a parallelogram arrangement so that the robotic surgical tool 101A rotates around a point 215 in space. At the point 215, the robotic arm can pivot the robotic surgical tool 101A about a pitch axis 215A and a yaw axis 215B. The pitch and yaw axes intersect at the point 215, which is aligned along a shaft 216 of robotic surgical tool 101A. In the case of the IAB robotic surgical tool 101A, the shaft is a hollow tube as is further discussed below.

The robotic arm provides further degrees of freedom of movement to the robotic surgical tool 101A. Along an insertion axis 215C, parallel to the central axis of the shaft 216 of the robotic surgical tool 101A, the robotic surgical tool 101A may slide into and out from a surgical site. The robotic surgical tool 101A can also rotate about the insertion axis 215C. As the robotic surgical tool 101A slides along or rotates about the insertion axis 215C, the center point 215 is relatively fixed with respect to the base 218. That is, the entire robotic arm is generally moved in order to maintain or re-position back to the center point 215.

The linkage 212 of the robotic arm 153 is driven by a series of motors 217 therein in response to commands from a processor or computer. The motors 217 in the robotic arm are also used to rotate and/or pivot the robotic surgical tool 101A at the point 215 around the axes 215A-215C. If a robotic surgical tool 101 further has end effectors to be articulated or actuated, still other motors 217 in the robotic arm may be used to do so. A flow control system in the IAB robotic surgical tool 101A may be actuated by these other motors in the robotic arm 153. However, alternative means may also be used to actuate or control the flow control system in the IAB robotic surgical tool 101A. Additionally, the motion provided by the motors 217 may be mechanically transferred to a different location such as by using pulleys, cables, gears, links, cams, cam followers, and the like or other known means of transfer, such as pneumatics, hydraulics, or electronics.

For endoscopic surgical procedures, the end effector 158 of the robotic arm 153 is often fitted with a hollow cannula 219. The shaft or tube of the robotic surgical tool 101 may be inserted into the hollow cannula 219. The cannula 219, which may be releasably coupled to the robotic arm 153, supports the shaft or tube of the robotic surgical tool 101, preferably allowing the tool to rotate around the axis 215C and move axially through the central bore of the cannula along the axis 215C.

The robotic surgical tools 101 are generally sterile structures, often being sterilizable and/or being provided in hermetically sealed packages for use. As the robotic surgical tools 101 will be removed and replaced repeatedly during many procedures, a tool holder could potentially be exposed to contamination if the interface directly engages the tool holder. To avoid contamination to a tool holder and possible cross contamination between patients, an adaptor for coupling to robotic surgical tools 101 is provided in a robotic arm of the robotic surgical manipulator.

Referring now to FIGS. 2C, 2D, and 4B, the mounting of the irrigation/aspiration/blowing robotic surgical tool 101A to an adapter 228 of the robotic surgical arm is now briefly described.

The robotic surgical arm 153 may include an adapter 228 to which the IAB robotic surgical tool 101A or other surgical tool 101 may be mounted. FIG. 2D illustrates a front side of an exemplary adapter 228. The front side of the adaptor 128 is generally referred to as a tool side 230 and the opposite side is generally referred to as a holder side (not shown).

FIG. 4B illustrates a back side of an exemplary IAB robotic surgical tool 400 as the IAB surgical robotic tool 101A. The robotic surgical tool 400 includes an exemplary mountable housing 401 including an interface base 412 that can be coupled to the adapter 228. The interface base 412 and the adapter 228 may be electrically and mechanically coupled together to actuate the flow control system of the IAB robotic surgical tool 101A. Rotatably coupled to the interface base 412 are one or more rotatable receiving members 418. Each of the one or more rotatable receiving members 418 includes a pair of pins 422A and 422B generally referred to as pins 422. Pin 422A is located closer to the center of each rotatable receive member 418 than pin 422B. The one or more rotatable receiving members 418 can mechanically couple respectively to one or more rotatable drivers 234 of the adapter 228. The robotic surgical tool 101A may further include release levers 416 to release it from the adapter 228.

The interface base 412 may further include one or more electrical contacts or pins 424 to electrically couple to electrical connector 242 of the adapter 228. The interface base 412 may further include a printed circuit board 425 and one or more integrated circuits 426 coupled thereto and to the one or more pins 424. The one or more integrated circuits 426 may be used to identify the type of robotic surgical tool coupled to the robotic arm, so that it may be properly controlled by the master control console 150.

The adapter 228 includes one or more rotatable drivers 234 rotatably coupled to a floating plate 236. The rotatable drivers 234 are resiliently mounted to the floating plate 236 by resilient radial members which extend into a circumferential indentation about the rotatable drivers. The rotatable drivers 234 can move axially relative to floating plate 236 by deflection of these resilient structures.

The floating plate 236 has a limited range of movement relative to the surrounding adaptor structure normal to the major surfaces of the adaptor. Axial movement of the floating plate helps decouple the rotatable drivers 234 from a robotic surgical tool 101 when its release levers 416 are actuated.

The one or more rotatable drivers 234 of the adapter 228 may mechanically couple to a part of the surgical tools 101. Each of the rotatable drivers 234 may include one or more openings 240 to receive protrusions or pins 422 of rotatable receiving members 418 of the robotic surgical tools 101. The openings 240 in the rotatable drivers 234 are configured to accurately align with the rotatable receiving elements 418 of the surgical tools 101.

The inner pins 422A and the outer pins 422B of the rotatable receiving elements 418 respectively align with the opening 240A and the opening 240B in each rotatable driver. The pins 422A and openings 240A are at differing distances from the axis of rotation than the pins 422B and openings 240B so as to ensure that rotatable drivers 234 and the rotatable receiving elements 418 are not aligned 180 degrees out of phase from their intended position. Additionally, each of the openings 240 in the rotatable drivers may be slightly radially elongated so as to fittingly receive the pins in the circumferential orientation. This allows the pins 422 to slide radially within the openings 240 and accommodate some axial misalignment between the tool and the adapter 228, while minimizing any angular misalignment and backlash between the rotatable drivers 234 and the rotatable receiving elements 418. Additionally, the interaction between pins 422 and openings 240 helps restrain the robotic surgical tool 101 in the engaged position with the adapter 228 until the release levers 416 along the sides of the housing 401 push on the floating plate 236 axially from the interface so as to release the tool 101.

When disposed in a first axial position (away from the tool side 230) the rotatable drivers are free to rotate without angular limitation. The one or more rotatable drivers 234 may rotate clockwise or counter-clockwise to further actuate the systems and tools of the robotic surgical instruments 101. However, as the rotatable drivers move axially toward the tool side 230, tabs (extending radially from the rotatable drivers) may laterally engage detents on the floating plates so as to limit the angular rotation of the rotatable drivers about their axes. This limited rotation can be used to help engage the rotatable drivers the rotating members of the tool as the pins 422 may push the rotatable bodies into the limited rotation position until the pins are aligned with (and slide into) the openings 140 in the rotatable drivers.

While rotatable drivers 234 are described here, other types of drivers or actuators may be provided in the adapter 228 to actuate systems or tools of the robotic surgical instruments 101. The adapter 228 further includes an electrical connector 242 to electrically couple to surgical instruments 101.

The mounting of robotic surgical tool 101A to the adapter 228 generally includes inserting the tip or distal end of the shaft or hollow tube of the robotic surgical tool through the cannula 219 and sliding the interface base 412 into engagement with the adapter 228, as illustrated in FIG. 2C. A lip 232 on the tool side 230 of the adaptor 228 slidably receives the laterally extending portions of the interface base 412 of the robotic surgical tool. A catch 244 of adapter 228 may latch onto the back end of the interface base 412 to hold the tool 101A in position. The protrusions or pins 422 extending from the one or more rotatable members 418 of the robotic surgical tool couple into the holes 240 in the rotatable drivers 234 of the adapter 228.

The range of motion of the rotatable receiving elements 418 in the robotic surgical tool may be limited. To complete the mechanical coupling between the rotatable drivers of the adapter and the rotatable receiving elements 418, the operator O at the surgical master control console 150 may turn the rotatable drivers in one direction from center, turn the rotatable drivers in a second direction opposite the first, and then return the rotatable drivers to center. Further, to ensure that the pins 422 enter openings 240 of adapter 228, the adapter 228 and tool 101A mounted thereto may be moved along the axis 215C. The adapter 228 and tool 101A mounted thereto may be moved to an initial position so that the tip or distal end of the shaft or hollow tube is disposed within the cannula 219.

To dismount and remove the robotic surgical tool 101A, the release levers 416 may be squeezed pushing out on the mountable housing 401 to release the pins 422 from the holes 240 and the catch 244 from the back end of the interface base. The mountable housing 401 is then pulled up to slide the interface base 412 up and out from the adapter 228. The mountable housing 401 is continually pulled up to remove the tip or distal end of the shaft or hollow tube out from the cannula 219. After the robotic surgical tool 101A is dismounted, another robotic surgical tool may be mounted in its place, including a new or freshly sterilized IAB robotic surgical tool 101A.

As previously discussed, the robotic surgical tool 101A may include one or more integrated circuits 426 to identify the type of robotic surgical tool coupled to the robotic arm, such that it may be properly controlled by the master control console 150. However, the robotic surgical system may determine whether or not the robotic surgical tool is compatible or not, prior to its use.

The system verifies that the tool is of the type which may be used with the robotic surgical system 100. The one or more integrated circuits 426 may signal to the computer 151 in the master control console 150 data regarding compatibility and tool-type to determine compatibility as well as control information. One of the integrated circuits 426 may include a non-volatile memory to store and read out data regarding system compatibility, the tool-type and the control information. In an exemplary embodiment, the data read from the memory includes a character string indicating tool compatibility with the robotic surgical system 100. Additionally, the data from the tool memory will often include a tool-type to signal to the master control console how it is to be controlled. In some cases, the data will also include tool calibration information. The data may be provided in response to a request signal from the computer 151.

Tool-type data will generally indicate what kind of tool has been attached in a tool change operation. For example, the tool-type data might indicate that an IAB robotic surgical instrument 101A has been mounted to the robotic arm. The tool-type data may include information on wrist axis geometries, tool strengths, grip force, the range of motion of each joint, singularities in the joint motion space, the maximum force to be applied via the rotatable receiving elements 418, the tool transmission system characteristics including information regarding the coupling of rotatable receiving elements 418 to actuation or articulation of a system within the robotic surgical instrument.

Instead of storing all of the tool-type date in the one or more integrated circuits 426, most of the tool-type data may optionally be stored in memory or a hard drive of the computer 151 in the robotic surgical system 100. An identifier may be stored in the one or more integrated circuits 426 to signal the computer 151 to read the relevant portions of data in a look up table store in the memory or the hard drive of the computer. The tool-type data in the look-up table may be loaded into a memory of computer 151 by the manufacturer of the robotic surgical system 100. The look-up table may be stored in a flash memory, EEPROM, or other type of non-volatile memory. As a new tool-type is provided, the manufacturer can revise the look-up table to accommodate the new tool-specific information. It should be recognized that the use of tools which are not compatible with the robotic surgery system, for example, which do not have the appropriate tool-type data in an information table, could result in inadequate robotic control over robotic surgical tool by the computer 151 and the operator O.

In addition to the tool-type data, tool specific information may be stored in the integrated circuit 426, such as for reconfiguring the programming of computer 151 to control the tool. There may be calibration information, such as an offset, to correct a misalignment in the robotic surgical tool. The calibration information may be factored into the overall control of the robotic surgical tool. The storing of such calibration information can be used to overcome minor mechanical inconsistencies between tools of a single type. For example, the tool-type data including the tool-specific data may be used to generate appropriate coordinate transformations and servo drive signals to manipulate the robotic arm and rotate the rotatable drivers 234.

Additionally, some robotic surgical tools have a limited life span. Tool life and cumulative tool use information may also be stored on the tool memory and used by the computer to determine if the tool is still safe for use. Total tool life may be measured by clock time, by procedure, by the number of times the tool has been loaded onto a holder, and in other ways specific to the type of tool. Tool life data is preferably stored in the memory of the tool using an irreversible writing process.

Figure 3A:
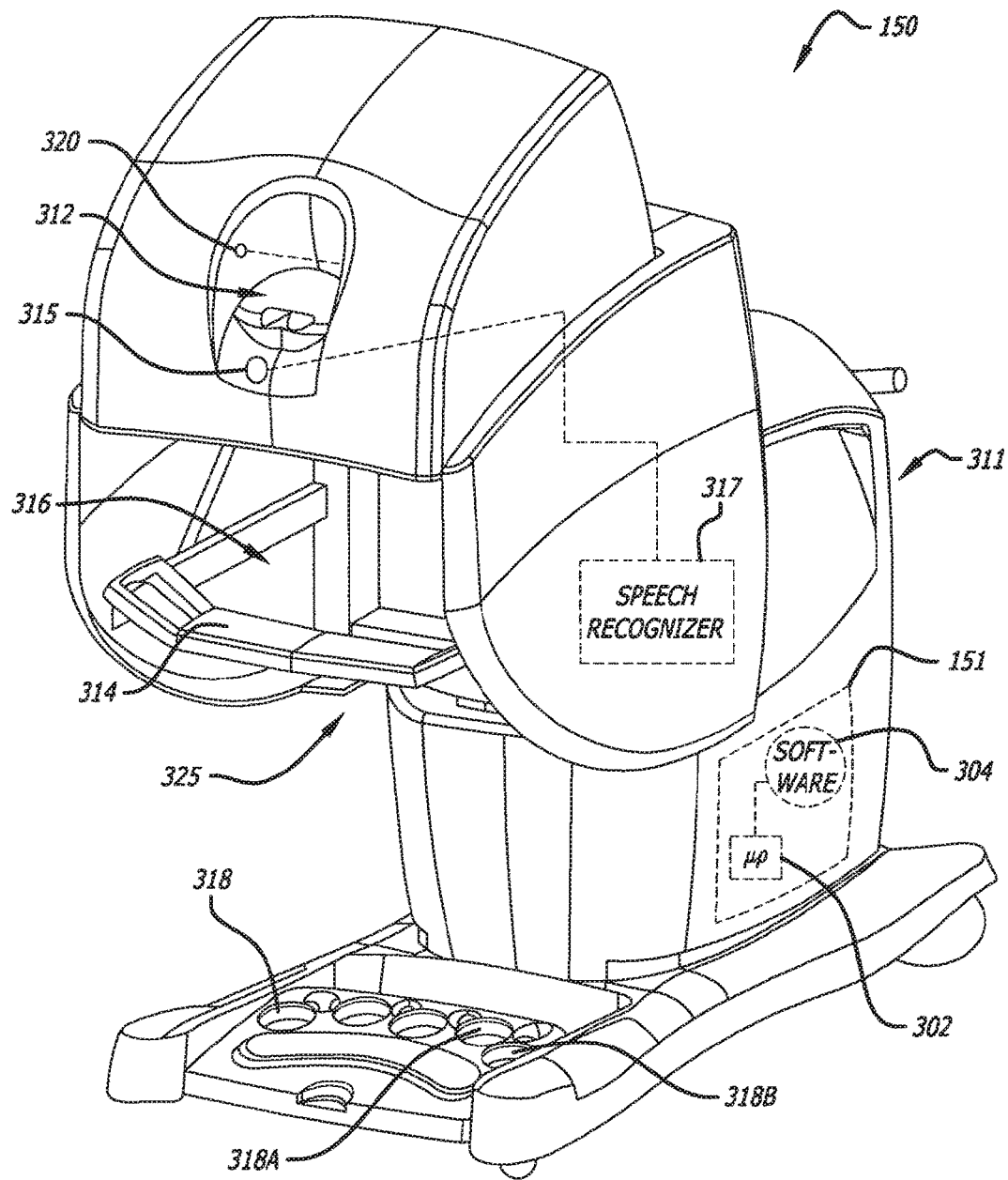
FIG. 3A is a perspective view of a robotic surgical master control console.

Referring now to FIG. 3A, a perspective view of a robotic surgical master control console 150 is illustrated. The master control console 150 of the robotic surgical system 100 includes the computer 151, a binocular viewer 312, an arm support 314, a microphone 315, a pair of control input wrists and control input arms in a workspace 316, a speech recognizer 317, foot pedals 318 (including foot pedals 318A-318B), and a viewing sensor 320.

The computer 151 may include one or microprocessors 302 to execute instructions and a storage device 304 to store software with executable instructions that may be used to generate control signals to control the robotic surgical system 100. The master control console 150 generates the control signals to control the fluid flows through the embodiments of the IAB robotic surgical instruments into and out of a surgical site.

The viewer 312 has at least one display where images of a surgical site may be viewed to perform minimally invasive surgery. As discussed further below, the viewer 312 may be used to provide user-feedback to the operator O as to the control of the fluid flow through the IAB robotic surgical instruments into and out of a surgical site.

The arm support 314 can be used to rest the elbows or forearms of the operator O (typically a surgeon) while gripping touch sensitive handles 325 (see FIGS. 3B-3C), one in each hand, of the pair of control input wrists 352 in the workspace 316 to generate control signals. The touch sensitive handles 325 are positioned in the workspace 316 disposed beyond the arm support 314 and below the viewer 312.

When using the master control console, the operator O typically sits in a chair, moves his or her head into alignment with the binocular viewer 312, and grips the touch sensitive handles 325 of the control input wrists 352, one in each hand, while resting their forearms against the arm support 314. This allows the touch sensitive handles to be moved easily in the control space 316 in both position and orientation to generate control signals.

Additionally, the operator O can use his feet to control the foot-pedals to change the configuration of the surgical system and generate additional control signals to control robotic surgical instruments.

To ensure that the operator is viewing the surgical site when controlling the robotic surgical tools 101, the master control console 150 may include the viewing sensor 320 disposed adjacent the binocular display 312. When the system operator aligns his or her eyes with the binocular eye pieces of the display 312 to view a stereoscopic image of the surgical worksite, the operator's head sets off the viewing sensor 320 to enable the control of the robotic surgical tools 101. When the operator's head is removed the area of the display 312, the viewing sensor 320 can disable or stop generating new control signals in response to movements of the touch sensitive handles in order to hold the state of the robotic surgical tools.

The computer 151 with its microprocessors 302 interprets movements and actuation of the touch sensitive handles 325 (and other inputs from the operator O or other personnel) to generate control signals to control the robotic surgical instruments 101 in the surgical worksite. In one embodiment of the invention, the computer 151 and the viewer 312 map the surgical worksite into the controller workspace 316 so it feels and appears to the operator that the touch sensitive handles 325 are working over surgical worksite.

Referring now to FIG. 3B, a perspective view of a control input wrist 352 with a touch sensitive handle 325 is illustrated. The control input wrist 352 is a gimbaled device that pivotally supports the touch sensitive handle 325 of the master control console 150 to generate control signals that are used to control the robotic surgical manipulator 152 and the robotic surgical tools 101, including an IAB robotic surgical tool 101A. A pair of control input wrists 352 are supported by a pair of control input arms in the workspace 316 of the master control console 150.

The control input wrist 352 includes first, second, and third gimbal members 362, 364, and 366. The third gimbal member 366 is rotationally mounted to a control input arm (not shown) to rotate about an axis D. As further shown in FIG. 3B, the second gimbal member 364 rotates with respect to the third gimbal member 366 about an axis E. The first gimbal member 362 rotates with respect to the second gimbal member 364 about an axis F. The handle 325 rotates with respect to the first gimbal member 362 about an axis G.

The touch sensitive handle 325 includes a tubular support structure 351, a first grip 350A, and a second grip 350B. The first grip and the second grip are supported at one end by the structure 351. The touch sensitive handle 325 can be rotated about axis G illustrated in FIGS. 3B-3C. The grips 350A, 350B can be squeezed or pinched together about the tubular structure 351. The "pinching" or grasping degree of freedom in the grips is indicated by arrows Ha,Hb in FIG. 3B and arrows H in FIG. 3C.

The touch sensitive handle 325 is rotatably supported by the first gimbal member 362 by means of a rotational joint 356g. The first gimbal member 362 is in turn, rotatably supported by the second gimbal member 364 by means of the rotational joint 356f. Similarly, the second gimbal member 364 is rotatably supported by the third gimbal member 366 using a rotational joint 356d. In this manner, the control wrist allows the touch sensitive handle 325 to be moved and oriented in the workspace 316 using three degrees of freedom.

The movements in the gimbals of the control wrist 352 to reorient the touch sensitive handle in space can be translated into control signals to control the robotic surgical manipulator 152 and the robotic surgical tools 101. In particular, the rotational motion of the touch sensitive handle 325 about axis G in FIGS. 3B-3C may be used to control the flow of fluids through the IAB robotic surgical tools.

The movements in the grips 350A,350B of the touch sensitive handle 325 can also be translated into control signals to control the robotic surgical manipulator 152 and the robotic surgical tools 101. In particular, the squeezing motion of the grips 350A, 350B over their freedom of movement indicated by arrows Ha, Hb or H, may be used to control the flow of fluids through the IAB robotic surgical tools.

In embodiments of the invention, one or a combination of both the rotational motion of the touch sensitive handle 325 and the squeezing motion of the grips 350A, 350B may be used to control the flow of fluids through the IAB robotic surgical tools. For example, the rotational motion of the touch sensitive handle 325 may be used for the control of irrigation while the squeezing motion of the grips 350A, 350B may be used for controlling suction in a surgical site.

To sense the movements in the touch sensitive handle and generate controls signals for the IAB robotic surgical tool, sensors can be mounted in the handle 325 as well as the gimbal member 362 of the control input wrist 352. Exemplary sensors may be a Hall effect transducer, a potentiometer, an encoder, or the like.

Figure 3C:
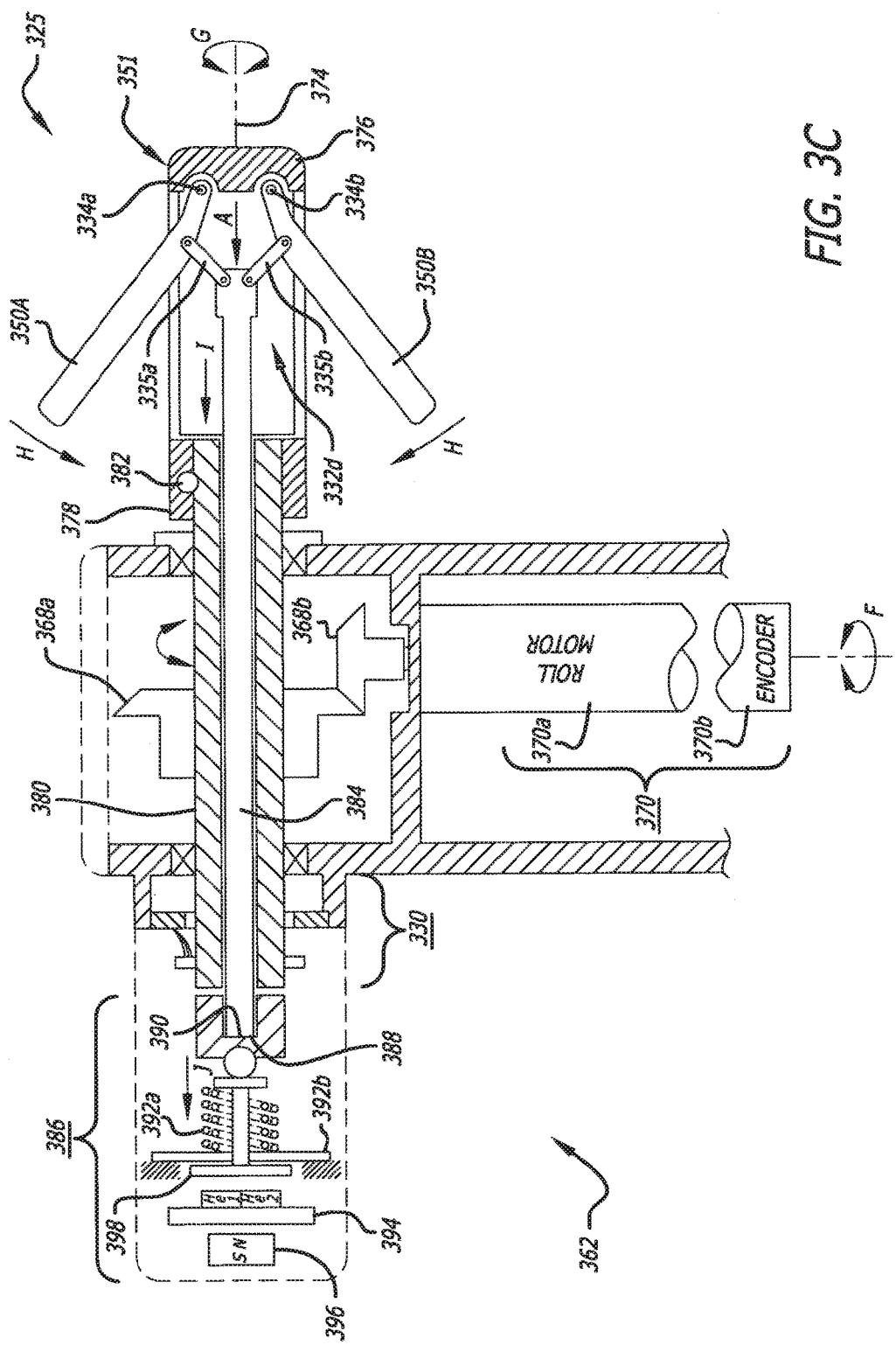
FIG. 3C is a cross-sectional view schematically illustrating mounting of the touch sensitive handle of FIG. 3B with sensors to sense gripping and rotation of the handle to control robotic surgical tools, including an irrigation/aspiration/blowing robotic surgical tool.

Referring now to FIG. 3C, a cross-sectional view of the touch sensitive handle 325 and gimbal member 362 of the control input wrist 352 is illustrated. FIG. 3C provides an example as to how the touch sensitive handle 325 can be mounted to the control input wrist 352 to sense the gripping and rotation of the handle to control robotic surgical tools 101, including IAB robotic surgical tools 101A.

As illustrated in FIG. 3C, the exemplary gimbal member 362 includes beveled gears 368a, 368b which can couple the rotational motion of the touch sensitive handle 325 to a roll sensor 370. The roll sensor 370 may use a potentiometer or encoder 370b included in a roll motor 370a to sense the rotation. Alternatively, a separate roll sensor, such as a potentiometer, may be directly coupled to the shaft 380 to sense the rotation of the touch sensitive handle. In any case, a roll sensor senses the roll motion of the touch sensitive handle 325 and generates control signals in response thereto to control the robotic surgical tools 101. The control of IAB robotic surgical tools 101A using the roll motion of the touch sensitive handle 325 is discussed below with reference to FIG. 16A.

To sense a squeezing motion in the grips 350A, 350B of the touch sensitive handle 325, a remote sensing assembly 386 may be included by the gimbal member 362. The first and second grips 350A, 350B are adapted to be squeezed together by a hand of an operator O so as to define a variable grip separation. The grip separation may be determined as a function of a variable grip angle with an axis or as a function of a variable grip separation distance, or the like. Alternative handle actuations, such as movement of a thumbwheel or knob may also be provided in the handle to control the robotic surgical instruments 101.

In the exemplary embodiment, the remote sensor assembly 386 includes a circuit board 394 on which a first and a second Hall effect sensors, HE1, HE2 are mounted. A magnet 396 is disposed distally beyond the circuit board 394 and the Hall effect sensors. A magnetic mass 398 is axially coupled to the proximally oriented surface 390 of a push rod 384. Thus, the magnetic mass 398 moves (as shown by Arrow J) with the push rod 384 and varies the magnetic field at the Hall effect sensors in response actuation of the grips 350A, 350B.

To translate the squeezing action of the grips 350A, 350B to the sensor 386, the gimbal member 362 includes a push rod 384 within the tubular handle structure 351. Each of the grips 350A, 350B pivot about a respective pivot 334a, 334b in the tubular handle structure 351. Urging links 335a. 335b respectively couple between the grips 350A, 350B and a first end of the push rod 384. The squeezing action of the grips 350A, 350B is translated into a linear motion on the push rod 384 by means of urging links 335a, 335b as shown by arrow A in FIG. 3C. A second end of the push rod 384 couples to the sensor 386. As discussed previously, the magnetic mass 398 is axially coupled to the surface 390 of the push rod 384 in order to sense the linear motion in the push rod and the squeezing motion of the grips 350A, 350B.

A biasing mechanism such as spring 392 applies a force against the squeezing motion of the grips to return them to full open when the grips are released. The biasing spring 392 may be a linear or non-linear elastic device biasing against the depression of grips 350A, 350B, e.g., a single or multiple element assembly including springs or other elastic members. For example, spring 392 may comprise a concentric dual spring assembly whereby one spring provides a "softer" bias response as the grips 350A, 350B are initially depressed, and a second spring provides a superimposed "firm" bias response as the grips 350A, 350B approach a fully depressed state. Such a non-linear bias may provide a pseudo force-feedback to the operator.

It should be noted that a wide variety of alternative sensing arrangements may be used to translate the mechanical actuation of the touch sensitive handle and control input wrist into control signals. While Hall effect sensors are included in the exemplary embodiment, alternative embodiments may include encoders, potentiometers, or a variety of alternative optical, electrical, magnetic, or other sensing structures.

Irrigation/Aspiration/Blowing Robotic Surgical Instrument

A number of embodiments of irrigation/aspiration/blowing (IAB) robotic surgical tools that can be mounted to a robotic arm in a robotic surgical system are now described.

Figure 4A:
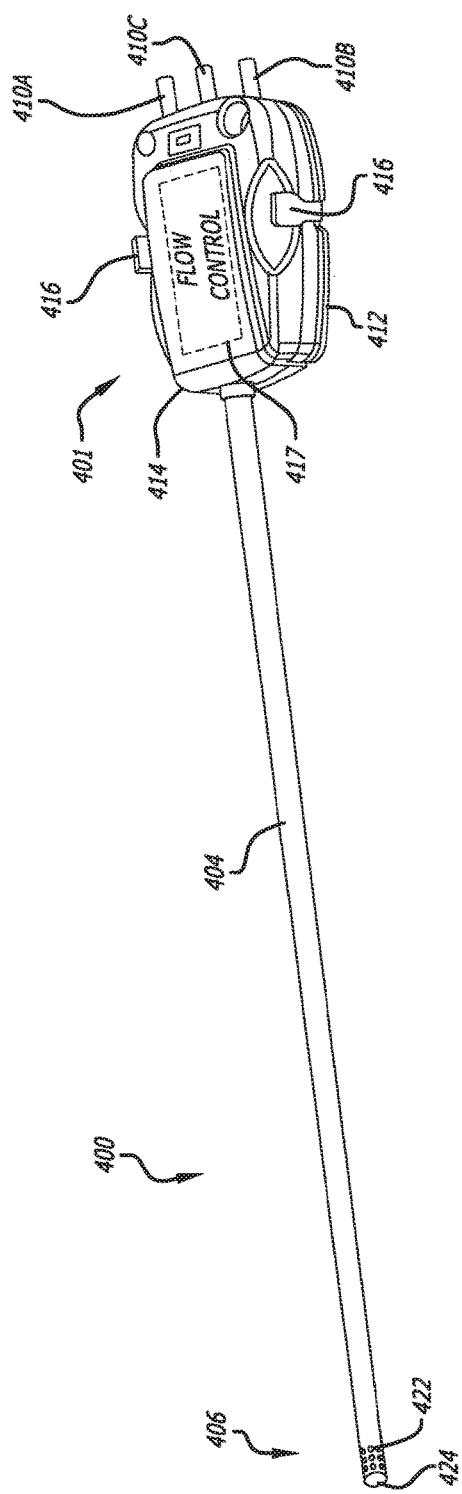
FIG. 4A is a perspective view of an irrigation/aspiration/blowing robotic surgical tool.

Referring to FIGS. 4A-4B, an irrigation/aspiration/blowing (IAB) robotic surgical tool or instrument 400 is illustrated in greater detail than that of instrument 101A. In one embodiment of the invention, the IAB robotic surgical instrument 400 has an interface that is backward compatible to the adapter 228 that is typically used for other types of robotic surgical instruments. In yet another embodiment of the invention, the IAB robotic surgical instrument 400 has a reusable instrument housing with modular valve components that are disposable. In yet another embodiment of the invention, the entire IAB robotic surgical instrument 400 is disposable.

The IAB robotic surgical instrument 400 includes a mountable housing 401 at a proximal end and a hollow tube 404 coupled together as shown in FIG. 4A. The mountable housing 401 may be a reusable housing including some reusable components therein. The mountable housing 401 is backward compatible and includes an interface base 412 that can couple to the adapter 228 to which other surgical tools may also couple. The mountable housing 401 may further include one or more tube fittings 410A-410C, a cover 414, and one or more release levers 416.

The hollow tube 404 is elongated and has an opening 424 at its tip 406, the distal end of the instrument 400. The hollow tube 404 may also be referred to as a hollow instrument shaft or a hollow probe. The hollow tube 404 may be reusable or disposable. The hollow tube 404 may be coupled to the interface base 412 for additional support. Alternative, the hollow tube 404 may couple directly to a modular disposable valve subassembly and avoid coupling to the interface base such that it too is disposable.

In one embodiment of the invention, the hollow tube 404 is a hollow circular cylindrical shape. Fluids (e.g., gas, liquid, with or without solids) may flow in the hollow tube 404 and into or out from a surgical site through the opening 424 at the tip 406. The hollow tube 404 may further include one or more smaller openings 422 around its circumference substantially near the tip 406 to further allow fluid to flow into and out of a surgical site. The diameter of the opening 424 may be substantially same as the inner diameter of the tube 404. In one embodiment of the invention, the diameter of the hollow tube 404 may be between 5 mm and 8 mm. The hollow tube 404 may be formed out of metal, plastic or other rigid material that can be hollow to allow fluid to flow therein while being positioned within a patient's body at a surgical site or over a surgical area.

The interface base 412 is used to mount the instrument 400 to a robotic arm of a surgical robotic manipulator. The interface base 412 both mechanically and electrically couples the IAB robotic surgical instrument 400 to a robotic arm of the surgical robotic manipulator 152. The release levers 416 are located at the sides of the mountable housing and may be used to release the robotic surgical instrument 400 from a robotic arm.

A first end of the one or more tube fittings 410A-410C may respectively couple to the one or more hoses 106A-106C, respectively. The one or more tube fittings 410A-410C may be barb fittings, luer fittings, or other types of hose or tube fittings. A second end of the one or more tube fittings 410A-410C couples to a flow control system 417 within the mountable housing 401. In some embodiments of the invention, the one or more hoses 106A-106C may directly couple to the flow control system without the one or more tube fittings 410A-410C. The end of the hollow tube 404 opposite the tip 406, also couples to the flow control system 417.

The flow control system 417 controls the flow of fluids, including any solids that may be transported by the fluid, between the surgical site and the one or more hoses 106A-106C through the IAB robotic surgical instrument 400. The flow control system 417 may include one or more valves of a valve subassembly to control the flow of fluids and any solids that may be transported by the fluid. Note that a fluid may be a liquid, a gas, a vacuum, or any combination thereof. The flow control system 417 may be controlled by control signals generated by an operator O at the master control console 150 to control the fluid flow through the IAB robotic surgical instrument 400. In addition to robotic control, a number of embodiments of the invention include an optional manual actuation of the valves of the IAB robotic surgical instrument 400. In which case, either an assistant A can manually operate the flow control system 417 and control the fluid flow or the operator O at the master control console 150 may robotically operate the flow control system 417 to control the fluid flow through the IAB robotic surgical instrument 400. The operator O at the master control console 150 can position the IAB robotic surgical instrument 400 where the operator wants it within the surgical site. Then, to free up the operator's hands to perform some other task at the master control console, the IAB robotic surgical instrument 400 may be controlled manually by an assistant, remaining attached to a robotic arm. The operator can then give verbal instructions to the assistant to manually control the irrigation/suction/blowing in the surgical site selected by the operator.

The cover 414 covers over to protect the flow control system 417 such as a valve subassembly from damage and to maintain a sterile surgical environment during surgery. As the surgical instrument 400 is used during an operation or surgery at a surgical site of human patient, it is important that its components be sterilized.

As body fluids of a human patient will be flowing through the surgical instrument 400 during use, it may be desirable to re-sterilize the IAB robotic surgical tool for reuse. However, it may be difficult to re-sterilize portions of the flow control system 417, such as valves, within the IAB robotic surgical tool 400. Thus, portions of the flow control system 417 may be replaced instead of sterilized after usage. If components forming the IAB robotic surgical instrument 400 are relatively inexpensive, the IAB robotic surgical instrument 400 may be discarded in its entirety instead of re-sterilizing or replacing components.

FIG. 4B illustrates a back side view of a portion of the IAB robotic surgical tool 400, some elements of which were previously discussed. In particular, the interface base 412 is illustrated with rotatable receiving elements 418 rotatably coupled thereto. The rotatable receiving elements 418 provide a mechanical coupling to the rotatable drivers 234 and drive motors mounted of the robotic surgical manipulator 152. Each of the rotatable receiving elements 418 include a pair of pins 422 extending from a surface thereof. An inner pin 422A is closer to an axis of rotation of each rotatable receiving elements 418 than an outer pin 422B, which helps to ensure positive angular alignment of the rotatable receiving elements 418. In one embodiment of the invention, the rotatable receiving elements 418 are disk shaped and may be referred to as rotatable disks.

The interface base 412 further includes an array of electrical connecting pins 424 and one or more integrated circuits 426 coupled to a printed circuit board 425 within the mountable housing 401. As the interface base 412 is backward compatible to the adapter 228, it may be mechanically actuated by pre-existing driver motors found in the robotic surgical manipulator 152. While the interface base 412 has been described herein with reference to mechanical and electrical coupling elements, it should be understood that other modalities may be used, including infrared coupling, magnetic coupling, inductive coupling, or the like.

Referring now to FIGS. 5A-5D, schematic flow diagrams of robotic surgical tools 500A-500D are respectively illustrated to provide irrigation, suction, blowing, or any combination thereof within a surgical site.

FIG. 5A is a schematic flow diagram of an irrigation/aspiration robotic surgical tool 500A that uses a pair of valves mounted within a housing 501A. The tool 500A includes the hollow tube 504, a valve subassembly 506, a three-way coupler 508, and tube fittings 509A-509B. The tube fittings 509A-509B may have an irrigation hose 106A and a suction hose 106B respectively coupled thereto.

The valve subassembly 506 includes a first two-way two-position valve 510A and a second two-way two-position valve 510B. After use, the valve subassembly 506 may be removed and replaced by a new sterilized valve subassembly for reuse of the tool 500A. The valves are a component of the tool that is more difficult to clean and sterilize for reuse.

Each of the two way valves 510A-510B includes two ports. A first port couples to the three-way coupler 508 while a second port couples to the fittings 509A or 509B, respectively. A three-way coupler 508 includes three ports one of which is coupled to the hollow tube 504. The second port of the three-way coupler couples to a port of the valve 510A. A third port of the three-way coupler 508 couples to a port of the valve 510B.

A fluid may flow in or out of the hollow tube 504 as illustrated by the double-headed arrow near the tip. Either valve 510A or 510B may be open so that a fluid may flow through the hollow tube 504. With valve 510B open and valve 510A substantially closed, a suction may be applied near the tip of the surgical instrument 500A so that a surgical site may be aspirated. With valve 510B substantially closed and valve 510A open, a liquid may flow through the surgical instrument 500A out through the hollow tube 504 into a surgical site so that it may be irrigated. The liquid is coupled to the surgical instrument 500A by the hose 106A.

FIG. 5B is a schematic flow diagram of an irrigation/aspiration robotic surgical tool 500B that uses a single valve mounted within a housing 501B to provide irrigation, or aspiration. The surgical instrument 500B includes a single three-way valve 516 with three ports, the hollow tube 504, and the tube fittings 509A-509B. The three way coupler 508 is not needed.

The three-way valve 516 has three ports. A first port of the three-way valve couples to the proximal end of the hollow tube 504. A second port couples to the tube fitting 509A that may couple to the hose 106A. A third port of the valve 516 couples to the tube fitting 509B that may in turn couple to hose 106B.

The three-way valve 516 has three-positions of operation. In a closed position, the valve is completely shut off so that no fluid flows through the hollow tube 504. In a second position suction is shut off, the first port and the second port of the valve couple together such that the surgical site may be irrigated by a liquid flowing through valve 516 and into the hollow tube 504. In a third position irrigation is shut off, the first port and the third port of the valve couple together such that a vacuum or a suction may flow through valve 516 and a surgical site may be aspirated at the tip of the hollow tube 504.

FIG. 5C is a schematic flow diagram of an irrigation/aspiration/blowing robotic surgical tool 500C that uses a single valve mounted within a housing 501C to provide irrigation, aspiration or blowing. The surgical instrument 500C includes a single four-way four position valve 526, the hollow tube 504, and the tube fittings 509A-509B coupled together as illustrated in the mountable housing 501C. A four way coupler 508 is not needed.

The single four-way valve 526 includes four ports. A first port of the four-way valve 526 couples to the proximal end of the hollow tube 504. A second port of the valve 526 couples to one end of the tube fitting 509A. A third port of the valve 526 couples to an end of the tube fitting 509B. A fourth port of the valve 526 couples to an end of the tube fitting 509C. Hoses 106A-106C may respectively couple to the tube fittings 509A-509C. In this manner three of the four ports of valve 526 may receive a liquid for irrigation, a vacuum for suction and a pressurized gas for blowing, respectively.

The four-way valve 526 has four positions of operation. In a closed position, the valve is completely shut off so that no fluid flows through the hollow tube 504. In a second position suction/blowing are shut off, the first port and the second port of the valve couple together such that the surgical site may be irrigated by a liquid flowing through valve 526 and into the hollow tube 504. In a third position irrigation/suction are shut off, the first port and the third port of the valve couple together such that a pressurized gas may flow through valve 516 and out through the tip of the hollow tube 504 to blow a surgical site with a pressurized gas. In a fourth position irrigation/blowing are shut off, the first port and the fourth port of the valve couple together such that a vacuum may provide suction through the valve 516 and the hollow tube 504 to a surgical site to remove fluids and solids transported therein at the tip of the hollow tube 504.

FIG. 5D is a schematic flow diagram of an irrigation/aspiration/blowing robotic surgical tool 500D that uses three two-way valves in a valve subassembly mounted within a housing 501D to provide irrigation, aspiration or blowing.

The robotic surgical instrument 500D includes a valve subassembly 536, a four-way coupler 538, the hollow tube 504, and the tube fittings 509A-509C. The tube fittings 509A-509C may couple to the hoses 106A-106C, respectively.

In place of the four-way valve 526 illustrated in FIG. 5C, the valve subassembly 536 includes three two-way two-position valves 510A-510C of a valve subassembly 536 in conjunction with a four-way coupler 538. In comparison with the tool 500A of FIG. 5A, a third two-way valve 510C is provided so that a third fluid may flow into and out of the hollow tube 504. In this case, a pressurized gas may be supplied by hose 106C, flow through valve 510C when opened, flow through the four way coupler 538, and into the hollow tube 504 to blow a pressurized gas near the surgical site.

Each of the two way two position valves 510A-510C includes two ports. A first port of each couples to respective ports of the four-way coupler 538 while a second port of each couples to the fittings 509A, 509B or 509C, respectively. The four-way coupler 538 includes four ports one of which is coupled to the hollow tube 504. The second port of the four-way coupler 538 couples to a port of the valve 510A. A third port of the four-way coupler 538 couples to a port of the valve 510B. A fourth port of the four-way coupler 538 couples to a port of the valve 510C.

Valve subassembly 536 may be replaceable with a sterile component while the other elements mounted in the housing 501D may be separately sterilized and reused with a new valve subassembly 536.

Various types of valves may be used as part of the flow control system 417 in the IAB robotic surgical instrument 400, 101A to control the flow of fluids to provide irrigation, aspiration, or blowing. For example, a linear motion type of valve ("linear valve") may be used such as a spool-type valve, a trumpet-type valve, a piston-type valve, a poppet-type valve, or a sliding-plate-type valve. Alternatively, a rotational motion type of valve ("rotatable valve") may be used such as a ball-type valve, a screw-type valve, a gate-type valve, a disc-type valve, a cock-type valve, a globe-type valve, or a rotary-plate-type valve. Additionally, the various types of valves within the IAB robotic surgical instrument may be actuated in different ways by the robotic surgical manipulator 152. While three-way and two-way valves have been separately shown and described, any mixed combination of one or more two-way valves and one or more three-way valves, or other multi-port valve, may be used within an IAB robotic surgical instrument with different types of couplers to provide a flow control system therein. For example, an IAB robotic surgical instrument may include a three-way valve 516 for gas pressure and suction and a two-way valve 510A for irrigation by a liquid coupled to a three-way coupler 508, which is in turn coupled to the tube 504.

Moreover, the valves used in the flow control system may be automatically returned to a closed position so that no fluid flows through the IAB robotic surgical tool when it is dismounted from the robotic arm or when the modular valve assembly is not mounted in the housing of the tool. That is, the valves may be spring loaded by a spring to return to a closed or fully off position when they are not actuated.

FIGS. 6A-6C, 7A-7C, 8, 9 and 10A-10B illustrate some of the various types of valves, various types of actuation means, and various types of automatic return means that may be used to control the flow of fluids through the robotic surgical instrument and into the surgical site. It is understood that other types of valves, actuation means, and automatic return means may be used to provide flow control for a flow control system of an IAB robotic surgical tool.

Referring now to FIGS. 6A-6C, rotational actuators to actuate rotatable valves are illustrated for use with the irrigation/aspiration/blowing robotic surgical tool and the robotic surgical arm.

In FIG. 6A, the rotatable receiving element 418A is directly coupled to the rotatable valve 604A. As the rotatable receiving element 418A is rotated, a shaft of the rotatable valve rotates to a different position in order to open or close the valve and control the flow of fluids. For actuation, the rotatable receiving element 418A couples to the rotatable driver 234 of the adapter 228 in the robotic arm. The pins 422A-422B of the rotatable receiving element 418A couple into the respective openings 240A-240B of the adapter 228. A coil spring 606 may be used to return the rotatable valve 604A to a closed or shut off position when the robotic surgical tool 101A is dismounted from the robotic arm.

In FIG. 6B, a rotatable receiving element 418B rotatably couples to the rotatable valve 604B through a gearing provided by the gears 610-611. The rotatable receiving element 418B similarly couples to the rotatable driver 234. The rotatable receiving element 418B includes the gear 610 which also may be referred to as a driving gear 610. Valve 604B includes the pinion gear 611 coupled to a shaft 602 of the rotatable valve in order to rotate the valve from one position to another. The gearing may be use to reduce or increase the rotation in the driver gear 610 to rotate the valve. The rotatable receiving element 418B may further include the coil spring 606 to return the three-way four position valve 604B to a shut off position. The rotatable valve 604B is a three-way valve including three ports and has three positions.

In FIG. 6C, the rotatable receiving element 418C is linked to the rotatable valve 604C by means of a linkage 620. The rotatable receiving element 418C includes a drive wheel with a notch 622 to receive a distal end of the linkage 620. The rotatable valve 604C is a three-way three position valve. The rotatable receiving element 418C may move the valve 604C into one of three positions. In position 620A, the valve may be shut off so that no fluid flows through the robotic surgical tool 101A, 400. In position 620B, a first fluid may flow between a first port and a second port. In position 620C, a second fluid may flow between the first port and a third port.

To change positions of the valve using the linkage 620, the rotatable receiving element 418C may be moved counter clockwise, while the valve rotates clockwise. If the rotatable receiving element 418C moves clockwise, the linkage 620 causes the valve to rotate counter clockwise. To actuate the rotatable valve, the rotatable receiving element 418C couples to the rotatable driver 234 by means of the pins 422A-422B coupling into the opening 240A-240B respectively.

Figure 7A:
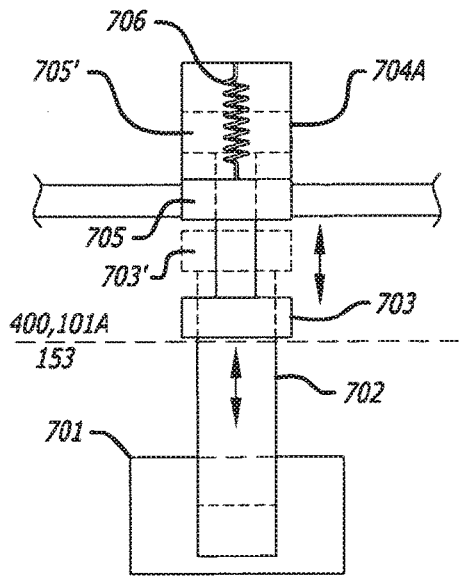
FIGS. 7A-7C are cross-sections of linearly actuated linear valves for use with the irrigation/aspiration/blowing robotic surgical tool and the robotic surgical arm.
Figure 7B:
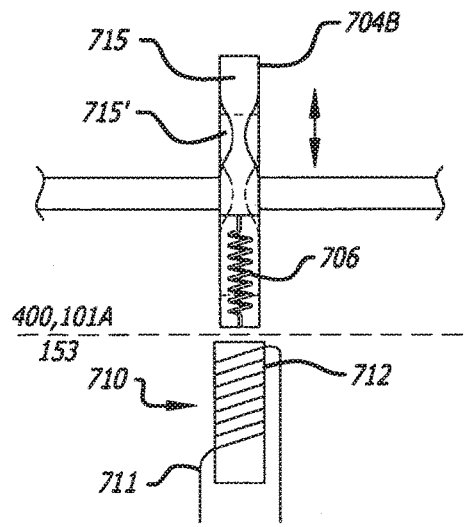
Figure 7C:
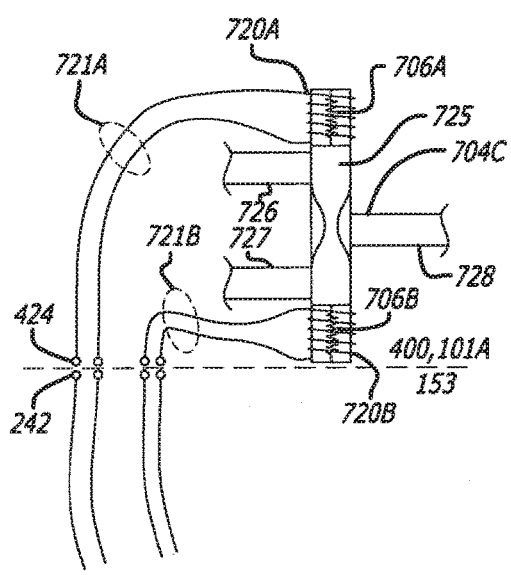

FIGS. 7A-7C illustrate the linear actuation of linear motion valves that may be used in the flow control system 417 of IAB robotic surgical tools. The dashed lines shown in FIGS. 7A-7C illustrate a dividing line between the robotic surgical tool 400, 101A and actuation in the robotic surgical arm 153.

In FIG. 7A, a push rod 702 is linearly actuated in the robotic arm 153. One end of the push rod 702 pushes on a button 703 of a linear motion trumpet valve 704A to move a plunger 705 therein. The trumpet valve 704A is a two-way two-position valve. The plunger 705 in its closed position blocks the first and second ports of the trumpet valve 704A. When the valve is linearly pushed open, a spring 706 is compressed and the plunger moves to a position 705' such that the first and second ports are open to pass a fluid.

The push rod 702 may be linearly actuated in robotic arm in a number of ways including, but not limited to, pneumatically, hydraulically, electromechanically, or electrically. For example, a solenoid 701 may be used to linearly actuate the push rod 702 to linearly move the valve 704A to an open position. When the push rod 702 is not actuated, the force of the spring 706 may push back on the push rod 702 and return the plunger of the valve to a closed plunger position 705 to shut off the first and second ports and stop a flow of a fluid. The spring 706 may also retain the plunger of the valve in a closed plunger position 705 to shut off the first and second ports when the IAB robotic surgical tool is dismounted.

In FIG. 7B, a spool valve 704B linearly moves in response to a magnetic force generated by the electromagnet 710 in the robotic arm 153. The electromagnet 710 may be formed out of coil of wire 711 wrapped around a magnetic core 712. When no electromagnetic field is generated by the electromagnet 710, a spring 706 keeps the spool 715 in a closed position blocking the first and second ports of the spool valve 704B. To actuate the spool valve, the electromagnet 710 is actuated to pull the spool 715 in a linear motion into position 715' so that the center hourglass portion of the spool 715 is coincident with the first and second ports to allow fluid to flow through the valve 704B. Spring 706 is compressed with the spool in position 715' such that when the electromagnetic force of the electromagnet 710 is released the spring 706 pushes back on the spool 715 to close off the valve 704B.

In FIG. 7C, a three-way spool valve 704C is electrically actuated by the robotic arm 153 to move the spool 725 with a linear motion. Electrical contacts 242 in the robotic arm 153 couple to the pins 424 of the robotic surgical tool 400, 101A. The three-way valve 704C includes the spool 725, three ports, a first spring 706A at a first end, and a second spring 706B at a second end, a first wire coil 710A at the first end, and a second wire coil 710B at the second end. A current in the wires 721A may flow through the coil 710A to attract the spool 725 towards the first end of the valve so that the ports 726 and 728 of the valve are coincident with the center hourglass portion of the spool to allow fluid to flow there-between. To shut off the valve, the current flow in the wires 721A is turned off and the spool 725 is pushed back into the closed position by the force of spring 706A. Springs 706A-706B maintain the spool in the center position shutting off the three ports in the valve from each other. By providing a current in the wires 721B and the coil 720B, the spool 725 is moved towards the second end and compresses the spring 706B. This allows the center hourglass portion of the spool 725 to coincide with the second port 727 and the third port 728 to allow a fluid to flow there-between. To shut off the valve, the current flow in the wires 721B is turned off and the spring 706B pushes the spool 725 back to its closed position.

Figure 8:
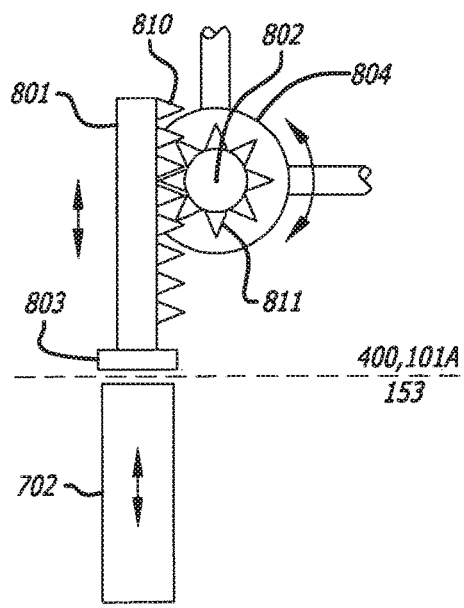
FIG. 8 is a top view of exemplary linear actuation of a rotatable valve for use with the irrigation/aspiration/blowing robotic surgical tool and the robotic surgical arm.

Referring now to FIG. 8, a linear actuation is transformed into a rotational actuation for a rotatable valve by a rack and pinion gear system. When activated, a push rod 702 linearly pushes against a button 803 of the rack 801 in order to linearly move its teeth 810 and provide the initial linear actuation. The teeth 810 of the rack 801 are meshed with the pinion gear 811 to transform the initial linear actuation of the push rod into a rotational actuation. The pinion gear is coupled to a shaft 802 of the rotatable valve 804. As the teeth of the rack 801 linearly move, the pinion gear 811 transforms the linear motion into a rotational motion in order to rotate the rotatable valve 804 between open and closed positions to control the fluid flow.

A spring may be coupled between an end of the rack 801 and a stop in order to linearly push on the rack and rotate and maintain the valve in a closed position when the IAB robotic surgical tool is dismounted.

In addition to being robotically controlled from the master control console 150, the valves of the flow control system 417 of the IAB robotic surgical tools may also be manually controlled. Manual actuators may be provided that extend external to the housing so that a user's hand may open and/or close the valves.

Figure 9A:
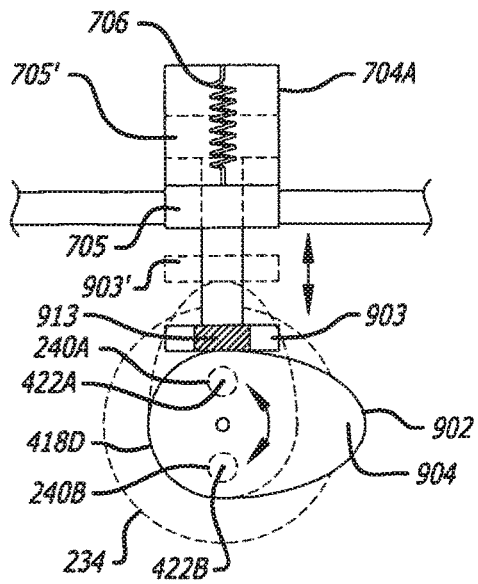
FIG. 9A is a top view of exemplary rotational actuation of a linear valve for use with the irrigation/aspiration/blowing robotic surgical tool and the robotic surgical arm with an optional manual push arm.
Figure 9B:
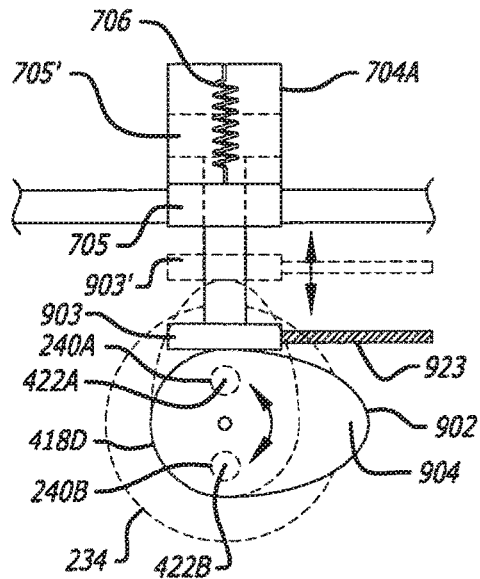
FIG. 9B is a top view of exemplary rotational actuation of a linear valve for use with the irrigation/aspiration/blowing robotic surgical tool and the robotic surgical arm with an optional manual push side-arm.

Referring now to FIGS. 9A-9B, a rotational actuation is transformed into linear actuation by a cam and cam follower system for actuation of a linear motion trumpet valve 704A. Trumpet valve 704A illustrated in FIGS. 9A-9B operates similarly to trumpet valve 704A of FIG. 7A but with a cam follower 903 in place of the button 703 to better couple to the rotating cam 902. Additionally, the cam follower 903 of FIG. 9A may further include a manual push arm 913 that may extend for a top side of a housing of the IAB robotic surgical tools for manual operation of the trumpet valve 704A. The cam follower 903 of FIG. 9B may further include a manual push side arm 923 that may extend for a side of a housing of the IAB robotic surgical tools for manual operation of the trumpet valve 704A.

The rotatable receiving element 418D of the IAB robotic surgical tools is coupled to the cam 902. For robotic control from the master control console 150, the rotatable receiving element 418D couples to the rotatable driver 234 by means of the pins 422A-422B within the openings 240A-240B, respectively.

The cam 902 includes a cam lobe 904 that pushes on the cam follower 903 to a position 903' so that the plunger 705 is moved to an open position 705'. In the open position 705', the plunger allows the first and second ports to couple together and allow a fluid to flow there-between. As the cam rotates to move the cam lobe to a different position so that the cam follower can move back to its original position 903, the spring 706 pushes on the plunger 705 to move it back into the closed position to close the valve 704A.

The cam 902 may rotate clockwise or counterclockwise so that the cam follower transforms a rotational motion into a linear motion to open and close the valve 704A. In this manner, a rotational actuation within the robotic surgical tool 400, 101A may be converted to linear actuation and actuate a linear motion valve, such as the trumpet valve 704A. A coil spring may be coupled around the shaft of the cam 901 in order to rotate it so that the valve can close when the IAB robotic surgical tool is dismounted.

With the cam 902 rotated to a position so that the valve 704A is closed, the valve may be manually operated. To manually operate valve 704A, a user pushes on the manual push arms 913, 923 extending from the housing. With the manual push arms 913, 923 being coupled to the cam follower 903, the force applied thereto manually forces open the valve 704A. This decouples the cam follower 903 from the cam 902. To close the valve 704A, a user releases the force applied to the manual push arms 913, 923 which allows the spring 706 to push back out the plunger 705 into a closed position and shut off the valve.

Figure 10A:
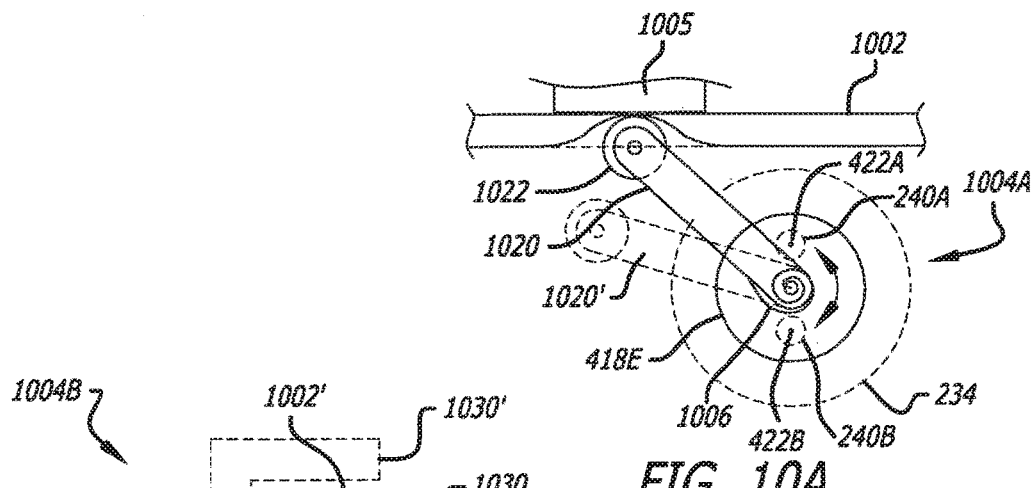
FIG. 10A is a top view to illustrate rotational actuation of a rotatable pinch valve for use with the irrigation/aspiration/blowing robotic surgical tool and the robotic surgical arm.
Figure 10B:
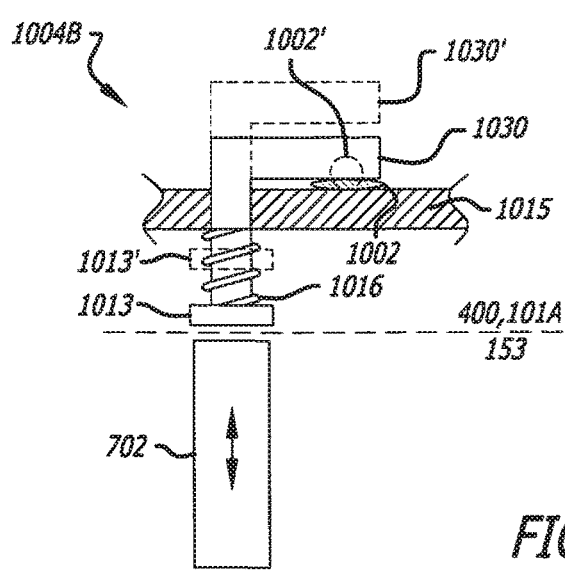
FIG. 10B is a side view to illustrate linear actuation of a linear pinch valve for use with the irrigation/aspiration/blowing robotic surgical tool and the robotic surgical arm.

Referring now to FIGS. 10A-10B, pinch valves 1004A-1004B for use in the flow control system of IAB robotic surgical tools are illustrated. The pinch valves 1004A-1004B are used to pinch closed a hose 1002, 1002' to control the flow of fluids.

In FIG. 10A, a rotary pinch valve 1004A is illustrated to pinch closed a hose 1002 and can be rotated to release and open the hose 1002. Without the hose 1002 pinched off, a fluid is allowed to flow therein and through the IAB robotic surgical tools. The rotary pinch valve 1004A pinches the hose 1002 closed against a backstop 1005 to shut off the flow of fluids. The hose 1002 may be a silicon rubber hose that is flexible in order that it may be readily pinched off and stop the fluid flow therein and flex back when released.

The rotary pinch valve 1004A is coupled to a shaft of the rotatable receiving element 418E to receive a rotational actuation. The rotatable receiving element 418E may couple to the rotatable driver 234 in a similar fashion as previously described with pins 422A-422B inserted into the respective openings 240A-240B.

The rotary pinch valve 1004A includes a rotatable pinch arm 1020 and a pinch roller 1022 coupled to the distal end of the rotatable pinch arm 1020. The rotary pinch valve 1004A may further include a spring 1006 coupled to the rotatable receiving element 418E in order to bias the pinch valve to a closed position and pinch off the hose when the surgical tool 101A. 400 is dismounted.

In the closed position, the pinch roller 1022 pinches off the hose 1002 against the backstop 1005. In rotating the pinch valve 1004A and the rotatable pinch arm from the closed position to a position 1020', the pressure against the hose 1002 is released such that it flexes open and allows fluid to flow therein.

In FIG. 10B, a linear pinch valve 1004B is illustrated to pinch closed a hose 1002'. The linear pinch valve 1004B can be moved linearly to release and open the hose 1002'. Without the hose 1002' pinched off, a fluid is allowed to flow therein and through the IAB robotic surgical tools. The linear pinch valve 1004B pinches the hose 1002' closed against a backstop 1015 to shut off the flow of fluids. The hose 1002' may be a silicon rubber hose that is flexible in order that it may be readily pinched off and stop the fluid flow therein and flex back when released.

A push rod 702 may be provided in the robotic arm 153 to provide linear actuation of the linear pinch valve 1004B. The push rod 702 pushes on a button 1013 to a position 1013'', compressing a spring 1016, and linearly moving the linear pinch valve 1004B and a linear pinch arm 1030 to position 1030' to release the hose 1002 from the backstop 1015. With the linear pinch arm 1030 in the open position 1030', the linear pinch valve is open and fluid can flow within the hose 1002'. Upon releasing the linear force provided by the push rod 702 within the robotic arm 153, the spring 1016 forces back the linear pinch arm 1030 of the linear pinch valve 1030 to squeeze the hose 1002 against the backstop 1015. In this manner, a linear actuating motion of the push rod 702 can activate a linear pinch valve 1004B.

FIGS. 11A-15B illustrate exemplary embodiments of IAB robotic surgical tools including varying types of flow control systems.

Referring now to FIGS. 11A-11E, irrigation/aspiration/blowing robotic surgical tools having a flow control system with a solid valve body are now discussed.

Figure 11A:
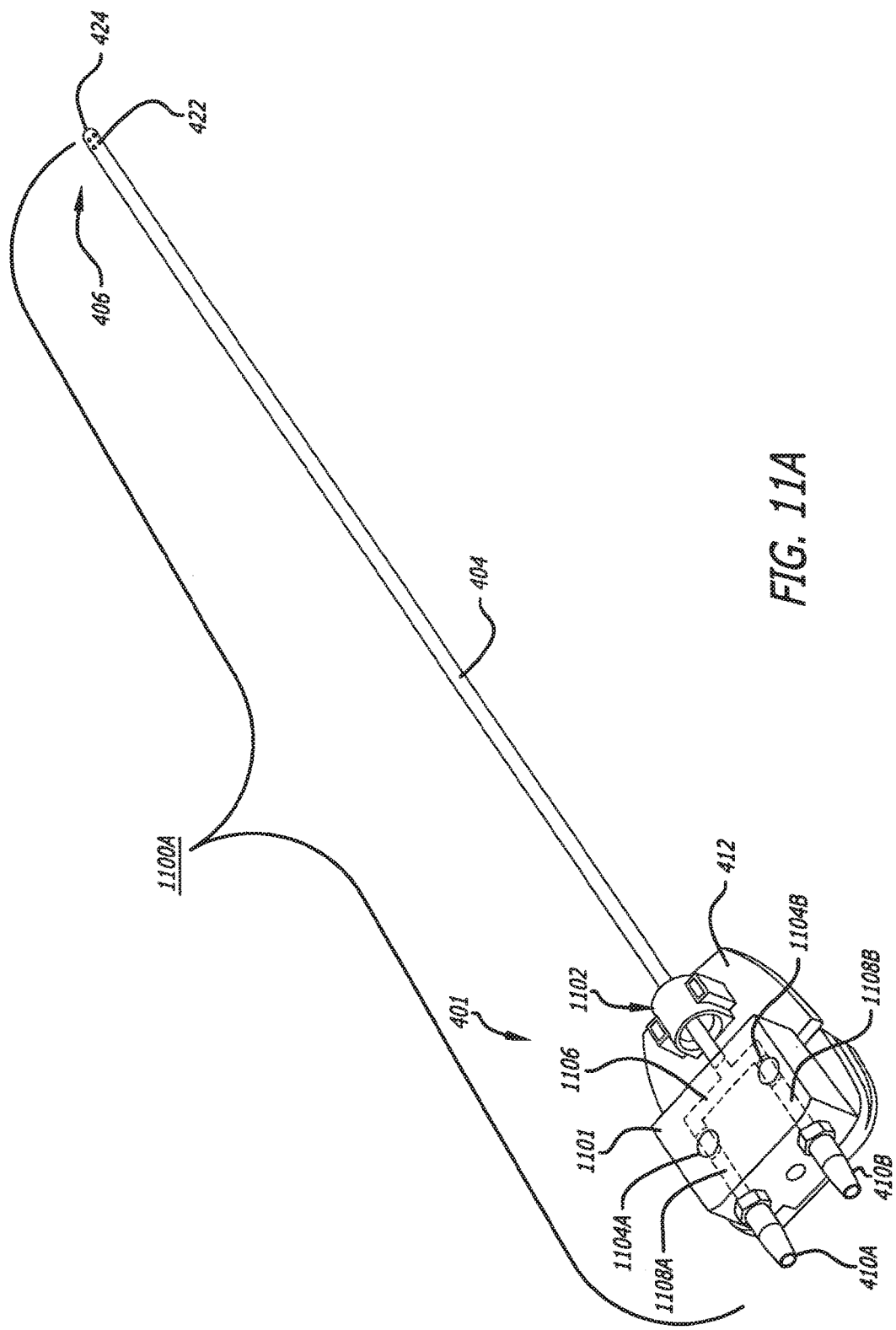
FIG. 11A is a top perspective view of an irrigation/aspiration/blowing robotic surgical tool with cover removed to show a solid valve body.

FIG. 11A illustrates a top perspective view of an IAB robotic surgical tool 1100A with its cover removed to show the flow control system 417 therein. The IAB robotic surgical tool 1100A employs a solid valve body 1101. The solid valve body 1101 is a three-dimensional solid body that includes hollow passages with open ports therein and a pair of valve openings to receive a pair of rotatable valves 1104A-1104B. In one embodiment of the invention, the solid valve body 1101 is a polyhedron shaped solid body.

With a solid valve body, the flow control system 417 of the IAB robotic surgical tool 1100A is relatively inexpensive to manufacture such that the flow control system 417 may be discarded after use, instead of cleaned or sterilized. The remaining components of the tool 1100A may be cleaned and re-sterilized. Alternatively, the IAB robotic surgical tool 1100A is also relatively inexpensive to manufacture such that it may be discarded in its entirety after usage.

A first port of the solid valve body 1101 couples to the proximal end of the hollow tube 404. Second and third ports of the solid valve body 1101 may couple to the hose fittings 410A-410B. The hose fittings 410A-410B may respectively couple to hoses 106A-106B. The solid valve body 1101 includes a three-way passage 1106 coupled between the proximal end of the hollow tube 404 and first ports of rotatable valves 1104A-1104B. The solid valve body 1101 further includes passages 1108A-1108B coupled between second ports of the rotatable valves 1104A-1104B and the hose fittings 410A-410B, respectively. The rotatable valves 1104A-1104B are two-way two-position valves and each have an open flow channel that can be rotated and switched open or closed between the ports to the respective passages 1108A-1108B and the ports to the three-way passage 1106.

Although a third valve and a third set of passages are not illustrated in FIG. 11A, it is understood that it may be provided to provide flow control for a third type of fluid.

The hollow tube 404 is mechanically supported in the mountable housing by having an end coupled into the first port of the solid valve body 1101. The hollow tube 404 may be further supported mechanically by being inserted into a bushing that is supported within the collar 1102 of the interface base 412. As previously discussed, the hollow tube 404 has an opening 424 at its tip 406. The hollow tube 404 may further have openings around its circumference near its tip 406.

The solid valve body 1101 may be fitted to the interface base 412 so that it is readily replaceable. The hollow tube 404 may be fitted with a quick release fitting to the solid valve body 1101 so that it can be readily re-sterilized and reused.

Figure 11B:
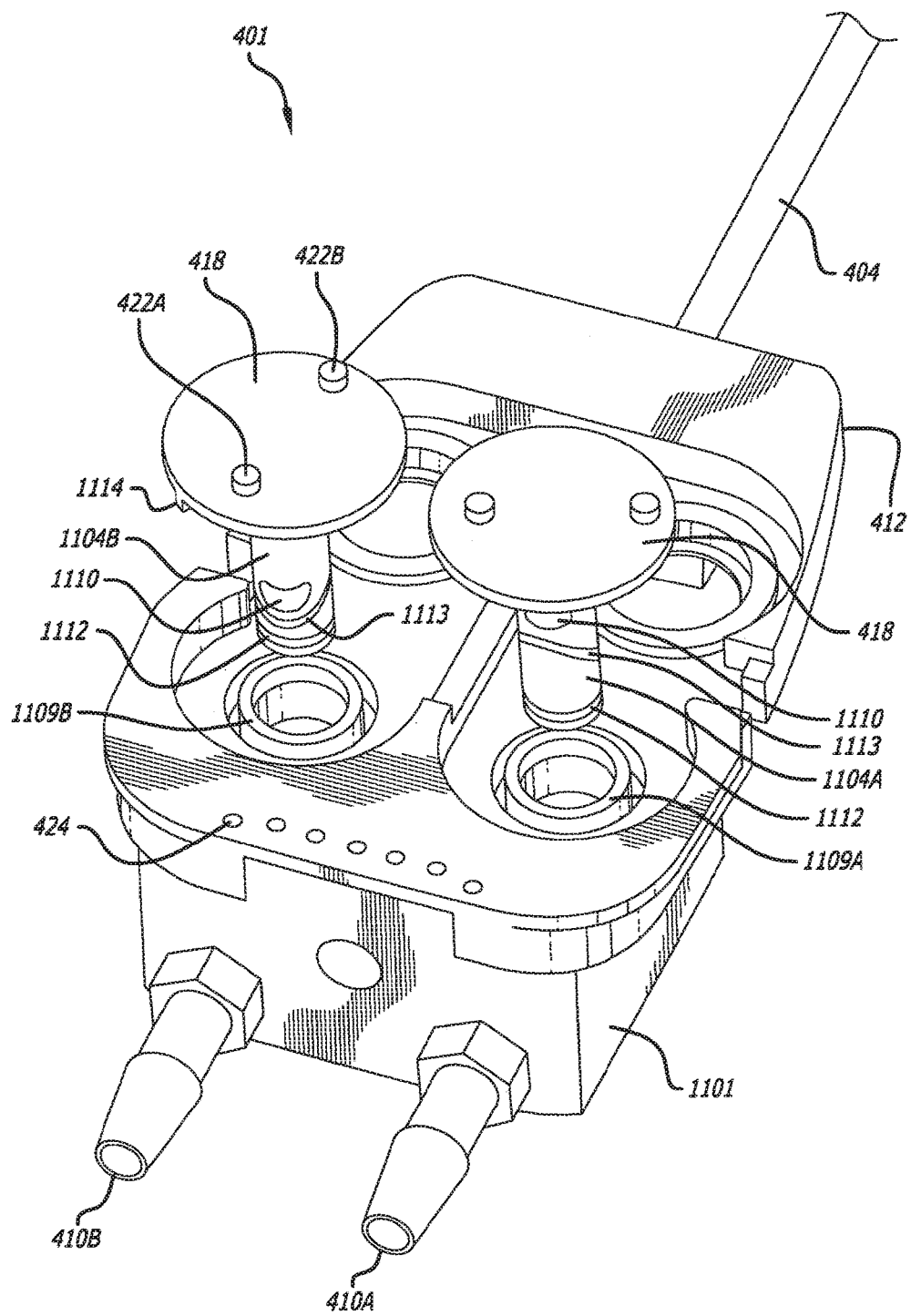
FIG. 11B is a bottom exploded of the irrigation/aspiration/blowing robotic surgical tool of FIG. 11A with the solid valve body.

Referring now to FIG. 11B, a bottom exploded view of the IAB robotic surgical tool 1100A is illustrated. As illustrated by FIG. 11B, the solid valve body 1101 includes valve openings 1109A-1109B to receive the rotatable valves 1104A-1104B, respectively. The valve openings 1109A-1109B in the solid valve body may include threads or rings to allow the rotatable valves 1104A-1104B to rotate in a fixed axial position with respect to the passages 1106, and 1108A-1108B.

Coupled to one end of a cylindrical shaft 1105 of each of the rotatable valves 1104A-1104B is a rotatable receiving element 418 with pins 422A-422B. The rotatable receiving element 418 of the rotatable valves 1104A-1104B may further include a tab 1114 to abut against a stop within the interface base 412.

Elements of the rotatable valves 1104A-1104B may be molded together as one piece to further lower the cost of manufacture of the flow control system. As valves 1104A-1104B are substantially similar, a further detailed description of valve 1104A is only provided with valves 1104A-1104B being collectively referred to as valves 1104.

In the cylindrical shaft 1105 of the valves 1104 is the flow channel 1110. The flow channel 1110 of the rotatable valves 1104 may be a slanted opening through the cylindrical shaft. The flow channel 1110 of the rotatable valves 1104 may be a slanted opening through the cylindrical shaft. Wrapped around the cylindrical shaft are one or more seals 1112 to seal off the flow channel 1110 within the valve body 1101. A slanted seal 1113 may be provided above the slanted opening of the flow channel 1110. In an alternate embodiment of the invention, an additional slanted seal 1113 may be provided below the slanted opening of the flow channel 1110. The cylindrical shaft 1105 has circumferential channels to respectively receive a portion of the one or more seals 1112. The cylindrical shaft 1105 has one or more slanted channels in its cylindrical surface to respectively receive a portion of the one or more slanted seals 1113. The channels in the shaft 1105 keep the seals in position as the valve is moved.

Figure 11C:
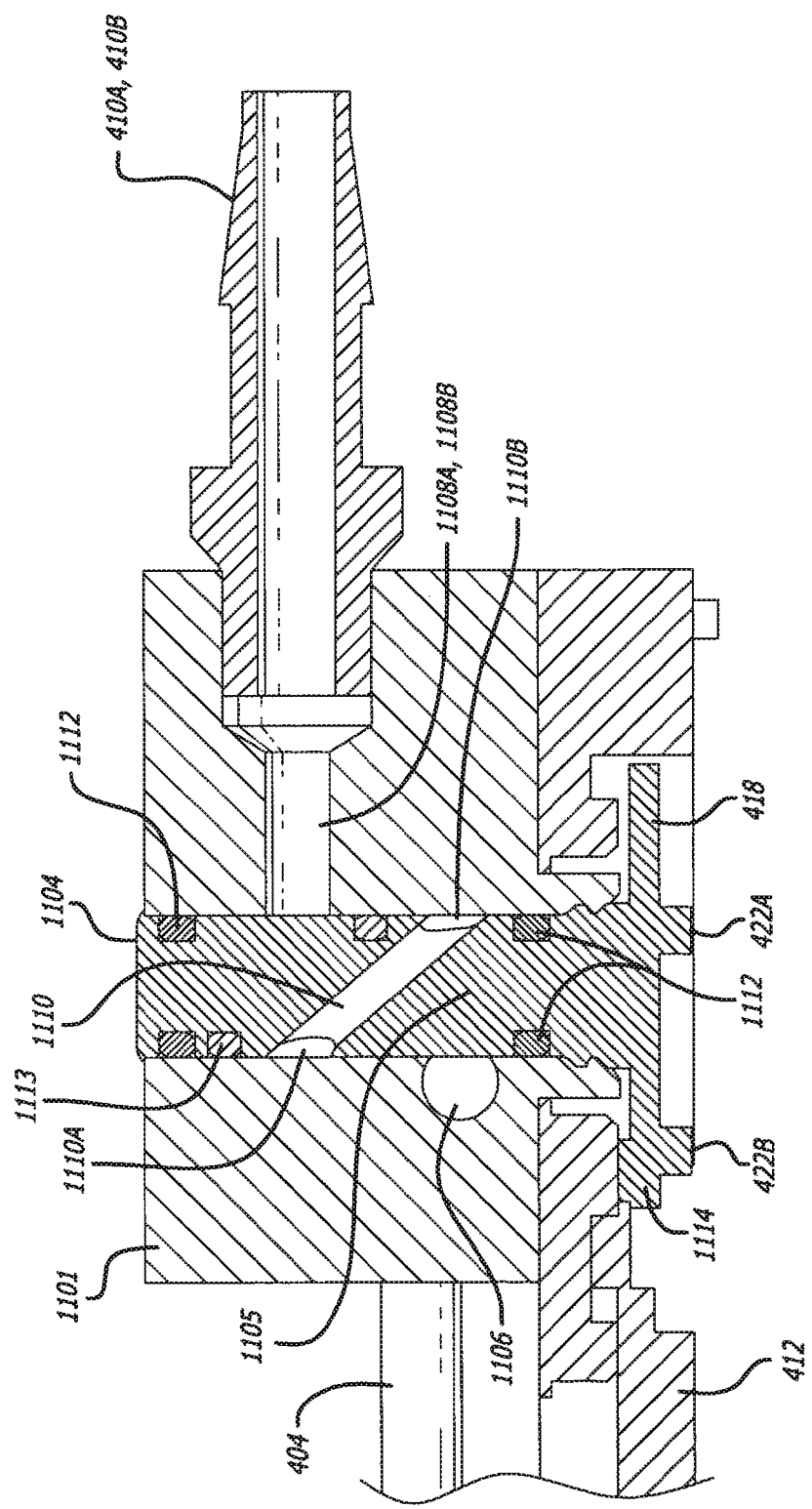
FIG. 11C is a cross sectional view of the valve assembly with the solid valve body in a closed position for the irrigation/aspiration/blowing robotic surgical tool of FIG. 11A.

Referring now to FIG. 11C, a cross section of one of the rotatable valves 1104 is illustrated in a closed position. As discussed previously, the rotatable valve 1104 includes the cylindrical shaft 1105 coupled at one end to the rotatable receiving element 418.

The cylindrical shaft 1105 includes the flow channel 1110. The flow channel 1110 has a first port 1110A at one end and a second port 1110B at a second end. As discussed previously, the flow channel 1110 may be slanted from the first port 1110A to the second port 1110B. As valve 1104 is in a closed position in FIG. 11C, neither the first port 1110A nor the second port 1110B of the flow channel 1110 matches the ports into the passages 1106 or 1108A, 1108B. The cylindrical shaft 1105 further includes one or more seals 1112 near top and bottom portions to seal off the flow channel 1110 in the solid body 1101. The cylindrical shaft 1105 further includes the slanted seal 1113 between a top seal 1112 and the slanted flow channel 1110 to further seal the rotatable valve within the solid body 1101.

The slanted seal 1113 around the cylindrical shaft 1105 allows for relaxed tolerances between the rotatable valve 1104 and the solid valve body 1101. In particular, the slanted seal 1113 allows for a larger radial gap between the cylindrical shaft 1105 of the valve 1104 and the solid valve body 1101 while maintaining a leak-less seal. While the top and bottom seals 1112 seal the valve 1404 with respect to the valve body, the slanted seal 1113 seals the flow of fluids through the channel 1110. The slanted seal 1113 seals the flow of fluids through the channel 1110 over the range of positions of the valve 1104, from a fully closed position to a fully open position. The slanted seal 1113 particularly prevents leakage when the valve 1104 is in the closed position.

In an alternate embodiment of the invention, the channel 1110 in the cylindrical shaft 1105 is replaced by narrowing the center diameter portion of the cylindrical shaft 1105 between the slanted seal 1113 and the bottom seal 1112, such as into an hour glass shape, to form a channel for fluid flow when the valve 1104 is moved from a closed position. In this case, the slanted seal 1113 forms an end portion of the channel.

The hollow tube 404 couples to a port of the three-way passage 1106. The hose fittings 410A, 410B couple to the passages 1108A, 1108B, respectively. The hose fittings 410A, 410B and the hollow tube 404 may be press fitted into the solid valve body 1101 or have threads to be screwed into and mate with threads in passages 1106, 1108A, 1108B of the solid valve body 1101.

Figure 11D:
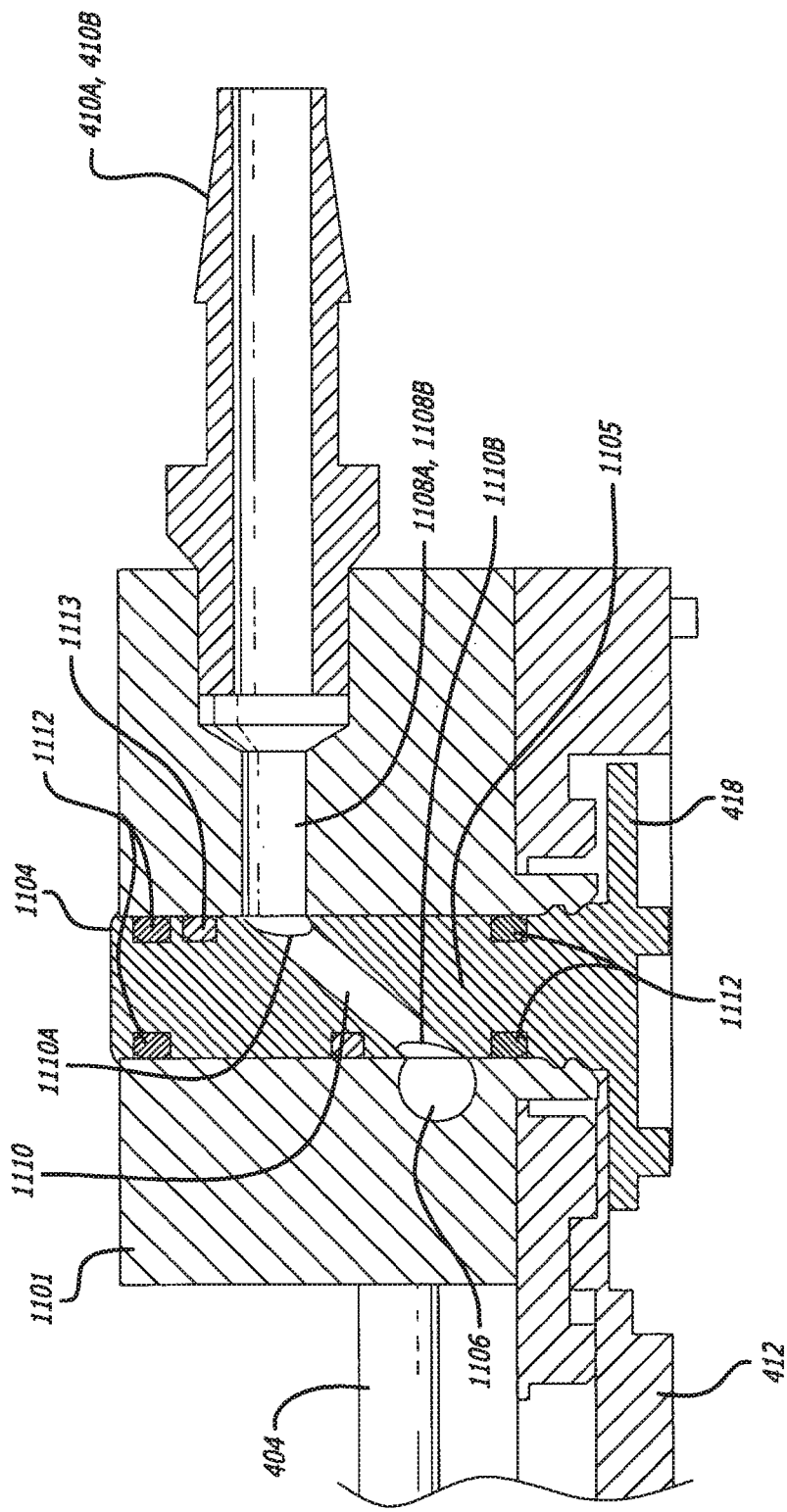
FIG. 11D is a cross sectional view of the valve assembly with the solid valve body in an open position for the irrigation/aspiration/blowing robotic surgical tool of FIG. 11A.

Referring now to FIG. 11D, a cross section of one of the rotatable valves 1104 is illustrated in an open position. With the rotatable valve 1104 in an open position, a fluid can flow between the hollow tube 404 and one of the hose fittings 410A, 410B by way of the passages in the solid valve body 1101 and the flow channel 1110.

In comparison with FIG. 11C, the flow channel 1110 in the cylindrical shaft 1105 is reoriented to a position where its first port 1110A matches a port of the three-way passage 1106 and its second port 1110B matches a port of the passage 1108A, 1108B. In this manner, a fluid can flow from the hollow tube into the three way passage 1106, through the flow channel 1110, into the passage 1108A, 1108B and out of the hose fitting 410A, 410B. Alternatively, a fluid can flow from the hose fitting 410A, 410B, into the passage 1108A, 1108B, through the flow channel 1110, into the three way passage 1106 and out from the hollow tube 404.

FIGS. 11C-11D illustrate one or more seals 1112 near top and bottom portions of the shaft 1105 and the slanted seal 1113 in parallel with the slanted flow channel 1110 to seal the rotatable valves 1004A-1104B in the solid body 1101.

The rotatable valves 1104A and 1104B may operate in the same rotational direction or in opposite rotational directions. That is, each rotatable valve may operate to open in a clockwise direction or a counterclockwise direction. Alternatively, rotatable valve 1104A may open using a counterclockwise rotation while rotatable valve 1104B opens using a clockwise rotation, for example.

With a solid valve body 1101 and one piece rotatable valves 1104, the flow control system 417 can be made relatively inexpensive such that it can be readily discarded with or without other components of the surgical tool 1100A.

As discussed previously, the valves of the flow control system 417 of the IAB robotic surgical tools may also be manually controlled with manual actuators. Additional manually controlled valves may also be provided in parallel with robotically controlled valves in the flow control system in order to both manually and robotically control the fluid flows through an IAB robotic surgical instrument. Manual actuators are coupled to the manually controlled valves to extend external to the housing of the IAB robotic surgical tools so that a user's hand may open and/or close the valves.

Figure 11E:
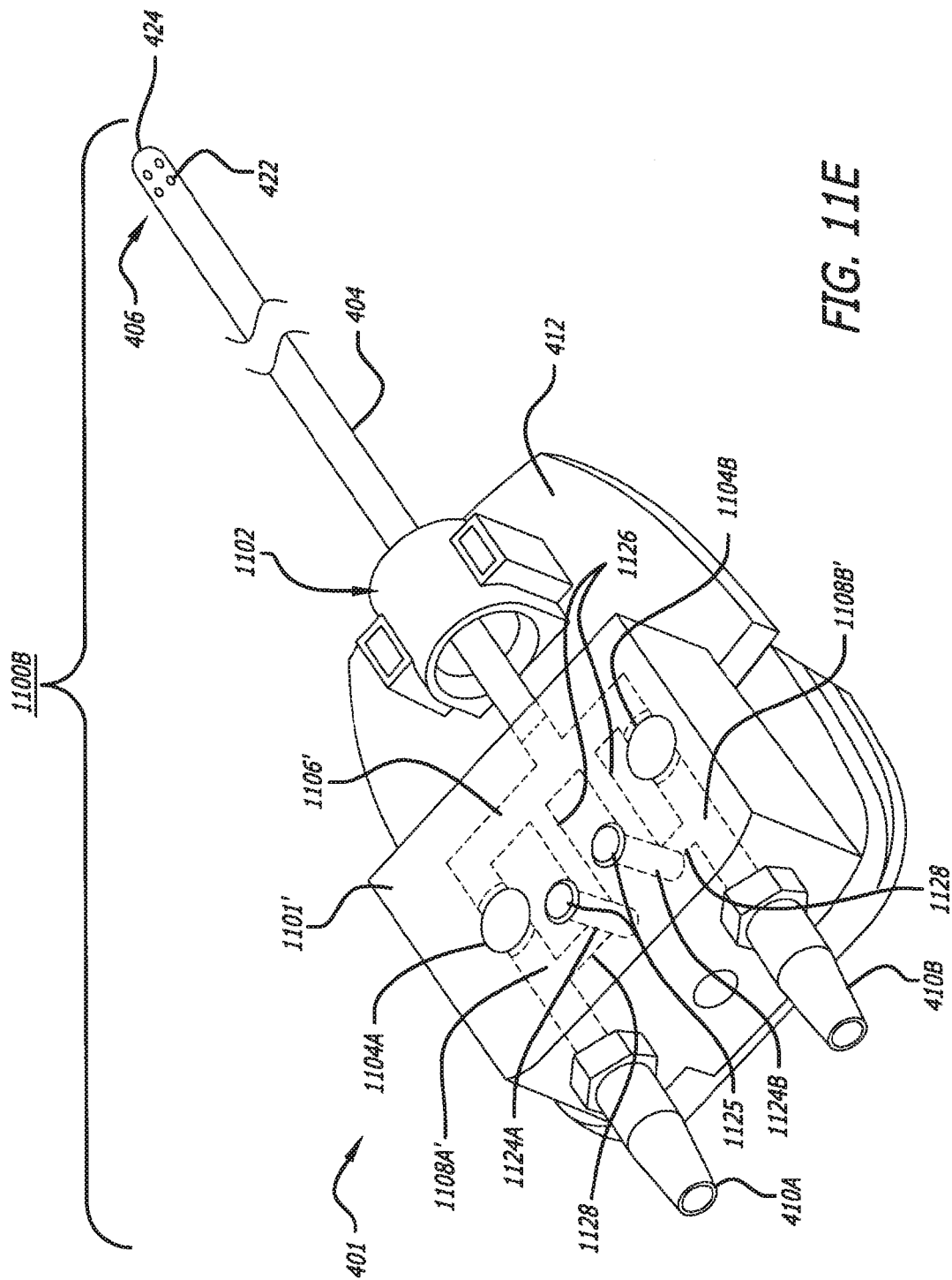
FIG. 11E is a top perspective view of an irrigation/aspiration/blowing robotic surgical tool with a solid valve body including robotically actuated valves and manually actuated valves.

Referring now to FIG. 11E, the solid valve body 1101 has been modified to solid valve body 1101' that includes manually controlled valves 1124A-1124B in parallel with the respective robotically controlled valves 1104A-1104B in order that the fluid flows through the IAB robotic surgical instrument 1100B may be controlled manually by hand and robotically from a master control console 150. The manually controlled valves 1124A-1124B are trumpet valves, a type of valve such as illustrated in FIG. 7A and previously described. The valves 1124A-1124B each include a button 1125 on top that extends out from the housing 401 through the cover 414 (not illustrated in FIG. 11E), such as illustrated in FIG. 13B. However, the trumpet valves 1124A-1124B are two-way two position valves that are linearly actuated by a finger or hand pushing on the button to open the valve and allow fluid to flow. As in valve 704A, each of the manually controlled valves 1124A-1124B includes a spring 706 to return the valve to a closed position when the force is released from the button 1125. (see FIG. 7A). The button 1125 is similar to the button 703 of the valve 704A illustrated in FIG. 7A.

To support the valves 1124A-1124B, the two way passages 1108A-1108B and the three way passage 1106 in the solid valve body 1101 illustrated in FIG. 11A are modified respectively into three way passages 1108A'-1108B' and a five way passage 1106' of the solid valve body 1101' illustrated in FIG. 11E. The five way passage 1106' includes one or more parallel passages 1126 to a port of the valves 1124A-1124B. That is, the five way passage 1106' has a first port to couple to the tube 404, a second port and a third port to respectively couple to valves 1104A,1104B, and a fourth port and a fifth port to respectively couple to the valves 1124A-1124B. The three way passages 1108A'-1108B' each include a side passage 1128 to a port of the valves 1124A-1124B. The three way passage 1108A' has a first port to couple to the valve 1104A, a second port to couple to the valve 1124A, and a third port to couple to the hose fitting 410A. The three way passage 1108B' has a first port to couple to the valve 1104B, a second port to couple to the valve 1124B, and a third port to couple to the hose fitting 410B. The solid valve body 1101' further includes an additional pair of valve openings to receive the spring 706 and the plunger 705 of the trumpet valve 704A. Additional seals may be provided around the shaft between the plunger 705 and the buttons 703, 1125.

Otherwise, the modified solid valve body 1101', including the structure and function of the valves 1104A-1104B, is similar to that of the solid valve body 1101 illustrated by FIGS. 11A-11D and described previously.

Figure 12:
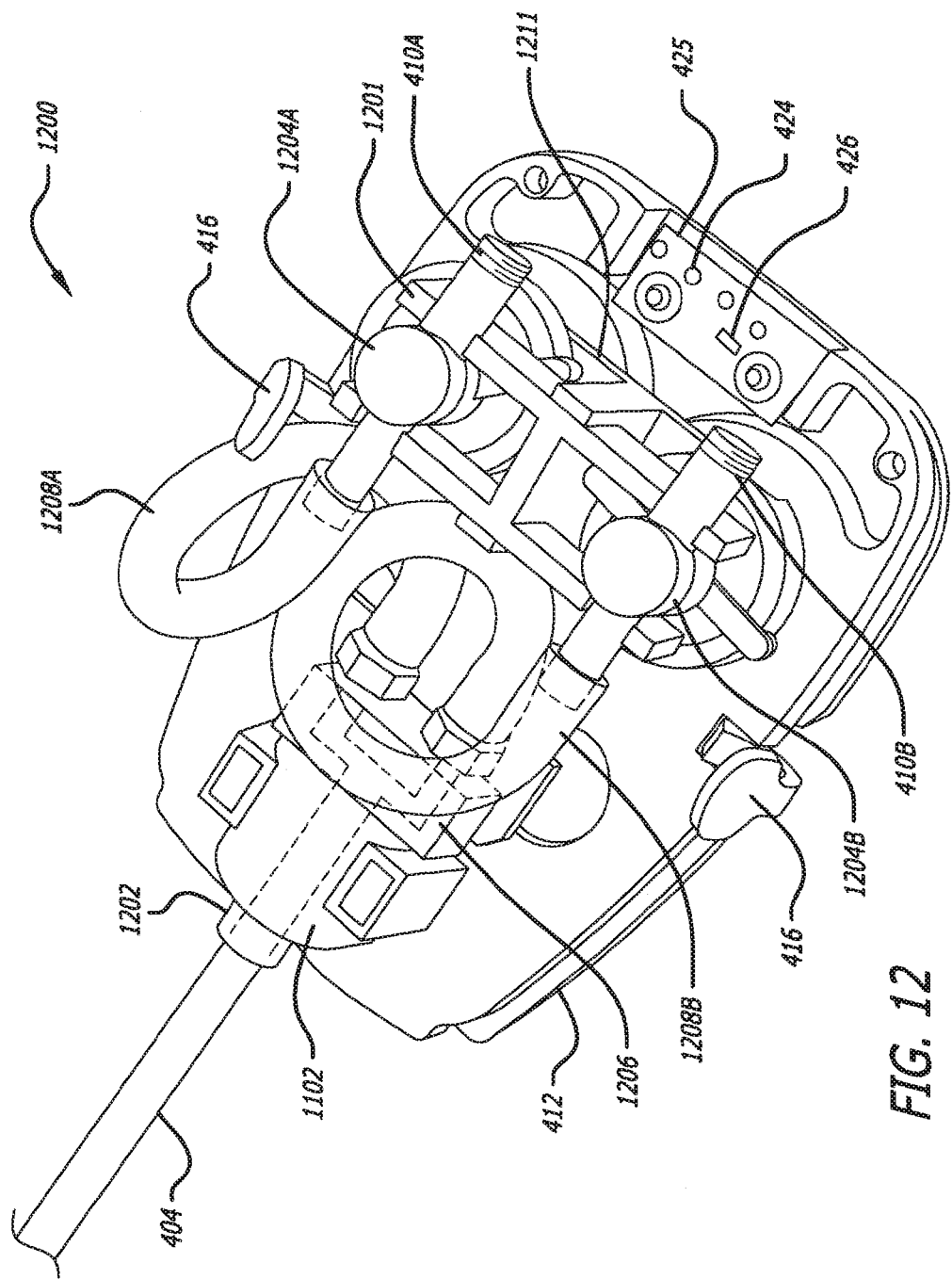
FIG. 12 is a top perspective view of an irrigation/aspiration/blowing robotic surgical tool with cover removed to show the replaceable valves.

Referring now to FIG. 12, a top perspective view of an IAB robotic surgical tool 1200 is illustrated with its cover over the mountable housing removed. The IAB robotic surgical tool 1200 includes a modular valve subassembly 1201. After being used once, the modular valve assembly 1201 and coupling hoses 1208A-1208B are readily replaceable with new used components. The remaining portion of the tool 1200 may be re-sterilized and then reused with a new modular valve assembly 1201 and coupling hoses 1208A-1028B. The modular valve subassembly 1201 is mountable to and dismountable from the interface base 412. A base 1211 of the modular valve subassembly 1201 may press fit into place to mount the valve subassembly to the interface base 412. The base 1211 of the modular valve subassembly 1201 includes recesses for rigid attachment of the ports of the valves 1204A-1204B and the ports of the hose fittings 410A-410B. Hoses 106A-106B may be coupled to ends of the hose fittings 410A-410B. The control and actuation of the rotatable valves 1204A-1204B was previously described with reference to FIG. 6A and the rotatable valve 604A.

The modular valve subassembly includes a first rotatable valve 1204A and a second rotatable valve 1204B. Each of the valves 1204A-1204B are two-way, two-position valves having a pair of ports. The valves 104A-104B may be trumpet valves, ball cock style valves, or other rotatable type of valve used to control the flow of gases or fluids. Coupled to the first ports of each valve 1204A-1204B are the hose fittings 410A-410B, respectively. Coupled to a second port of each of the valves 1204A-1204B are first ends of the respective coupling hoses 1208A-1208B. Second ends of the hoses 1208A-1208B respectively couple to a pair of ports of a three-way coupler 1206. A third port of the coupler 1206 couples to the hollow tube 404.

Shafts of the valves 1204A-1204B can be coupled to and decoupled from a pair of rotatable receiving elements 418. The modular valve subassembly 1201 is replaceable. After being used, the modular valve subassembly 1201 is dismounted from the interface base with shafts of the used valves 1204A-1204B being decoupled from the rotatable receiving elements 418. Similarly, shafts of new unused valves 1204A-1204B may be coupled to the rotatable receiving elements 418 when mounting a new modular valve subassembly to the interface base.

Coil springs may be wrapped around the shafts of the valves 1204A-1204B and coupled to the pair of rotatable receiving elements 418 in order to spring load the valves 1204A-1204B to automatically close so that neither suction nor irrigation are activated when the instrument housing is not mounted onto the robotic arm, or modular valve subassembly is not mounted to the interface base 412 in the mountable housing 401.

The hollow tube 404 is supported by the interface base. A bushing 1202 may be inserted over the hollow tube 404 and pressed into the collar 1102 of the interface base 412.

The printed circuit board 425 may also be mounted to the interface base 412. Electrical pins 424 may couple to the printed circuit board 425 to provide an electrical connection to the adaptor 228. The integrated circuit 426 is mounted to the printed circuit board. may be reprogrammed to indicate that the tool 1200 has been re-sterilized and its components replaced.

In order to reuse the IAB robotic surgical tool 1200, the modular valve subassembly 1201 and the coupling hoses 1208A-1208B are removed and discarded. A new valve subassembly 1201 and new hoses 1208A-1208B are installed and mounted in the robotic surgical tool. The remaining components including the interface base 412, the three-way coupler 1206 and the hollow tube 404 are re-sterilized prior to fitting a new modular valve subassembly 1201 and new hoses 1208A-1208B.

After re-sterilization, the integrated circuit 426 may be programmed to indicate that the tool 1200 has been re-sterilized and its components replaced.

Figure 13A:
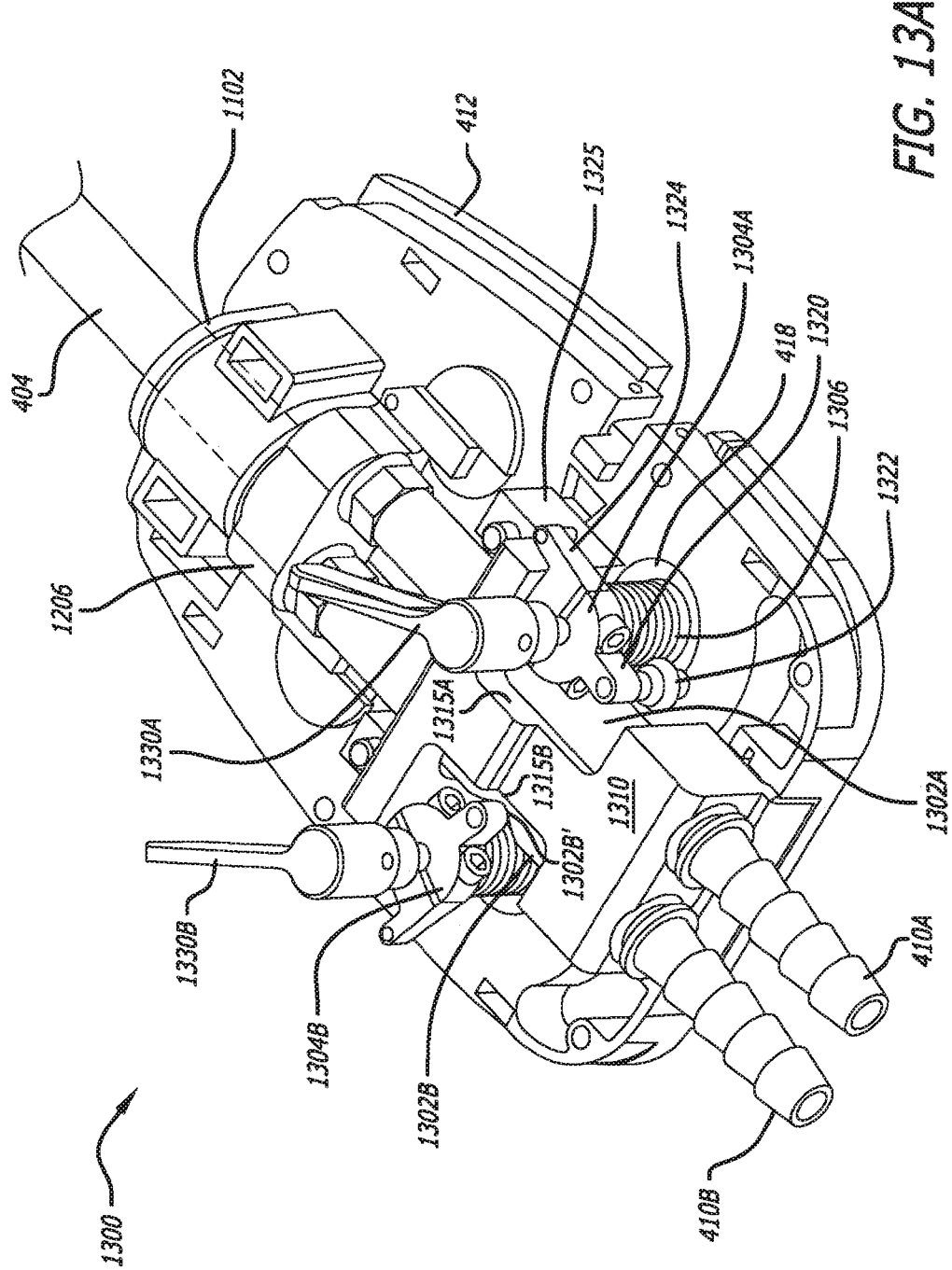
FIG. 13A is a top perspective view of an irrigation/aspiration/blowing robotic surgical tool with cover removed to show rotatable pinch valves.
Figure 13B:
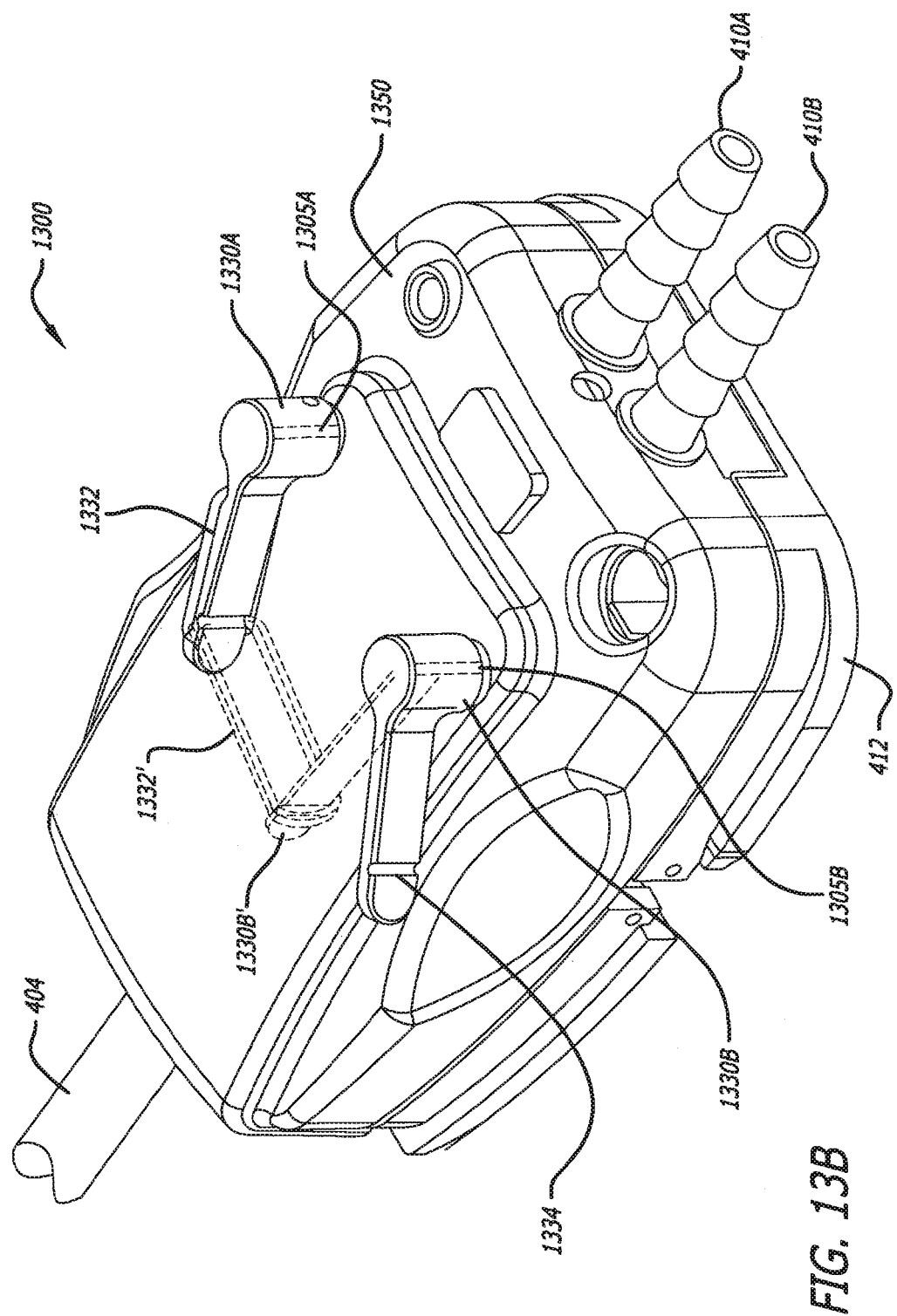
FIG. 13B is a top perspective view of the irrigation/aspiration/blowing robotic surgical tool of FIG. 13A with cover in place to show manual handles and a cleaning position of the handles.

Referring now to FIGS. 13A-13B, an IAB robotic surgical tool 1300 to control the flow of fluids into and out from a surgical site is illustrated. FIG. 13A illustrates the IAB robotic surgical tool 1300 with its cover removed to show that the IAB robotic surgical tool 1300 includes a flow control system that utilizes rotatable pinch valves 1304A-1304B.

To control the flow of fluids through the robotic surgical tool 1300, a pair of flexible coupling hoses 1302A-1302B are coupled to a pair of hose fittings 410A-410B at a first end and a pair of ports of a three-way coupler 1206 at a second end. The third port of the three-way coupler 1206 is coupled to the proximal end of the hollow tubing 404. To pinch off hoses 1302A-1302B, the tool 1300 includes a rotatable pinch valves 1304A-1304B rotatably mounted to the interface base 412. Each of the pinch valves 1304A-1304B is coupled to a rotatable receiving element 418. As discussed previously, the rotatable receiving element 418 may couple to a rotatable driver 234.

Each of the rotatable pinch valves 1304A-1304B may include a coil spring 1306, a rotatable pinch arm 1320, a pinch wheel 1322 coupled to the end of the rotatable pinch arm 1320, a tab 1324, and a handle 1330. In FIG. 13A, the pinch valve 1304A is illustrated as being open and allowing the flow of fluid through the tool 1300. Rotatable pinch valve 1304B is illustrated as being closed to pinch off hose 1302B at a pinch point 1302B'.

At a pinch point 1302B', a pinch wheel 1322 presses the hose 1302B against the backstop 1315B of bulkhead 1310. The hose 1302B collapses to a diameter of zero so that no fluid can flow through it at the pinch point 1302B'. The rotatable pinch valve 1304A may utilize the backstop 1315A of bulkhead 1310 to close and pinch off hose 1302A. The operation of a rotatable pinch valve is further discussed herein with reference to FIG. 10A. When being opened from the closed position, the tab 1324 may be used to limit the rotation of each rotatable pinch valve 1304A-1304B to a stop 1325.

In order to readily collapse and pinch off the flow of fluids, the hoses 1302A-1302B may be silicon hoses that are flexible with the capability of expanding to an open noncollapsed diameter from a collapsed state at the pinch point in response to opening the rotatable pinch valves. The pinch wheel 1322 rotates along the hose as its being pinched off so as to avoid damaging the hose and cause leaks.

The coil spring 1306 wrapped around the shafts of the pinch valves 1304A-1304B may be used to spring load the valves 1204A-1204B to automatically close and pinch off the hoses 1302A-1302B when the instrument housing is dismounted from the robotic arm or otherwise not being actuated.

While the IAB robotic surgical tool 1300 is typically under control of the master control console 150, the handles 1330A-1330B allow for manual use of the IAB robot surgical tool 1300 when it is not mounted to a robotic arm. The handles 1330A-1330B are respectively coupled to the shafts 1330A-1330B of the rotatable pinch valves 1304A-1304B in order to manually rotate them open and closed by hand. When the IAB robot surgical tool 1300 is not mounted to a robotic arm so that the rotatable receiving elements 418 are not engaged with the rotatable drivers 234, the assistant surgeon or nurse may manually operate the IAB robotic surgical tool 1300 to control the fluid flows by using the handles 1330A-1330B. Furthermore, the handles 1330A-1330B allow for cleaning the flow control system as is described further below.

Referring now to FIG. 13B, the IAB robotic surgical tool 1300 is illustrated with its cover 1350 coupled to the interface base 412. The cover 1350 provides protection to the flow control system 417 including the rotatable pinch valves in the hoses. The handles 1330A-1330B extend through the cover 1350 so that they are accessible to manually control the pinch valves.

Additionally, the handle 1330A includes a clip 1332 that may be swung around and fitted into a groove 1334 of the handle 1305B. With the clip 1332 within the groove 1334, both handles 1330A-1330B are open such that neither hose 1302A nor hose 1302B is pinched closed. The handles are clipped together in the open position during a cleaning of the flow control system of the robotic surgical tool 1300 and to ease replacement of the hoses.

To clip the handles together, the handle is rotated to the open position and the clip 1332 is swung to position 1332'. The handle 1330B is rotated to position 1330B' so that the clip 1332' may be inserted into its groove 1334. In this position, the pinch valves are both open and the hoses 1302A-1302B are not pinched off but are open so that they can be cleaned.

Figure 14:
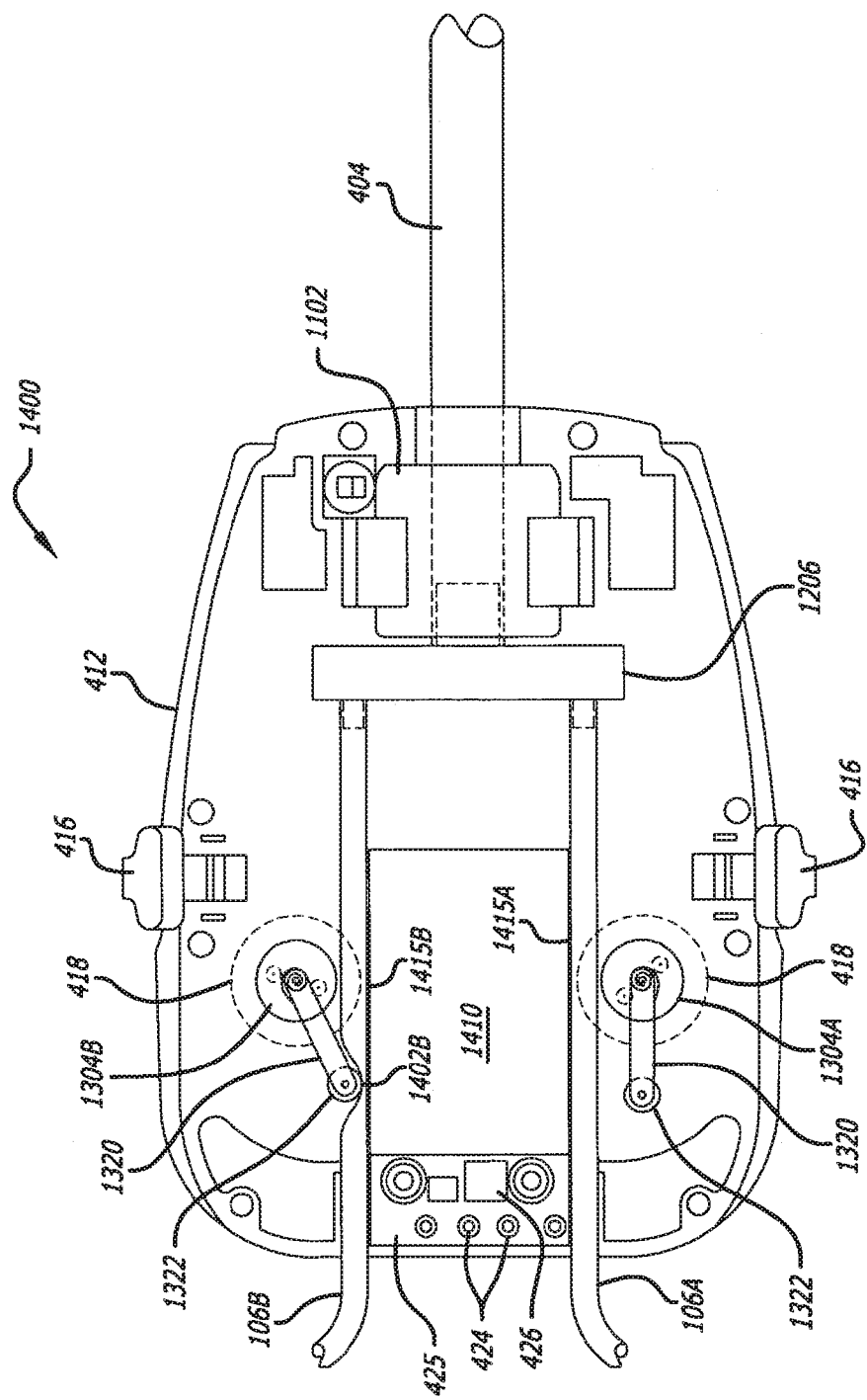
FIG. 14 is a top view of an irrigation/aspiration/blowing robotic surgical tool with cover removed to show the pinch valves and replaceable tubing.

Referring now to FIG. 14, a top view of a IAB robotic surgical tool 1400 is illustrated with its cover removed to show the pinch valves and replaceable tubing. The tool 1400 is substantially similar to tool 1300 previously described but for use of the coupling hoses 1302A-1302B to control the flow of fluids within the tool. Tool 1400 eliminates the hose fittings 410A-410B and the short coupling hoses 1302A-1302B between the hose fittings 410A-410B and the three-way coupler 1206. Instead, the tool 1400 includes replaceable hoses 106B-106A directly coupled to the ports of the three-way coupler 1206, as is illustrated in FIG. 14. The replaceable hoses 106B-106A extend beyond the robotic surgical tool in order to couple externally to sources of fluids.

In contrast, the coupling hoses 1302A-1302B of the tool 1300 require cleaning and sterilization after each use of the tool 1300 in order for it to be reused. In tool 1400, the hoses 106A-106B are not cleaned, but replaced after each usage with new sterile hoses so that the tool 1400 may be reused. With the rotatable pinch valves open, the interface base 412 is formed with bulkhead 1410 to allow the hoses 106A-106B to be readily replaceable and coupled to the three-way coupled 1206.

The tool 1400 includes the rotatable pinch valves 1304A-1304B with their pinch arms 1320 and pinch rollers 1322 coupled thereto to pinch off the hoses 106A-106B and stop the flow of fluids. The rotatable pinch valves are rotatably mounted to the interface base 412. The shaft of each rotatable valve is coupled to the rotatable receiving element 418.

In FIG. 14, rotatable pinch valve 1304A is open such that hose 106A may allow a fluid to flow therein. Rotatable pinch valve 1304B is closed to pinch off hose 106B at point 1402B. Thus, with pinch valve 1304B closed, a fluid will not flow through hose 106B. Bulkhead 1410 is provided so that the hoses 106A-106B may be readily replaced when the rotatable pinch valves 1304A-1304B are held in their open positions. The bulkhead 1410 includes backstops 1415A and 1415B against which the rotatable pinch valves 1304A-1304B may pinch off the respective hoses 106A-106B. Hoses 106A-106B may be formed of a silicon rubber compound so that they are flexible and can be readily collapsed and expanded in response to the opening and closing of the rotatable pinch valves.

As discussed previously, the replaceable hoses 106B-106A are directly coupled to two of the three ports of the three-way coupler 1206. The third port of the three-way coupler 1206 is coupled to the proximal end of the hollow tube 404. The hollow tube 404 may be further supported by the interface base 412 by inserting a the hollow tube into a bushing mounted in the collar 1102.

The IAB robotic surgical tools, including tool 1400, may further include the printed circuit board 425 with one or more pins 424 and one or more interrelated circuits 426 coupled thereto to indicate its tool type, whether its new or refurbished, and if refurbished, the number of prior uses.

Referring now to FIGS. 15A-15B, IAB robotic surgical tools 1500A-1500B are respectively illustrated without their covers. The tools 1500A-1500B do not internally control the flow of fluids into and out of a surgical site. Instead, the control of the flow of fluids into and out of a surgical site is externally controlled away from the surgical tool. As previously discussed with reference to FIG. 1, the control of fluids may be provided at the respective fluid pumps by the computer system 151 in the surgeons master control console 150 under the control of the operator O.

Even though fluid flow is externally controlled, the IAB robotic surgical tools 1500A-1500B are mounted to a robotic arm of the robotic surgical manipulator 152 and can facilitate the flow of fluids into and out of a surgical site through couplers and the hollow tube 404.

In FIG. 15A, the IAB robotic surgical tool 1500A includes a three-way coupler 1206 mounted to the interface base 412. A proximal end of the hollow tube 404 couples to a first port of the three-way coupler 1206. Replaceable hoses 106A-106B respectively couple to a second and a third port of the three-way coupler 1206. The tool 1500A may further include the printed circuit board 425 with the electrical pins 424 in one or more interrelated circuits 426 coupled thereto to indicate the tool type and that external fluid control is to be utilized.

In FIG. 15B, the IAB robotic surgical tool 1500B includes a four-way coupler 1506 with a first port coupled to the hollow tube 404, a second port coupled to an end of a first hose 106A, a third port coupled to an end of a second hose 106B, and a fourth port coupled to an end of a third hose 106C. Tool 1500B may also include the printed circuit board 425 with the electrical pins 424 and the one or more integrated circuits 426 coupled thereto to indicate the tool type and that external fluid control is to be utilized to control the flow of fluids flow in the hoses 106A-106C.

Cleaning and sterilization of the IAB robotic surgical tools 1500A-1500B is fairly easy as there are no valves. To reuse the tools 1500A-1500B, used hoses 106A-106C are removed. The remaining portions of the tools 1500A and 1500B, such as the couplers and the hollow tube 404, are then sterilized and then fitted with new sterile hoses 106A-106C so that they may be reused.

While IAB robotic surgical tools 1500A-1500B have been shown and described to include couplers 1206, 1506, respectively, the couplers can be removed and provided externally to the surgical tools 1500A-1500B. In which case, a single hose would be routed from the external coupler to the IAB robotic surgical tool. The single hose may couple to a hose fitting, that in turn would be coupled to the hollow tube 404. Alternatively, the proximal end of the hollow tube could be formed as a hose fitting and directly couple to an end of the hose. In this manner, reuse of the IAB robotic surgical tool may further simplified with fewer components to sterilize and a single hose to replace.

User Control

Typically, irrigation and aspiration of a surgical site are manually controlled by an assisting surgeon or nurse using manual surgical tools. By allowing tele-operated or remote control and actuation of an IA or IAB robotic surgical instrument, the primary surgeon can now control irrigation and aspiration of a surgical site.

The flow control system of the IAB robotic surgical instrument may be controlled by the operator O seated at the robotic surgical master control console 150 in a number of ways. For example, master axes of movement in a control handle that is normally used for controlling a wristed robotic surgical instrument may be used to activate irrigation, aspiration, and or blowing through an IAB robotic surgical instrument over a surgical site. As previously discussed, one or a combination of both the rotational motion of the touch sensitive handle 325 and the squeezing motion of the grips 350A, 350B may be used to control the flow of fluids through the IAB robotic surgical tools. For example, the rotational motion of the touch sensitive handle 325 may be used for the control of irrigation while the squeezing motion of the grips 350A, 350B may be used for controlling suction in a surgical site.

Figure 16A:
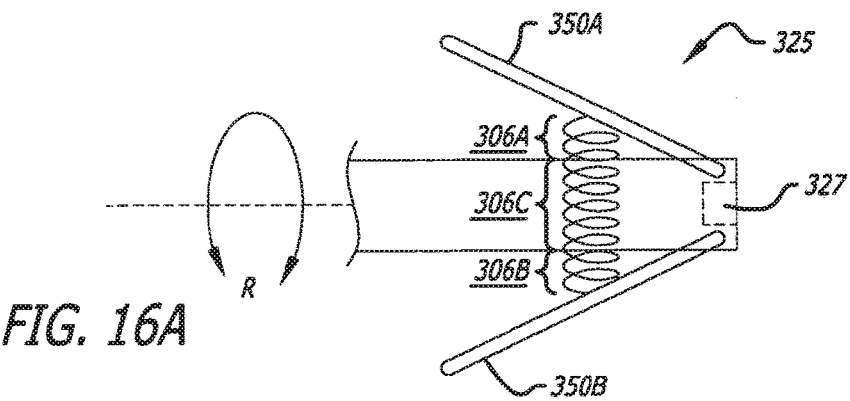
FIG. 16A is a side view of the touch sensitive handle of the diagram of the touch sensitive handle illustrated in FIG. 3B for the robotic surgical master control console of FIG. 3A.

FIG. 16A is a side view of the touch sensitive handle 325 of the robotic surgical master control console 150. The touch sensitive handle 325 may be used by the operator O to control the fluid flow in IAB robotic surgical instruments. In one embodiment of the invention, a rotational motion R ("roll") of the touch sensitive handle may control the irrigation, aspiration, and/or blowing through IAB surgical instruments 101A, 400. For example, the handle may rotated clockwise to open a first valve to have a fluid flow through the IAB surgical instrument into or out of a surgical site. The handle may then be rotated counter-clockwise to close the first valve and stop the flow of fluid through the IAB surgical instrument and into or out of the surgical site. A center detent point D of rotation in the touch sensitive handle 325 may be used to switch over from one type of fluid flow to another. In which case, the handle may rotated counter-clockwise to open a second valve or switch open the first valve to a different position to have a second fluid flow through the IAB surgical instrument and into or out of a surgical site. The handle 325 may then be rotated clockwise to the center detent point D to close the second valve and stop the flow of fluid through the IAB surgical instrument and into or out of the surgical site.

The rotational motion of the handle 325 may typically control wrist motors in the robotic surgical manipulator 152 to control a wrist motion of a robotic surgical tool. In this case, the wrist motors in the robotic surgical manipulator 152 may be adapted for use to control one or move valves in the IAB robotic surgical instruments in response to the rotational motion of the handle 325.

In another embodiment of the invention, a gripping or squeezing motion ("master grip") on the grips 350A-350B of the touch sensitive handle 325 may be used to control the flow of fluids through IAB robotic surgical instruments. For example, squeezing the grip of touch sensitive handle may be used to turn on the suction of the I/A/B surgical instrument and the grip released to turn off the suction. In which case, the touch sensitive handle may include one or more springs 306A-306C to provide differing spring constants or a single spring 306 with a progressive rate spring constant as the positions of the grips 350A-350B change. An explanation as to how the touch sensitive handle 325 functions was previously describe with reference to FIG. 3C. By using the grip of the touch sensitive handle 325 to control the IAB robotic surgical instrument, the rotational motion of the handle may be used for further movement or control of the instrument.

The position of the grips 350A-350B can vary over a range of positions in order to control suction, blowing and irrigation of a surgical site such as from a fully released or fully open position to a fully squeezed or fully closed position.

Figure 16B:
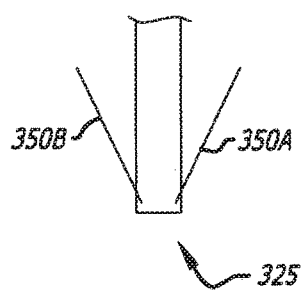
FIGS. 16B-16D are side views of grip positions of the touch sensitive handle to control the irrigation/aspiration/blowing robotic surgical tool in a surgical site.
Figure 16C:
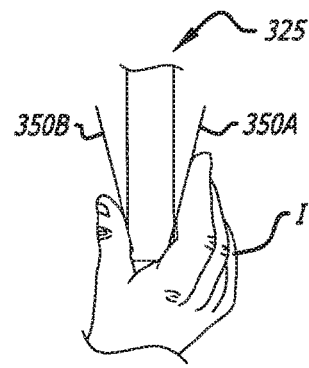
Figure 16D:
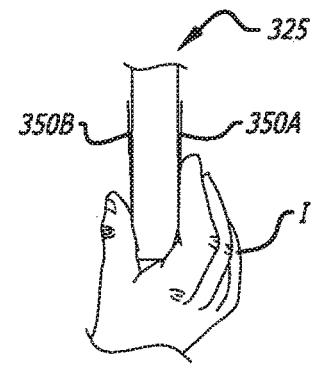

FIGS. 16B-16D illustrate different positions of the grips 350A-350B of the touch sensitive handle 325 when squeezed by a hand H of the operator O to control the IAB robotic surgical tool at a surgical site. FIG. 16B illustrates a fully open grip position without any squeezing by the hand H. FIG. 16C illustrates the hand H squeezing the grips 350A-350B to a half-way closed position. To provide force feedback to a user, a first spring rate may be used over a range of positions, such as from the fully open to the half-way closed position. FIG. 16D illustrates the hand H squeezing the grips 350A-350B to a fully closed position. To provide force feedback to a user, a second spring rate somewhat greater than the first may be used over a range of positions, such as from the half-way closed position to the fully closed position.

Figure 17:
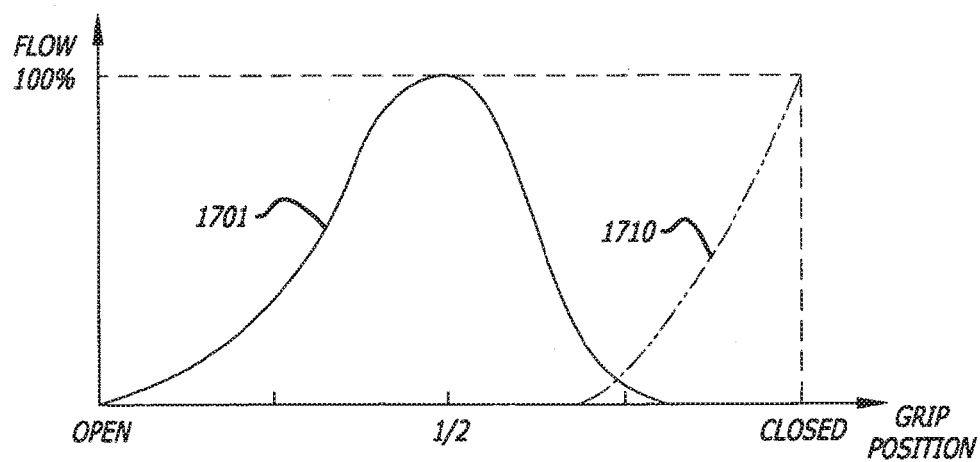
FIG. 17 is a graph showing exemplary control of irrigation and aspiration using grip control of the touch sensitive handle corresponding to the side views of the touch sensitive handle illustrated in FIGS. 16B-16D.

FIG. 17 is a graph showing exemplary control of irrigation and aspiration using the grip control of the touch sensitive handle 325. The open, half, and closed positions along the X-axis of the graph correspond to the different positions of the grips 350A-350B of the touch sensitive handle 325 illustrated in FIGS. 16B-16D. Curve 1701 illustrates a flow of vacuum or a percentage of suction. Curve 1710 illustrates a flow of irrigation fluid through the tool and into a surgical site.

With the grips 350A-350B in the fully released or fully open position, both suction and irrigation are turned off. As the grip is initially squeezed, suction is turned on and irrigation remains turned off. As the grip position changes from fully-open to half-way closed, curve 1701 illustrates the flow of vacuum change from zero to one hundred percent. As the grip reaches half way, suction may be fully turned on with a negligible amount of irrigation. As the operator O squeezes further still, past the half-way closed position, the vacuum flow tapers off toward zero and the irrigation begins from zero around the three-fourths closed position, as is illustrated by curves 1701 and 1710.

In another embodiment of the invention, both the rotational motion of the touch sensitive handle 325 and the squeezing motion of the grips 350A, 350B may be used to control the flow of fluids through the IAB robotic surgical tools.

In addition to the touch sensitive handle 325 and its grips 350A-350B, foot pedals 318 of the surgeons master control console 150, as illustrated in FIG. 3A, may be used to further control the IAB robotic surgical tools. For example, one of the foot pedals 318 may be used to switch from suction control to blow control in order to blow a pressurized gas over the surgical site. In which case, a gripping squeezing motion of the touch sensitive handle can also control the blowing provided by the I/A/B surgical instrument.

Alternatively, the touch sensitive handle 325 may be modified to include buttons to activate irrigation, aspiration, and or blowing when an IAB robotic surgical tool is mounted to the robotic surgical manipulator 152

To avoid using a touch sensitive handle, the foot pedals 318 of the surgeons master control console 150 may be used to fully control the suction and irrigation provided by an IAB robotic surgical tool. In one embodiment of the invention, a first foot pedal 318A may be used to control suction and a second foot pedal 318B may be used to control the irrigation provided by an IA or IAB surgical instrument.

With knowledge of other surgical instruments that are to be controlled by some of the foot pedals, foot pedals on the right side of the footrest may be used, for example. Two pedals and a toggle switch on the master control console or the control handle may be used to control a variety of actuations in a plurality of surgical instruments knowing the context of the robotic surgical system in advance. Additionally, foot pedals normally used for cautery (or another energy device) may be switched to activate irrigation, aspiration, and or blowing when an IAB robotic surgical tool is mounted to the robotic surgical manipulator 152.

To avoid any use of hands or feet in controlling the I/A surgical instrument, voice activation may be used to activate irrigation, aspiration, and or blowing when an IAB robotic surgical tool is mounted to the robotic surgical manipulator 152. In this case, an operator's voice or speech may be used to control the suction, irrigation, and or blowing provided by an IA or IAB surgical instrument. For example, spoken voice commands such as "suction ON", "suction OFF", "suction lightly", "irrigation ON", "irrigation OFF", and "irrigate lightly" may be used to control the suction and irrigation provided by the IA or IAB surgical instrument.

To recognize the voice commands, the master control console 150 includes a microphone 315 and a speech recognizer 317. The speech recognizer 317 may generate the control signals that are provided to the IA or IAB surgical instrument.

While various control means have been individually described here, two or more of these control means may be combined in order to control the flow of fluids through an IAB robotic surgical tool. For example, the rotational motion of the touch sensitive handle 325 may be used for the control of irrigation while the squeezing motion of the grips 350A, 350B may be used for controlling suction in a surgical site.

User Feedback

Within a surgical site it may be difficult to determine if a valve is open and providing suction, blowing, or irrigation. User feedback may be provided to the surgeon at the console to provide information to him/her such as suction is on and at what level—high, medium, low, or otherwise off. User feedback information may also be provided regarding blowing and irrigation—whether its off or on, and if on at what level—high, medium, or low. However, it typically is easier to visually determine when a liquid is flowing for irrigation than when suction is provided for aspiration or a pressurized gas for blowing.

Referring now to FIGS. 18A-18G, various types of user feedback may be provided to the IAB robotic surgical tools.

Figure 18A:
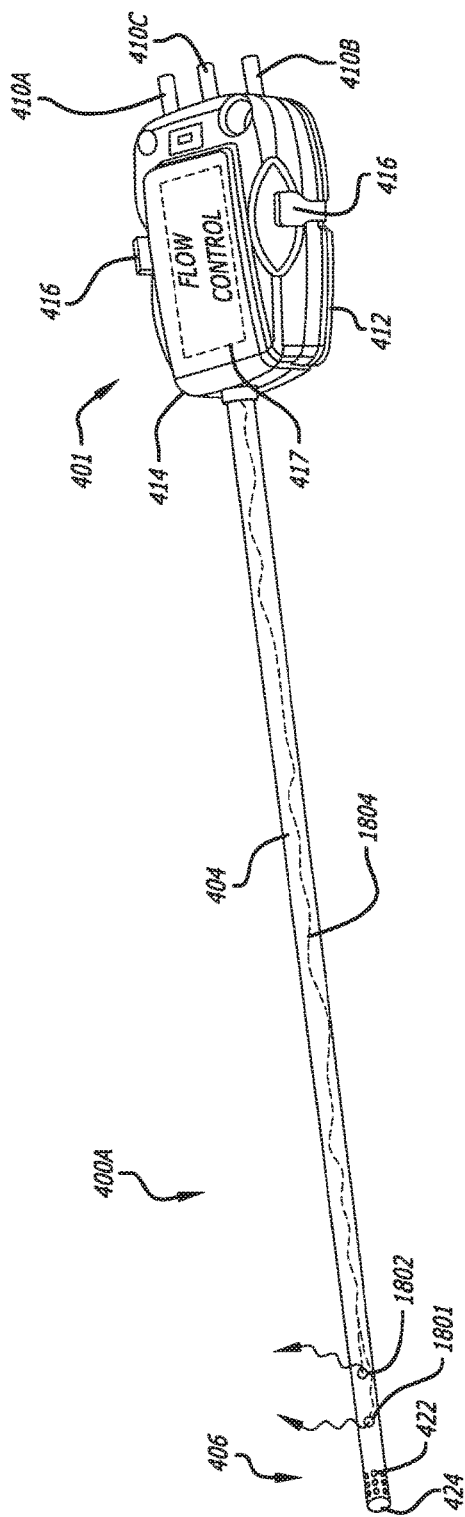
FIG. 18A is a top perspective view of the irrigation/aspiration/blowing robotic surgical tool with light emitting diodes at the distal end to provide user feedback.

In FIG. 18A, the irrigation/aspiration/blowing robotic surgical tool 400A includes a pair of light emitting diodes (LEDs) 1801-1802 near the tip 406 of the hollow tube 404 in order provide visible feedback to an operator O that a fluid is flowing through the tool. One or more wires 1804 may couple between the light emitting diodes 1801-1802 and the printed circuit board 425 within the mountable housing 401. Electrical signals can be transmitted towards the light emitting diodes from the printed circuit board to turn them on during the flow of fluids and off when no fluid flow occurs. The integrated circuit 426 may generate the electrical signals to control the light emitting diodes. In this manner, the light emitting diode 1801-1802 may be activated by control signals received over the one or more wires 1804 from the master control console 150. Additional light emitting diodes may be provided near the tip 406 of the hollow tube 404 in order provide additional visible feedback for additional fluid flows. Moreover, the light emitting diodes 1801-1802, including any additional LEDs, may emit photons of different wavelengths in order that different colors can be provided corresponding to different types of fluid flow (e.g., suction, irrigation, gas pressure).

Figure 18B:
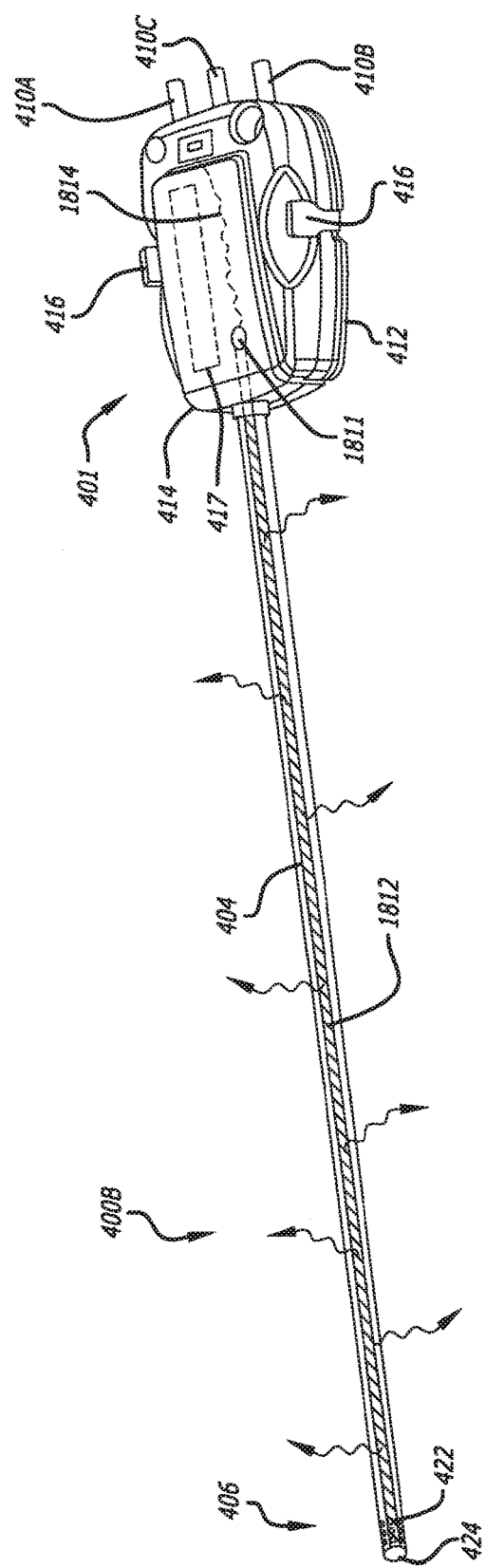
FIG. 18B is a top perspective view of the irrigation/aspiration/blowing robotic surgical tool with a light pipe along side the flow tube that is coupled to a light emitting diode at the proximal end to provide user feedback.

In FIG. 18B, the IAB robotic surgical tool 400B includes a light pipe 1812 mounted externally to the hollow tube 404 to provide visible user feedback to the operator O that fluids are flowing into or out of the surgical site. The light pipe 1812 may be a side lighting fiber optic cable with one end optically coupled to one or more light emitting diodes 1811 to receive photons. The light emitting diodes 1811 may emit photons of different wavelengths in order that different colors can be provided corresponding to different types of fluid flow (e.g., suction, irrigation, gas pressure). One or more wires 1814 may couple between the one or more light emitting diodes 1811 and the printed circuit board 425 mounted within the housing 401. An integrated circuit, such as integrated circuit 426, may be used to drive the one or more light emitting diodes 1811 to turn them on or off. Alternatively when fluids flow, the one or more light emitting diodes 1811 may be activated directly by control signals received over the one or more wires 1814 from the master control console 150 or from the integrated circuit 426. More than one light pipe 1812 may be provide along the circumference of the hollow tube 404 so that the side light may be visible at different viewing angles and positions of the IAB robotic surgical instrument.

In comparison with the light emitting diodes 1801-1802 at the tip, the light pipe 1812 provides a light that may be visible along the entire length of the hollow tube 404 so that it can be seen, regardless of the position of the tip. Additionally, the light emitting diode 1811 is protected under the cover of the mountable housing 401.

Figure 18C:
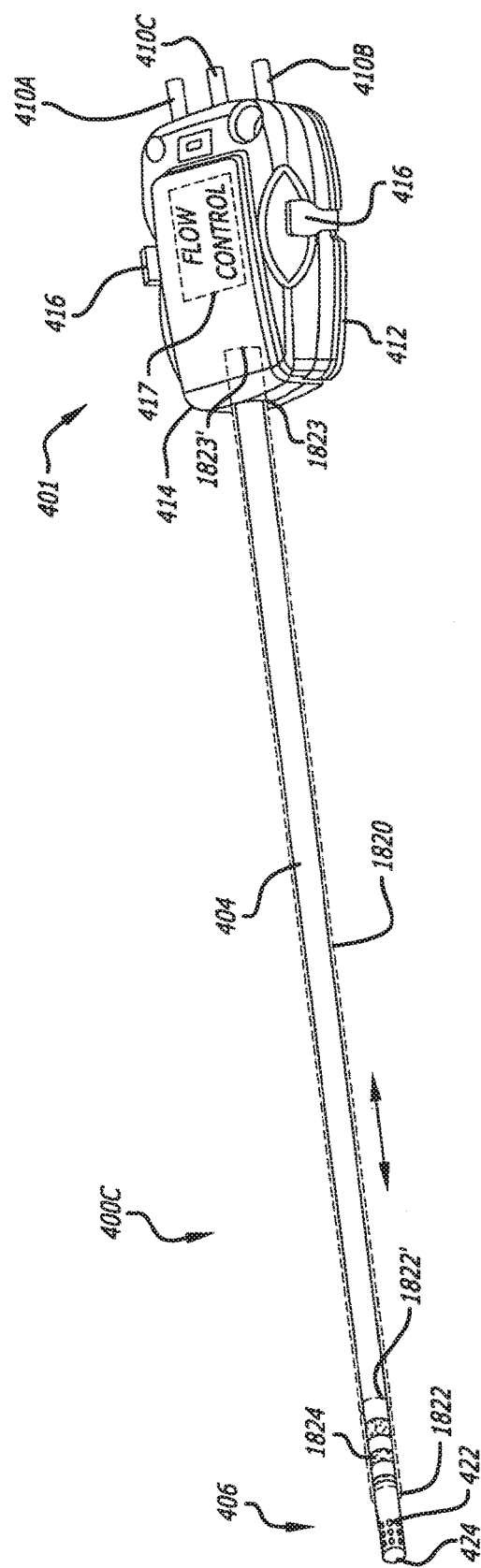
FIG. 18C is a top perspective view of the irrigation/aspiration/blowing robotic surgical tool with a sliding sleeve around the flow tube that is moved to reveal a scale at the distal end to provide user feedback by mechanical means.

Referring now to FIG. 18C, an IAB robotic surgical tool 400C is illustrated. In tools 400A-400B previously described, user feedback was provided by electro-optic means. In contrast, the user feedback provided by the tool 400C is provided mechanically. The IAB robotic surgical tool 400C includes a sliding sleeve 1820 and a visible scale 1824 coupled to the hollow tube 404. The sliding sleeve 1820 is coaxial with the hollow tube 404 and covers over the scale 1824 when no fluid is flowing through the tool. The sliding sleeve 1820 can be slid along the hollow tube 404 and into the housing 401 to reveal the visible scale 1824 as fluids flow through the tool 400C. The visible scale 1824 may be different colored bands to indicate the level of fluid flow within the tool 400C. Alternatively, the visible scale 1824 may be bands of different thickness to reveal the amount of fluid flow within the tool 400C. The sliding sleeve 1820 can be gradually received into the hosing 401 to reveal the appropriate scale in proportion to the amount of fluid flow in the tool 400C.

Without any flow of fluids within the tool 400C, a tip 1822 of the sliding sleeve 1820 may completely cover over the visible scale 1824. With maximum fluid flow in the tool 400C, the sliding sleeve 1820 may be slid into the housing 401 such that its tip moves to a position 1822' to fully reveal the visible scale 1824. The opposite end 1823 of the sliding sleeve 1820 moves inward to position 1823'. In this manner, the level of fluid flow in the tool 400C may be provided to a user by mechanical means.

The sliding sleeve 1820 may be pulled into the housing 401 and pushed back out in a variety of ways. A spring may used to apply a force against the retraction of the sliding sleeve 1820 into the housing so that it can push it back out after the pulling force is released. A cable with one end coupled to and wrapped around a take up drum may be coupled to the sleeve 1820 through a pulley in order to pull the sleeve into the housing 401. A gearing system may alternatively be used. A pinion gear may couple to a rotatable receiving element 418 and to a rack coupled to the sleeve 1820. Alternatively, a ball screw and a lead screw may be used. A slider with a crank or lever arm may be used. An electrical means may also be used, such as a solenoid to pull in on the sliding sleeve 1820.

Referring now to FIGS. 18D-18G, an IAB robotic surgical tool 400D includes another mechanical structure to provide user feedback. However instead of a sliding sleeve, the IAB robotic surgical tool 400D includes a rotating sleeve 1820' coaxial with the hollow tube 404. FIGS. 18E-18G illustrate various types of tips 406 and sleeves 1820A'-1820C' that may be used to provide user feedback.

Figure 18D:
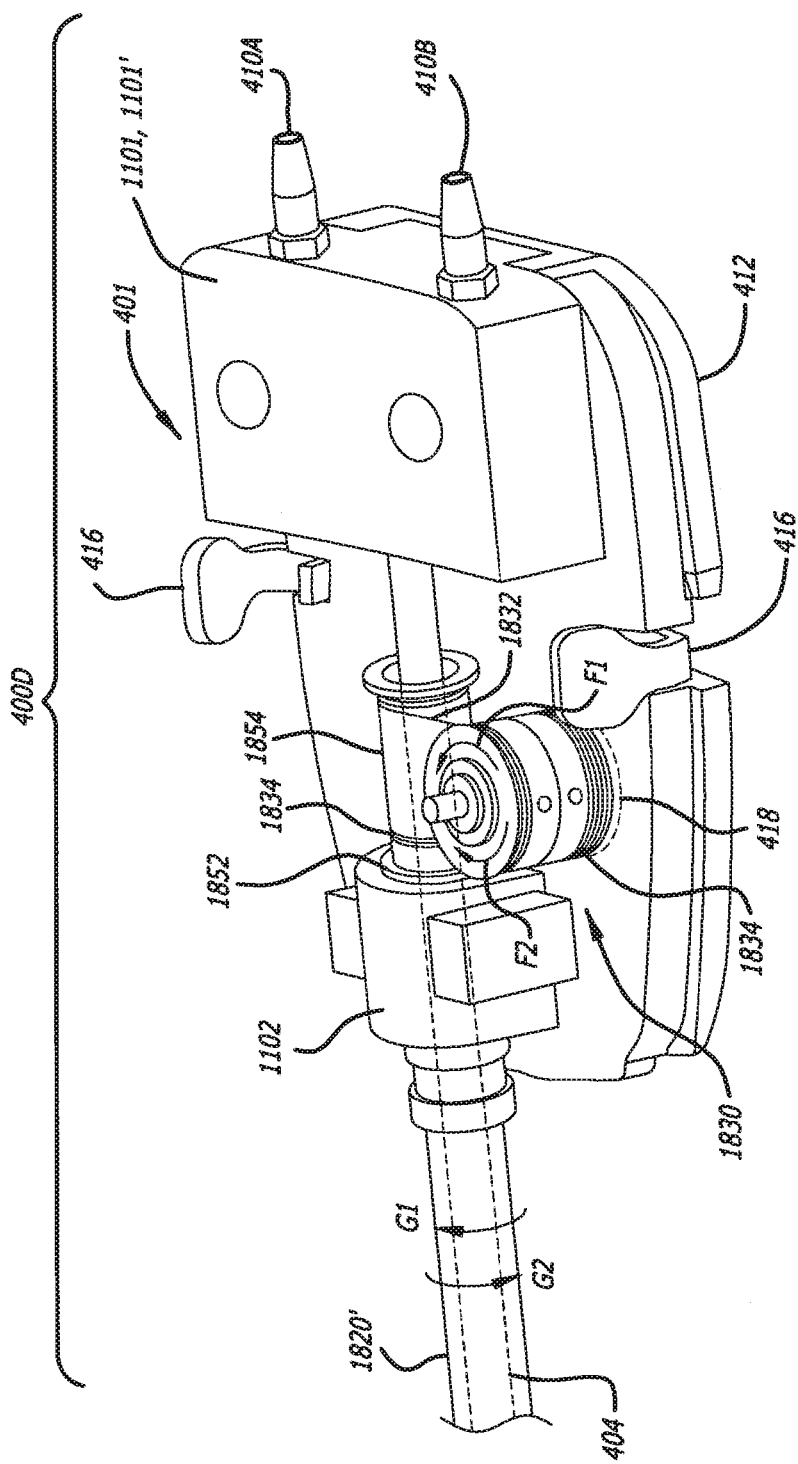
FIG. 18D is a top perspective view of the irrigation/aspiration/blowing robotic surgical tool with a rotational sleeve around the flow tube that rotates to reveal a scale at the distal end and provide user feedback by mechanical means.

In FIG. 18D, the IAB robotic surgical tool 400D includes the hollow tube coupled to the solid valve body 1101, 1101' mounted to the interface base 412. The tool 400D further includes the hollow rotatable sleeve 1820' coaxial around the hollow tube 404. The rotatable sleeve 1820' couples to a bearing assembly 1852 mounted to the collar 1102 to rotatably mount to the interface base 412.

For rotational purposes, the rotatable sleeve 1820' includes a drum 1854 that extends from the bearing assembly 1852 into the housing 401. There are a number of ways to couple a rotational movement from the surgical manipulator to the rotatable sleeve 1820'. In one embodiment of the invention, the tool 400D is backward compatible and includes a spool 1830 rotatably mounted to the interface base 412. A rotatable receiving element 418 of the IAB robotic surgical tool is coupled to the spool 1830. For robotic control from the master control console 150, the rotatable receiving element 418 couples to the rotatable driver 234 by means of the pins 422A-422B within the openings 240A-240B, respectively.

Coupled between the spool 1830 and the drum 1854 of the rotatable sleeve are a top cable 1832 and a bottom cable 1834. One end of each cable couples to the spool 1830. The opposite end of each cable couples to the drum 2854. Alternatively, a single cable may be used by appropriately wrapping it around the drum 2834 and the spool 1830. The top cable and the bottom cable wrap different from each other around the spool. They also wrap different from each other around the drum 1854. In this manner, one cable is being let out while the other cable is being taken in by the rotation of the spool. 1854. If the spool 1854 is turning clockwise as indicated by arrow F2, the cable 1832 is taken in, the cable 1834 is let out, and the sleeve 1820' rotates counter clockwise as illustrated by the letter G2. If the spool 1854 is turning counter-clockwise as indicated by arrow F1, the cable 1832 is let out, the cable 1834 is let out, and the sleeve 1820' rotates clockwise as illustrated by the letter G1.

There rotational movement of the receiving element 418 may be transmitted by other means to the rotatable sleeve 1820'. For example, a gear system may be used. In which case, a first worm gear may be used in place of the spool 1830 and a second worm gear coupling to the first may be used in place of the drum 1854.

The flow control system provided by the solid valve bodies 1101, 1101' and their valves was previously described with reference to FIGS. 11A-11E and is incorporated here by reference.

Referring now to FIG. 18E, the hollow rotatable sleeve 1820A' includes a plurality of narrow openings 1840 located around a circumference of a distal end of the sleeve 1820A'. This way, the scale may be seen from different angles. The narrow window openings 1840 may be oval shaped as illustrated or rectangularly shaped. The hollow tube 404 includes a plurality of curved color stripes 1842 around its circumference that may be rectangularly shaped as illustrated by the dashed lines in FIG. 18E. As the sleeve 1820A' rotates, the stripes 1842 are positioned on the hollow tube 404 to be substantially aligned with the window openings 1840.

In one position of the sleeve 1820A', no color stripe or a color stripe representative of fluid flow being completely shut off is located within a window opening 1840. This corresponds to all the valves being closed to shut off the fluid flow through the IAB robotic surgical tool. Rotating the sleeve 1820A' from a shut off position, a first or second color stripe may begin to be revealed, such as illustrated in FIGS. 18E-18G, representative of a first fluid flow in an IAB robotic surgical instrument. The level of fluid flow can be indicated by the amount of color stripe 1842 that is exposed in the window opening 1840. With the color stripe 1842 being completely exposed by the window opening 1840, the corresponding valve of the flow control system may be fully open. With the sleeve 1820A' being rotated still further, a second or third color stripe may begin to be exposed by the window opening 1840. In which case, the prior fluid flow may be substantially shut off and another valve opened to allow another fluid to flow through the IAB robotic surgical tool.

The different color stripes 1842 indicate the flow of different fluids through the IAB robotic surgical. For example, a red color stripe may indicate that all fluid flows are fully shut off. A green color stripe may indicate pressurized gas flow. A blue color stripe may indicate irrigation, An orange color stripe may indicate suction or aspiration.

Referring now to FIG. 18F, the tool 400D includes the rotatable sleeve 1820B' that is similar to the rotatable sleeve 1820A' but has triangular shaped window openings 1850 instead. The hollow tube 404 includes the plurality of color stripes 1842. But for the shape of the window openings, the sleeve 1820'B operates substantially similar to that of sleeve 1820A' described previously.

Referring now to FIG. 18G, the hollow rotatable sleeve 1820C' includes a plurality of narrow rectangular openings 1860 located around a circumference of a distal end. With the plurality of openings 1860, the scale may be seen from different angles and positions of the tool. The narrow window openings 1860 are rectangularly shaped. However, the hollow tube 404 includes a plurality of triangle stripes 1842 curving around its circumference as illustrated by the dashed lines in FIG. 18G. The colored triangle stripes 1862 are positioned on the hollow tube 404 to be substantially aligned with the window openings 186, as the sleeve 1820C' rotates, As the sleeve 1820C' rotates, the level of fluid flow can be indicated by the amount of color triangular stripe 1862 that is exposed in the window opening 1860. As discussed previously, the type of fluid flow may be indicated by the different colors.

The type of user feedback previously disclosed was implemented by the IAB robotic surgical tool. Alternatively, user feedback may be provided by the master control console 150, such as through an electronic visual display of a graphical icon or image.

Figure 19:
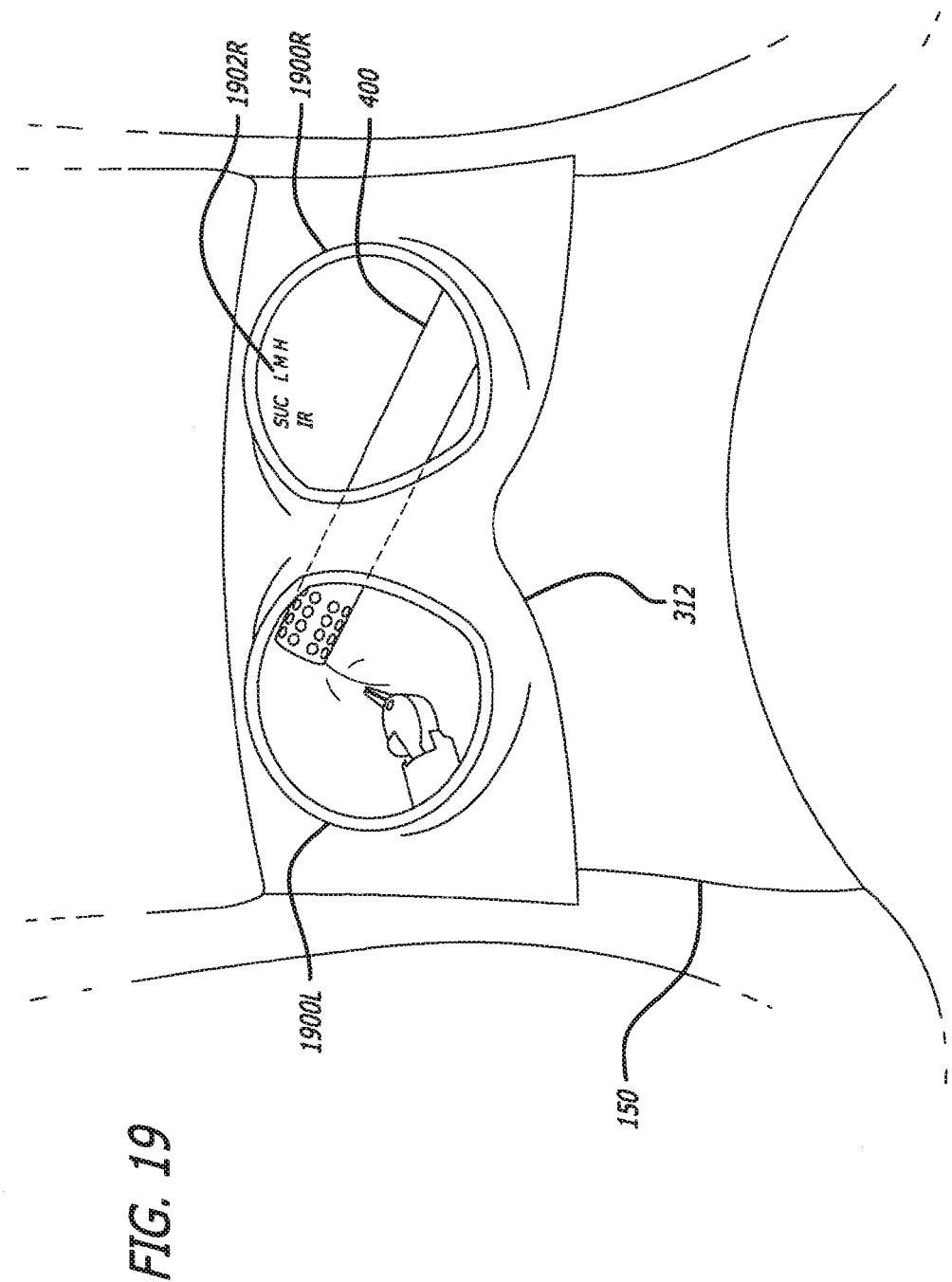
FIG. 19 is a viewer of the robotic surgical master control console of FIG. 3A with an icon overlaid onto the displayed images to provide user feedback as to the control of the irrigation/aspiration/blowing robotic surgical tool.

Referring now to FIG. 19, a simulated 3D image of a surgical site in a viewer 312 of the master control console 150 is illustrated when the operators eyes are in the viewer 312. As illustrated in FIGS. 20A-20B, stereo optic images of a left image 1900L and a right image 1900R are provided at the viewer 312, in order to provide a three-dimensional image when viewed by the operator O. In the left and right views, the IAB robotic surgical tool 400 is located within the surgical site. To provide user feedback as to the fluid flow in the tool 400, icons 1902 are overlaid onto the images displayed in one or both of the displays 1900L, 1900R. The icons may use different colors overlaid on the image in order to display the function of the tool 400. A scale may be provided in the viewer to display the level of the fluid flow in the tool 400. Alternatively abbreviated letters may be used to indicate the type of fluid flow (e.g., S-suction or A-aspiration, I-irrigation, B-blowing) in the tool 400 as well as its level, such as L, M, and H.

Referring now to FIG. 20A, a viewer 312A of the master control console 150 is illustrated. To provide a three-dimensional perspective, the viewer 312A includes stereo images for each eye including left image 400L of the tool 400 and surgical site and a right image 400R of the tool 400 and surgical site. One or more icons 2010R may be overlaid onto the images in the right viewfinder 2001R to indicate the functionality and the level of fluid flow in the IAB robotic surgical tool 400. The images 400R and 400L in the viewfinders may be provided by a right liquid crystal display 2002R and a left liquid crystal display 2002L, respectively.

As the one or more icons 2010R in the viewer 312A are provided in a single viewfinder of the stereo viewer, they are displayed as two-dimensional icons. However, three dimensional images of the icons may be provided and overlaid onto stereo left and right images of the surgical site.

In FIG. 20B, one or more icons to provide user feedback of the control of the IAB robotic surgical tool are overlaid onto both the left image 400L and right image 400R of the surgical site. In the right viewfinder 2001R, a right icon image 2010R is overlaid onto the right image 400R being displayed by the liquid crystal display 2002R. In the left viewfinder 2001L, a left icon image 2010L is overlaid onto the left image 400L of the surgical site provided by the liquid crystal display 2002L. In this manner, a stereo image of the icons may be used to provide user feedback of the control of the IAB robotic surgical tool may be provided in the viewer 312B.

Exemplary Operation of the IAB Robotic Surgical Instruments

In order to use the IAB robotic surgical tools, it is first undergoes an initial setup prior to surgery. The IAB robotic surgical instrument is mounted to a robotic arm 153 of the robotic surgical manipulator 152. One or more hoses 160A-160C are coupled from the IAB robotic surgical instrument to one or more pumps 102A-102C. The robotic surgical manipulator 152 is oriented with the patient P so that the tip of the hollow tube of the irrigation-aspiration robotic surgical instrument may be inserted into the patient near the desired surgical site. During the surgery, the operator O may control the flow of fluids between the surgical site and the IAB robotic surgical instrument from the master control console 150 using the flow control system 417 of the IAB robotic surgical tool. Alternatively or conjunctively, the operator may also control the flow of fluids between the IAB robotic surgical instrument and the one or more pumps. To control the flow of fluids, the operator O at the master control console 150 may generate one or more control signals to control the IAB robotic surgical instrument. The one or more control signals may be directly or indirectly coupled into the IAB robotic surgical instrument. For example, the one or more control signals may be electrical signals that are directly coupled into the IAB robotic surgical instrument to electrically control one or more valves. Alternatively, the one or more control signals may be electrical signals that are translated into a mechanical motion. In this case, the mechanical motion may be directly coupled into IAB robotic surgical instrument while the electrical control signals are indirectly coupled into the IAB robotic surgical instrument. In any case, one or more valves in the IAB robotic surgical instrument may be opened to flow one or more fluids over a surgical site in response to the control signals. Similarly, one or more valves in the IAB robotic surgical instrument may be closed to reduce the flow of the one or more fluids over the surgical site in response to the control signals.

In alternative embodiments of the invention, the control of the flow of fluids between the surgical site and the IAB robotic surgical instrument is provided by controlling the one or more pumps. In which case, the control signals are coupled to the pumps and/or flow control valves located external to the IAB robotic surgical instrument. The IAB robotic surgical instrument may include a coupler to couple between the hoses from the one or more pumps and the hollow tube that is inserted into a patient.

The one or more control signals may be generated in various ways including in response to movement of a touch sensitive handle of a master control console, squeezing of a grip of the touch sensitive handle, rotation of the touch sensitive handle, movement of a foot pedal, or a spoken command at the master control console.

The level of flow of the fluids and the control thereof may be monitored between the surgical site and the IAB robotic surgical instrument through the user-feedback means previously described. One user-feedback means is one or more light emitting diodes coupled near the tip of the hollow tube of the IAB robotic surgical instrument. The one or more light emitting diodes generate a visible light in response to the control of a flow of a fluid through the IAB robotic surgical instrument. Another user-feedback means is a light pipe coupled along the length of the hollow tube of the irrigation-aspiration robotic surgical instrument with a light emitting diode. The light emitting diode couples photons into the light pipe and generates a visible side light in response to the control of a flow of a fluid through the irrigation-aspiration robotic surgical instrument. Still another user-feedback means is a sliding sleeve coaxial with the hollow tube and a scale coupled to the irrigation-aspiration robotic surgical instrument. The sliding sleeve slides along the hollow tube and reveals the scale in response to the control of a flow of a fluid through the irrigation-aspiration robotic surgical instrument.

After the using the IAB robotic surgical instrument, it is removed from the patient and can then be dismounted from the robotic arm of the robotic surgical manipulator 152. If the IAB robotic surgical instrument is to be reused, a modular valve assembly and one or more hoses of the irrigation-aspiration robotic surgical instrument may be discarded and the remaining components of the IAB robotic surgical instrument sterilized for reuse. In the case that the IAB robotic surgical instrument includes a flow control system with an inexpensive valve subassembly, the irrigation-aspiration robotic surgical instrument can be removed from the patient; dismounted from the robotic arm; and then discarded.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art. For example, while an irrigation/aspiration/blowing robotic surgical instrument has been shown and described in a number of embodiments of the invention, it may be modified into an irrigation robotic surgical instrument with a single valve to provide irrigation only or it may be modified into an aspiration robotic surgical instrument with a single valve to provide aspiration only. Furthermore, while aspiration or suction has been described as being provided by a vacuum pump, one would recognize that a pressurized gas may be provided instead, such as air by an air pump. The pressurized gas may be used to blow debris or cut tissue, if sufficient pressure is provided. Rather, the embodiments of the invention should be construed according to the claims that follow below.

What is claimed is:

1. A teleoperated surgical instrument comprising:
   a housing configured to couple to a teleoperated manipulator;
   an elongated tube having a first end and a second end opposite the first end, the first end being mounted to the housing, and the second end having one or more openings configured to deliver or receive a fluid at a surgical site; and
   a flow control system in the housing, the flow control system including:
   a first tubular member coupled to the elongated tube, and
   a first control element rotatable relative to the housing and the first tubular member, the first control element including a receiving portion coupled to a shaft portion, wherein the receiving portion is configured to couple with the teleoperated manipulator and rotate to control flow of the fluid through the first tubular member.

2. The teleoperated surgical instrument of claim 1, wherein the first tubular member is flexible, and wherein rotation of the receiving portion causes compression of the first tubular member to control flow of the fluid through the first tubular member.

3. The teleoperated surgical instrument of claim 2 wherein the flow control system further includes:
   a second flexible tubular member,
   a second control member rotatable relative to the housing and configured to compress the second flexible tubular member to control a flow of the fluid through the second flexible tubular member, and
   a coupler coupled to the first and second tubular members and configured to route the flow of the fluid to the elongated tube.

4. The teleoperated surgical instrument of claim 2 wherein the flow control system further includes a bulkhead rigidly secured to the housing, and wherein rotation of the receiving portion causes compression of the first tubular member against the bulkhead.

5. The teleoperated surgical instrument of claim 1 wherein the receiving portion is configured to rotate in response to a command to the teleoperated manipulator from a processor.

6. The teleoperated surgical instrument of claim 1 wherein the receiving portion includes a pair of pins sized and spaced to couple with the teleoperated manipulator.

7. The teleoperated surgical instrument of claim 1 wherein the fluid is a gas.

8. The teleoperated surgical instrument of claim 1 further comprising:
   a feedback system including a light emitting element, the feedback system configured to cause light emission from the light emitting element when the fluid is delivered to the surgical site and to cause no light emission from the light emitting element when flow of the fluid is stopped.

9. The teleoperated surgical instrument of claim 1 further comprising:
   an electrical circuit within the housing and configured to generate an electrical signal when the fluid is delivered to the surgical site.

10. A surgical instrument, comprising:
    a housing configured to couple to a teleoperated manipulator;
    a tube coupled to and extending into the housing; and
    a control system in the housing, the control system comprising:
    a valve coupled to the tube;
    a first actuating mechanism coupled to the valve and configured to actuate the valve in response to the teleoperated manipulator; and
    a second actuating mechanism coupled to the valve and configured to actuate the valve independent of the first actuating mechanism.

11. The surgical instrument of claim 10, wherein the first actuating mechanism is configured to actuate the valve in response to rotation of a coupled element of the teleoperated manipulator.

12. The surgical instrument of claim 10, wherein the first actuating mechanism is configured to actuate the valve in response to linear motion of a coupled element of the teleoperated manipulator.

13. The surgical instrument of claim 10, wherein the valve comprises an electrically operated valve.

14. The surgical instrument of claim 10, wherein the valve comprises a magnetically operated valve.

15. The surgical instrument of claim 10 further comprising a plurality of tube fittings extending into the housing and coupled to the valve, wherein the valve is configured to direct fluid flow between the plurality of tube fittings and the tube.

16. The surgical instrument of claim 10, wherein the control system is configured to prevent fluid flow through tube when the housing is uncoupled from the teleoperated manipulator.

17. The surgical instrument of claim 10 further comprising:
- a feedback system including a light emitting element, the feedback system configured to cause a light emission from the light emitting element if a fluid flow through the tube occurs and to stop the light emission from the light emitting element if the fluid flow through the tube stops.

* * * * *